US012245594B2

(12) United States Patent
Vogan et al.

(10) Patent No.: US 12,245,594 B2
(45) Date of Patent: Mar. 11, 2025

(54) METHODS FOR OBTAINING AND USING PLANTS AND PLANT PARTS WITH INCREASED NUTRIENT, OIL, AND/OR PROTEIN CONTENT

(71) Applicant: NewLeaf Symbiotics, Inc., St. Louis, MO (US)

(72) Inventors: Patrick Vogan, St. Louis, MO (US); Janne Kerovuo, Los Angeles, CA (US); Charles Michael McFatrich, Washington, MO (US); Natalie Breakfield, St. Louis, MO (US)

(73) Assignee: NewLeaf Symbiotics, Inc., St. Louis, MO (US)

( * ) Notice: Subject to any disclaimer, the term of this patent is extended or adjusted under 35 U.S.C. 154(b) by 888 days.

(21) Appl. No.: 17/309,505

(22) PCT Filed: Dec. 2, 2019

(86) PCT No.: PCT/US2019/064033
§ 371 (c)(1),
(2) Date: Jun. 2, 2021

(87) PCT Pub. No.: WO2020/117689
PCT Pub. Date: Jun. 11, 2020

(65) Prior Publication Data
US 2022/0015370 A1    Jan. 20, 2022

Related U.S. Application Data

(60) Provisional application No. 62/900,766, filed on Sep. 16, 2019, provisional application No. 62/878,164, filed on Jul. 24, 2019, provisional application No. 62/846,547, filed on May 10, 2019, provisional application No. 62/802,038, filed on Feb. 6, 2019, provisional application No. 62/774,640, filed on Dec. 3, 2018.

(51) Int. Cl.
| | | |
|---|---|---|
| A01N 63/20 | (2020.01) |
| A23K 10/30 | (2016.01) |
| A23K 20/147 | (2016.01) |
| A23K 20/158 | (2016.01) |
| A23K 20/174 | (2016.01) |
| A23K 20/20 | (2016.01) |
| A23K 20/22 | (2016.01) |
| A23K 20/24 | (2016.01) |
| A23K 20/26 | (2016.01) |
| A23K 50/10 | (2016.01) |
| A23K 50/30 | (2016.01) |
| A23K 50/75 | (2016.01) |
| A23K 50/80 | (2016.01) |
| A23L 33/105 | (2016.01) |
| A23L 33/115 | (2016.01) |
| A23L 33/15 | (2016.01) |
| A23L 33/16 | (2016.01) |
| A23L 33/185 | (2016.01) |
| C12Q 1/689 | (2018.01) |

(52) U.S. Cl.
CPC .............. *A01N 63/20* (2020.01); *A23K 10/30* (2016.05); *A23K 20/147* (2016.05); *A23K 20/158* (2016.05); *A23K 20/174* (2016.05); *A23K 20/22* (2016.05); *A23K 20/24* (2016.05); *A23K 20/26* (2016.05); *A23K 20/30* (2016.05); *A23K 50/10* (2016.05); *A23K 50/30* (2016.05); *A23K 50/75* (2016.05); *A23K 50/80* (2016.05); *A23L 33/105* (2016.08); *A23L 33/115* (2016.08); *A23L 33/15* (2016.08); *A23L 33/16* (2016.08); *A23L 33/185* (2016.08); *C12Q 1/689* (2013.01)

(58) Field of Classification Search
CPC ..................................................... A01N 63/20
See application file for complete search history.

(56) References Cited

U.S. PATENT DOCUMENTS

| | | | |
|---|---|---|---|
| 5,302,525 A | 4/1994 | Groleau et al. | |
| 10,212,939 B2* | 2/2019 | Floro | ..................... A01N 63/20 |
| 2010/0249378 A1 | 9/2010 | Wanasundara et al. | |
| 2012/0017338 A1 | 1/2012 | Wu et al. | |
| 2013/0288318 A1 | 10/2013 | Wood et al. | |

(Continued)

FOREIGN PATENT DOCUMENTS

| | | |
|---|---|---|
| WO | 2015085063 A1 | 6/2015 |
| WO | 2015085116 A1 | 6/2015 |

(Continued)

OTHER PUBLICATIONS

Ekin, Zehra, "Performance of phosphate solubilizing bacteria for improving growth and yield of sunflower (*Helianthus annuus* L.) in the presence of phosphorus fertilizer", African Journal of Biotechnology, vol. 9, No. 25, pp. 3794-3800, Jun. 21, 2010.
International Searching Authority in connection with PCT/US19/64034 filed Dec. 2, 2019, "International Search Report", 6 pages, mailed Apr. 14, 2020.
International Searching Authority in connection with PCT/US19/64033 filed Dec. 2, 2019, "Written Opinion of the International Searching Authority", 22 pages, mailed May 19, 2020.

(Continued)

*Primary Examiner* — Johann R Richter
*Assistant Examiner* — Danielle Johnson
(74) *Attorney, Agent, or Firm* — McKee, Voorhees & Sease, PLC

(57) ABSTRACT

Methods for identifying *Methylobacterium* strains which can be used to increase mineral nutrient, vitamins, oil and/or protein content in plants are provided. Also provided are related methods of providing seed lots, food ingredients, feed ingredients, food, or feed with increased mineral nutrient, vitamins, oil and/or protein content. Methods of providing increased mineral nutrient and/or vitamin content, and/or increased oil and/or protein yield from plant seed lots are also provided.

7 Claims, 13 Drawing Sheets

Specification includes a Sequence Listing.

(56) References Cited

U.S. PATENT DOCUMENTS

| | | | |
|---|---|---|---|
| 2016/0046925 | A1 | 2/2016 | Bogosian |
| 2016/0295868 | A1 | 10/2016 | Jones et al. |
| 2016/0302423 | A1 | 10/2016 | Jones et al. |
| 2016/0302425 | A1* | 10/2016 | DiDonato .............. A01N 63/20 |
| 2017/0086464 | A1 | 3/2017 | Floro et al. |
| 2017/0238553 | A1 | 8/2017 | Jones et al. |
| 2018/0142230 | A1 | 5/2018 | Bogosian |
| 2020/0367506 | A1 | 11/2020 | Martinez-Gomez |

FOREIGN PATENT DOCUMENTS

| | | |
|---|---|---|
| WO | 2015114552 A1 | 8/2015 |
| WO | 2017112827 A1 | 6/2017 |
| WO | 2018102733 A1 | 6/2018 |
| WO | 2018106899 A1 | 6/2018 |
| WO | 2020117690 A1 | 6/2020 |
| WO | 2020163027 A1 | 8/2020 |

OTHER PUBLICATIONS

International Searching Authority in connection with PCT/US2020/012041 filed Jan. 2, 2020, "Written Opinion of the International Searching Authority", 15 pages, mailed May 7, 2020.

International Searching Authority in connection with PCT/US19/64034 filed Dec. 2, 2019, "Written Opinion of the International Searching Authority" 9 pages, mailed Apr. 14, 2020.

Madhaiyan et al., "Leaf-residing Methylobacterium species fix nitrogen and promote biomass and seed production in Jatropha curcas", Biotechnol Biofuels, vol. 8, No. 222, pp. 1-14, 2015.

Motlagh et al., "Effect of irrigation disruption and biological phosphorus on the biomass and oil content of canola (*Brassica napus* L.)", Intl J Agri Crop Sci., vol. 4, No. 10, pp. 627-632, 2012.

Pohjanen et al., "Interaction with ectomycorrhizal fungi and endophytic Methylobacterium affects nutrient uptake and growth of pine seedlings in vitro", Tree Physiology, vol. 34, pp. 993-1005, 2014.

Stefanescu et al., "Maldi-Tof Mass Spectrometric Analysis of Zeins Extracted From Maize Seeds", Acta Chemica IASI, vol. 25, No. 1, pp. 73-86, 2017.

Aquino et al., "Plant-promoting rhizobacteria Methylobacterium komagatae increases crambe yields, root system and blant height," Industrial Crops & Products, Oct. 2018, vol. 121, pp. 277-281.

Biari et al., "Growth Promotion and Enhanced Nutrient Uptake of Maize (*Zea mays* L.) by Application of Plant Growth Promoting Rhizobacteria in Arid Region of Iran," Journal of Biological Sciences, Jun. 2008, vol. 8, No. 6, pp. 1015-1020.

Extended European Search Report in EP19891779.1, mailed Oct. 11, 2022, 15 pages.

Jimenez-Gomez et al., "Plant probiotic bacteria enhance the quality of fruit and horticultural crops," AIMS Microbiology, Jun. 19, 2017, vol. 3, Issue 3, pp. 483-501.

Lamont et al., "Seeds as a Source of Carbon, Nitrogen, and Phosphorus for Seedling Establishment in Temperate Regions: A Synthesis," American Journal of Plant Sciences, May 2013, vol. 4, pp. 30-40.

* cited by examiner

SEQUENCE LISTING

<160> NUMBER OF SEQ ID NOS: 76

<210> SEQ ID NO 1
<211> LENGTH: 300
<212> TYPE: DNA
<213> ORGANISM: Methylobacterium

<400> SEQUENCE: 1

```
acggtcaccc cacggactgg gcgagtacct caccggtgtt ctatcataac gccgagttag     60 tttcgaccg tcccttatgc gatgtaccac cggtgtcggc agccgatttc gtcccaccgg     120
gagctggcgt tccggttcag accaccatca tcggtcacga tgtctggatt ggacacgggg    180
ccttcatctc ccccggcgtg actataggaa acgcgcgat cgtcggggcc caggcggtcg     240
tcacaagaga tgtcccaccc tatgcggtag ttgctggcgt ccccgcgacc gtacgacgat    300
```

<210> SEQ ID NO 2
<211> LENGTH: 300
<212> TYPE: DNA
<213> ORGANISM: Methylobacterium

<400> SEQUENCE: 2

```
ccaataaaag cgttggccgc ctgggcaacc cgatccgagc ctaagactca aagcgcaagc     60
gaacacttgg tagagacagc ccgccgacta cggcgttcca gcactctccg gctttgatcg    120
gataggcatt ggtcaaggtg ccggtggtga tgacctcgcc cgccgcaagc ggcgaattac    180
tcggatcagc ggccagcacc tcgaccaagt gtcggagcgc gaccaaaggg ccacgttcga    240
ggacgtttga ggcgcgacca gtctcgatag tctcatcgtc gcggcgaagc tgcacctcga    300
```

<210> SEQ ID NO 3
<211> LENGTH: 300
<212> TYPE: DNA
<213> ORGANISM: Methylobacterium

<400> SEQUENCE: 3

```
cgatggcacc gacctgccat gcctctgccg tccgcgccag aatggtaaag aggacgaagg     60
gggtaaggat cgtcgctgca gtgttgagca gcgaccagag aaggggggccg aacatcggca   120 tcaaacctcg attgccactc ggacgcgaag cgcgtcttga aggagggatg gaagcgaaac    180
ggccgcagag taaccgccga cgaaagattg caccccctcat cgagcaggat cggaggtgaa   240
ggcaagcgtg ggttattggt aagtgcaaaa aatataatgg tagcgtcaga tctagcgttc    300
```

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4

```
cctcaccggt gttctatcat aac                                              23
```

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5

```
ccgatgatgg tggtctgaac                                                  20
```

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
```

-continued cgtcccttat gcgatgtacc a        21

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
gatccgagcc taagactcaa ag        22

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gaccaatgcc tatccgatca a        21

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
aacacttggt agagacagcc        20

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
aaggagggat ggaagcgaaa c        21

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
ataacccacg cttgccttc        19

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
cgcagagtaa ccgccgacga a        21

<210> SEQ ID NO 13
<211> LENGTH: 300
<212> TYPE: DNA

<213> ORGANISM: Methylobacterium

<400> SEQUENCE: 13

```
gcaaaacgac ctaatagttc tacagcggca tgcgccaagt cagcgcggtg aacagtatac      60
ctgggagcaa cttgtcctcc gaaacccaca taaaacaaat tactcctggc agtgcccagt     120
ccatcaaaat cgaatacaat atttctcgag gaggcatctg taatagcctg ccaaagcaac     180
aaagctatgg cgccgttatg actttcattg cttctggtag acataaaata atatgccgat     240
ttgtgatccc aaatgtagaa tattgccgca tcaattgcgc aagtttatt tcggatcgat      300
```

<210> SEQ ID NO 14
<211> LENGTH: 300
<212> TYPE: DNA
<213> ORGANISM: Methylobacterium

<400> SEQUENCE: 14

```
ggcgccaacg gtatgatcgc atgatttcc tgcggcatag cttgcgggaa tggcgtattt       60
ggcgctctcc tcaggaattt ctaagggcat acgcaggaac tctacagcac ttttactggt    120
attttgtagt gacagcggag gaggctggtg ctcaaggtaa tcgtgatgaa gtgatccggg    180
ccattcgggg cgcgtttcta gtcttccaa tccgcgccct gtaccacgta ttacgccgga     240
ccggtctgcg ccgcgccgcc ctcttgaccg ccctaaatgt ctaagagcgt ctaacaaagc    300
```

<210> SEQ ID NO 15
<211> LENGTH: 300
<212> TYPE: DNA
<213> ORGANISM: Methylobacterium

<400> SEQUENCE: 15

```
gacgatatcg ctcatcttca ctgcattgaa gctggtgccg tactgcatag ggatgaaaaa     60
gtgatgcgga tagacggctg acgggaaagc gcctggtcga tcgaagactt tgctgacgag   120
gttgtggtag ccccggatat aggcatcgaa ggccgggacg ttgatcccat cctttgcctt   180
atcttgactg gcgtcgtcgc gtgccgtcag aacgggcacg tcgcaggtca tcgaggccag   240
caccttgcgg aacacctgcg ttccgccgtt gggattatcg acggcgaacg cggtggccgc   300
```

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16

```
gtcctccgaa acccacataa a                                              21
```

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17

```
ctaccagaag caatgaaagt cat                                            23
```

<210> SEQ ID NO 18
<211> LENGTH: 22
<212> TYPE: DNA
<213> ORGANISM: Artificial Sequence
```

<220> FEATURE:
<223> OTHER INFORMATION: Synthetic

<400> SEQUENCE: 18
tctgtaatag cctgccaaag ca                                              22

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
ggctggtgct caaggtaat                                                  19

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
acatttaggg cggtcaagag                                                 20

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
atgaagtgat ccgggccat                                                  19

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
ccgtactgca tagggatgaa a                                               21

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
taaggcaaag gatgggatca a                                               21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
ttgctgacga ggttgtggta g                                               21

```
<210> SEQ ID NO 25
<211> LENGTH: 300
<212> TYPE: DNA
<213> ORGANISM: Methylobacterium

<400> SEQUENCE: 25
caactatgta gacccgacgg tgcgatttca cttcgcaaag ccgcagggca gcacccttgc      60
gctcaatgtt gacgccagcg tgatctatac tattaccgtc acgcacacgc agggcggcgt     120
acagattcat cgcgagagta agaaccacca tcagaccatc acgcgcagcg acctgagcaa     180
gcagttcggc gttggtgtgg ccgaccagct gacgcgcgat caggtcatga aggtgatcga     240
gtcggcattt cgcgacgcta cccgctaaga tcggcgccca cgaaacgcta cgagactagg     300

<210> SEQ ID NO 26
<211> LENGTH: 300
<212> TYPE: DNA
<213> ORGANISM: Methylobacterium

<400> SEQUENCE: 26
agccggcatc ttgttcaagg cgctcacctc gacgccgacg ctgtaggcga cttgagaggg      60
cgtctcatat gaacgaagca tcttcgcgta gagaaccttc ttgttctcct gcgtgatgtt     120
cgctttgcag acgttgactg ccgccatgaa cgccgaagcc ttgcgcgctt catcgtaatc     180
gcctgcgaag gcgggtagtg aaaagcttag tgcaatggca aacacagccg ccgaacgtcg     240
catggtatcc gtccccgatt gacggcagtg ccgccatatc tcggctttag cagagctgat     300

<210> SEQ ID NO 27
<211> LENGTH: 300
<212> TYPE: DNA
<213> ORGANISM: Methylobacterium

<400> SEQUENCE: 27
aacctgcgcc ggccgaggtt tcgcgagccg tcgccacggg caacgcctcg cccgcgatgt      60
gcaaaaaagt ccccggcact tcgcgccgtc gtccgatcca cgaccgcgaa tttctcaacg     120
agtacaaggt gcttatggga gatccgagcg tccgtcccgg agcccgagac cgcgcggccc     180
gagtaatagg cgaaaaagac tcctactcct cgggcttctc gggccccctc agcaacatct     240
acgcttgccg cccatcaccc tggcgggaga tcagcgacga gacacaggcc cacttcgccc     300

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
ttgacgccag cgtgatctat ac                                               22

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
gtgatggtct gatggtggtt ct                                               22
```

```
<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
tattaccgtc acgcacacg                                                  19

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
cttcgcgtag agaaccttct tgtt                                            24

<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32
cttcgcaggc gattacgatg aa                                              22

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
cgtgatgttc gctttgcaga                                                 20

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
ccgcgaattt ctcaacgagt aca                                             23

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
gcccgaggag taggagtctt t                                               21

<210> SEQ ID NO 36
<211> LENGTH: 20
<212> TYPE: DNA
<213> ORGANISM: Artificial Sequence
<220> FEATURE:
<223> OTHER INFORMATION: Synthetic
```

<400> SEQUENCE: 36
aggtgcttat gggagatccg                                              20

<210> SEQ ID NO 37
<211> LENGTH: 300
<212> TYPE: DNA
<213> ORGANISM: Methylobacterium

<400> SEQUENCE: 37
agtcattgat caagcaaccc ctattgagtt ggatatcgaa ggatcaaggt cgcgtcaata    60
gatgcatcta tcaggccaaa tgtcgctttt caagaatggc tctttcgaag ctatctttat   120
aatcgctcgc cattctctca ttaccaaaat cgaccttaac tagctcgaca ttgatgcgag   180
cagctccggc aaacgaggag agattgacct taaaggaatt gaacgcctca agcaattcag   240
acacattacc aggagtgcta tagcaacaac cagacccata tcggtcaata acctcttta    300

<210> SEQ ID NO 38
<211> LENGTH: 300
<212> TYPE: DNA
<213> ORGANISM: Methylobacterium

<400> SEQUENCE: 38
cgcaaaacga tttatcactg ccatcttgtt gtttgataac cctttttac cagacgttat     60 gctgggcgag aaagaggact agcagatcgg agcggtatcg cgattttcg gtagttcgcg    120 cctacaacag gataagatcc gatagtgaag caacatggct gttttttgat ttgtaagtca   180
gcaacttaag cagccagcct atctgccgtc gcagacgctt gaggcatcgg gcagcatctt   240
agaaaaggtg gcagtaattg ccacagcgga acgtagcggc acggataagc acgcagggtc   300

<210> SEQ ID NO 39
<211> LENGTH: 300
<212> TYPE: DNA
<213> ORGANISM: Methylobacterium

<400> SEQUENCE: 39
cccatctgga cccaatatcc ccttcatcga caattcccga gtaagtgtgg gttcgaggat    60
ttcgcgaaac agccttgttc gttcctccgg ccttaaaatt ggcgtgccgt cgggagatcg   120
ataggcatcc cttacctgcc tttcgaccgc cggcacacgc gcgccggtcg tcgtgttcac   180
ggccacggaa tggacgaagg tgcgccgctc atttcgctcg tttgccgtct ccaccatcca   240
ggaggccagc aggacggttt cgtctcgacc gccggtcaca cacaccgcaa gggactcagg   300

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
tcgctcgcca ttctctcatt ac                                            22

<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41

```
aggtcaatct ctcctcgttt gc                                              22

<210> SEQ ID NO 42
<211> LENGTH: 18
<212> TYPE: DNA
<213> ORGANISM: Artificial Sequence
<220> FEATURE:
<223> OTHER INFORMATION: Synthetic

<400> SEQUENCE: 42
tcgacattga tgcgagca                                                   18

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
ttcgcgccta caacaggata ag                                              22

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
cagataggct ggctgcttaa gtt                                             23

<210> SEQ ID NO 45
<211> LENGTH: 18
<212> TYPE: DNA
<213> ORGANISM: Artificial Sequence
<220> FEATURE:
<223> OTHER INFORMATION: Synthetic

<400> SEQUENCE: 45
tccgatagtg aagcaaca                                                   18

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
gagtaagtgt gggttcgagg attt                                            24

<210> SEQ ID NO 47
<211> LENGTH: 23
<212> TYPE: DNA
<213> ORGANISM: Artificial Sequence
<220> FEATURE:
<223> OTHER INFORMATION: Synthetic

<400> SEQUENCE: 47
aggtaaggga tgcctatcga tct                                             23

<210> SEQ ID NO 48
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 48
cggaggaacg aacaaggc                                                      18

<210> SEQ ID NO 49
<211> LENGTH: 300
<212> TYPE: DNA
<213> ORGANISM: Methylobacterium

<400> SEQUENCE: 49
acctgctaaa atcacgtcct ctcagattga aaaatcattg aagaaacgtg tcgaacgatt        60
gccggggatt atgacgttag atcaattgaa aaatacaagc tttgaaattg agttacagcc       120
aaaagatgcc ccggatccgg acccatcaga cttcggtggc tagttcgagc caaactcgaa       180
cgtcgccatg gcgcgcaagt cgcaatacca tttcacagcg cagcggttat ttcgttgtac       240
actgtagcaa tgcgtcggct tgcgcgcttc cgctggcgat caaaggtccg ccgatttacg       300

<210> SEQ ID NO 50
<211> LENGTH: 300
<212> TYPE: DNA
<213> ORGANISM: Methylobacterium

<400> SEQUENCE: 50
tcccgaacat acaatggagg aagcgtgtgg taggccaatt tgtaacgaaa tatggcatcg        60
gtcacggctc tctcaataaa ttcgatctca agtcttctga acgagcatgc ctcatcctta       120
tcctgagcga acgcctgcca gtttgcagtc attccaacat acatagccaa aaaggcgagg       180
tagaccttca tacgggcacc tcaatcgtcc ccattcgttc aagctccttc aagataacag       240
ccgcaccaca ttgctgagat cgaagattcg gatcaaatat tccatcaaat ttatactttc       300

<210> SEQ ID NO 51
<211> LENGTH: 300
<212> TYPE: DNA
<213> ORGANISM: Methylobacterium

<400> SEQUENCE: 51
gcatcctttg cgctcgcagg cctaaggtca agcccggtta cttcgtttgg tagaacgagg        60
tagacgatgc ctagtcttaa ggtggcccat gttaaccaac agggccagaa catgattata       120
gttccgttag atgccaactt cggttacaaa accgatggtg agcagtccga catcatgttc       180
gaaatacagg acgcggcgcg gtccgccggt cttgcgggtg ccgtagtagc gttctggcag       240
tcaggtggac aaacccgttt ccggggcccg gctccgtggc acccattcct tcgcagcctc       300

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
gcgcaagtcg caataccatt tc                                                 22

<210> SEQ ID NO 53
<211> LENGTH: 21
<212> TYPE: DNA
<213> ORGANISM: Artificial Sequence
```

```
<220> FEATURE:
<223> OTHER INFORMATION: Synthetic

<400> SEQUENCE: 53
cgtaaatcgg cggacctttg a                                              21

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54
cgcagcggtt atttcgttg                                                 19

<210> SEQ ID NO 55
<211> LENGTH: 22
<212> TYPE: DNA
<213> ORGANISM: Artificial Sequence
<220> FEATURE:
<223> OTHER INFORMATION: Synthetic

<400> SEQUENCE: 55
acgagcatgc ctcatcctta tc                                             22

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
cgattgaggt gcccgtatga a                                              21

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tgccagtttg cagtcattcc                                                20

<210> SEQ ID NO 58
<211> LENGTH: 23
<212> TYPE: DNA
<213> ORGANISM: Artificial Sequence
<220> FEATURE:
<223> OTHER INFORMATION: Synthetic

<400> SEQUENCE: 58
cccggttact tcgtttggta gaa                                            23

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
cgaagttggc atctaacgga acta                                           24
```

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60

```
tggcccatgt taaccaacag                                              20
```

<210> SEQ ID NO 61
<211> LENGTH: 300
<212> TYPE: DNA
<213> ORGANISM: Methylobacterium

<400> SEQUENCE: 61

```
gcccttctgt caggcgatat tgtataatgg cgttgcccca atagaagcag ccattcgtgc    60
gagggcagca gcgacgctag gtcgaaagag catcctaatc tcgatcaaga tgcgactgag   120
atttctgatg aaaatatcta gacacaagca aagctggtga aattacaacg atcatggcga   180
caattgcggc caattcggcc ggaacttgaa ggaacataaa aatgaatatt acaaatatac   240
cgcaaagcat gtagagttgc tacaccaagg gtcgggacgt ccaaaaaaac tcactgagga   300
```

<210> SEQ ID NO 62
<211> LENGTH: 300
<212> TYPE: DNA
<213> ORGANISM: Methylobacterium

<400> SEQUENCE: 62

```
ggaacataaa aatgaatatt acaaatatac cgcaaagcat gtagagttgc tacaccaagg    60
gtcgggacgt ccaaaaaaac tcactgagga agtcgactgg aagcacgagg cgccccccc   120 aggagcgggg cgaccggcaa gggggcccgc aattgtcgcc atgatcgacc agcttaggta   180
ggatcctctt tcgacctaac gaatggctgc ttctattggg gcaacgccat tatacaatat   240
cgcctgacca tctgaaacgc ggcccggtcc accggcaggt tggcgacgac agcgtcggag   300
```

<210> SEQ ID NO 63
<211> LENGTH: 300
<212> TYPE: DNA
<213> ORGANISM: Methylobacterium

<400> SEQUENCE: 63

```
cggcgtcgac cagccgggcg aactgcttgg gcatgctctc ccgcgacgcc ggccacagcc    60
gcgtccccgt ccctccgcac aggatcatcg ggtggatttg aaaggcaaaa cgggacatca   120
ggataggccg ctcaggcgtt ggcgctgagg cgcttgatgt cggcgtcgac catctcggtg   180
atcagcgcct cgaggctggt ctcggcctcc cagccgaagg tcgccttggc cttggcgggg   240
ttgcccagca gcacctcgac ctctgccggc cggaacagcg ccgggtcgac gatcaggtgg   300
```

<210> SEQ ID NO 64
<211> LENGTH: 300
<212> TYPE: DNA
<213> ORGANISM: Methylobacterium

<400> SEQUENCE: 64

```
ctggacatgc gcccaccccg gccaagtccg accgcaccgg caaccgctcc tgtagtcgtc    60
gtcatcgttc tcacccctga ggcggagacc gtccgctaac ggggtgtctc aagcaaccgt   120
ggggcggagg aacacgcacg tagtcgcgtt tcaaggttcg cacgaacgcc tcggccatgc   180
```

```
cgttgctctg cgggctctcc agcggcgtcg tttttggcac caaaccaagg tcgcgggcga    240
agcggcgcgt gtcgcgggga ctgtcaggaa tttcgtgtgg gggcggccat agtggatccg    300

<210> SEQ ID NO 65
<211> LENGTH: 300
<212> TYPE: DNA
<213> ORGANISM: Methylobacterium

<400> SEQUENCE: 65
ggaaatcggc ttcaagtacg acgtcacgcc ggccatgcag gtcacgggtg cactgttcaa     60
tctcgagcgc gacaaccagc cgttcccctc gaacgtggag tccggcctcg tccttggcgc    120
aggtcagaca cgcacccagg cgcggaaat cggcctggcc ggctatctaa ccgattggtg    180
gcaggtcttt ggcggctacg cttataccga ggcacgcgta ctctcgccac tggaagacga    240
tggagacgtg atcgcagcag gtaatctcgt cggcaacgtt ccgctaaata ctttcagtct    300

<210> SEQ ID NO 66
<211> LENGTH: 300
<212> TYPE: DNA
<213> ORGANISM: Methylobacterium

<400> SEQUENCE: 66
cggcctggcc ggctatctaa ccgattggtg gcaggtcttt ggcggctacg cttataccga     60
ggcacgcgta ctctcgccac tggaagacga tggagacgtg atcgcagcag gtaatctcgt    120
cggcaacgtt ccgctaaata ctttcagtct gttcaacaag ttcgatatca acgagaattt    180
ctccgttgct ctgggctatt actatcagga tgccagcttt gcctcctcag acaatgcagt    240
gcgtttgcca agttattcgc ggttcgatgg cgggttgttc tatcgattcg acgagttgac    300

<210> SEQ ID NO 67
<211> LENGTH: 300
<212> TYPE: DNA
<213> ORGANISM: Methylobacterium

<400> SEQUENCE: 67
acgttccgct aaatactttc agtctgttca acaagttcga tatcaacgag aatttctccg     60
ttgctctggg ctattactat caggatgcca gctttgcctc ctcagacaat gcagtgcgtt    120
tgccaagtta ttcgcggttc gatggcgggt tgttctatcg attcgacgag ttgacacgcg    180
ttcagcttag cgtcgagaac attttcgaca ggcgttacat catcaactcc aacaacaaca    240
acaacctcac gcctggcgcg ccgagaacag tccgcgtgca attgatcgct cggttctaaa    300

<210> SEQ ID NO 68
<211> LENGTH: 300
<212> TYPE: DNA
<213> ORGANISM: Methylobacterium

<400> SEQUENCE: 68
agcccacaag cctgatgcac ttaactacat cctctaatgt cgcgccaatt tgcttggcgg     60
caggggatgt tgtatcgtca taggcttgtc taaccggaac ttgtttgcca atctctttgg    120
cgatcgcaac cgccatctcg tgttcgtcaa ccatgtgcgc gttcctctaa ttgcactcat    180
ggtgccacgt gcacctccga tcgtctcgtg tctagaatga aggtgggaac aaccttacac    240
aggctttcgc gacgcgcgaa tttctggttt ctccgcctcg gatgtgggtt tgagcgcttc    300

<210> SEQ ID NO 69
```

```
<211> LENGTH: 300
<212> TYPE: DNA
<213> ORGANISM: Methylobacterium

<400> SEQUENCE: 69
cttttcattt gtcatgatct cgaccaaggt attcacggca agctcggtct gttgcttagc    60
aagtgcctga acttcgcgaa cgatcggctc tcgacccttc gggttcgaga cctgtccctt   120
ttgaaaacca cgtgccctac acttttcggg atcaaggtgc gggttggctt tggtcaaaat   180
tctctggcgt cccattacac gccctccgca tcatcgttcc cgcgaacgat ctgaccccg    240
acttccgcga ggaagcgtgt ggcgtgatcc tcgaagcgga atgccacctc gaactgttcc   300

<210> SEQ ID NO 70
<211> LENGTH: 300
<212> TYPE: DNA
<213> ORGANISM: Methylobacterium

<400> SEQUENCE: 70
cagcagcaag cagatcgttg aaaaccgctt gaaccgcatc ttgatcggga ccggaaccaa    60
tcaggtcatc taggtaaacc gagacgtaaa ctcgtttgcg ctcggcatct ttcagaacgt   120
ccgtgatgcc agaccgcatt agtaccatcg tcgccaaggc gggcgactga acgaagccga   180
tcggcagaga gtaacgggga ccgcccctaa tcgggttgcg aacgcaagac cacttagcaa   240
aggttcgagc acggccgaac ttcgcatggt ggagagccgc ggcaacacgg ttccgtgata   300

<210> SEQ ID NO 71
<211> LENGTH: 300
<212> TYPE: DNA
<213> ORGANISM: Methylobacterium

<400> SEQUENCE: 71
tagacattcc aacaaaccgg caagaggctc gtcctcactc gaggatttgt tgggacttgc    60
atgatgtcga agcggagccg ttatgacctg ggtgcgatca tgcgccgagc atgggagatg   120
gctcgggagg cggcattcgc ggttggcgag cgggcacgga ctcaccttgc tgccgcgatg   180
cgcagcgcgt gggccgaagc caagttggca ctcgcgccca cgaagacgga gcaggatcgt   240
ctctctccga gcgacatgat cggacatgag gacgcctacc aaggccgggt tctaaaatat   300

<210> SEQ ID NO 72
<211> LENGTH: 300
<212> TYPE: DNA
<213> ORGANISM: Methylobacterium

<400> SEQUENCE: 72
aagatggata cgacaagcgc gattacatta tttgcgaaat agatggacaa ataaaagaca    60
aaggactgat gtatttcctt aaatctggac aagttgacct ctttcacata gaagtcacca   120
ctccctttgg gacaatttgg tgtcacgaaa acatagaggc cgaacttctt agctgaatta   180
tcgcgctccg ggttcttatg cggctgagtg aagcgcggga cagcttgcga gcagggccgc   240
caatggcagc cgggatgaca caatgctcgg tctcccgacg cttcttcaat cgggagcgct   300

<210> SEQ ID NO 73
<211> LENGTH: 299
<212> TYPE: DNA
<213> ORGANISM: Methylobacterium

<400> SEQUENCE: 73
agctgaatta tcgcgctccg ggttcttatg cggctgagtg aagcgcggga cagcttgcga    60
```

```
gcagggccgc caatggcagc cgggatgaca caatgctcgg tctcccgacg cttcttcaat    120
cgggagcgct tcgcagcccg gggcggcgcg ctcatgcgtc acgacctggg ccctgcgcac    180
cttcgcggcc ccgccgtccc ggcagatccc tgatgcccca agtgggcggc cactccatca    240
aagaaccccg gcctgtggca gatctcgtag gcataccgag gttccgcagt gcccccacc     299
```

<210> SEQ ID NO 74
<211> LENGTH: 300
<212> TYPE: DNA
<213> ORGANISM: Methylobacterium

<400> SEQUENCE: 74

```
accgaaggcg tccccggaca cgaaggcctg aaacaccata tctgtggcga tcaggccgac     60
gtggtcgcgg acttcaactg gcagagaatg ccaggccgct tcgatttcag atgatactgg    120
tacggacata ggagcggctt agctttctca gtgcaaatgt gattgattcc ggctcaaaaa    180
tgatcttgat cggacgagac gttttcaatc catgtcgtgt tgccatcgcc gatcggtgcg    240
tcaagagaca gatggcgccg accgtagata cgcgttcggg ttgcccgcac cgcttctcca    300
```

<210> SEQ ID NO 75
<211> LENGTH: 300
<212> TYPE: DNA
<213> ORGANISM: Methylobacterium

<400> SEQUENCE: 75

```
ggaggtgtga tctgatgatg tgctggatga aattggcggt cgagcacttg ttcagcttgg     60
ccagctcgac gagatcggcg tgatgctcgg cgtcgatcag gatgttcagc gagaccggac    120
gtacgcagga cttggtatta gcgccgttgc gcatcagctt gcagccttgc tctgcttctc    180
agcgtgccgc gtcaggatga ccctgatgta gctgttgagg ttgatgccgt aatagcctgc    240
ggactctgtg agatcccggc gaagatcgtc ggcgagggtc aggcggatgg tgctggtcgg    300
```

<210> SEQ ID NO 76
<211> LENGTH: 300
<212> TYPE: DNA
<213> ORGANISM: Methylobacterium

<400> SEQUENCE: 76

```
aagtaaccgc tcaacatgat cttcagcatg ttgtccaaca gcaggagaat acatgtaatt     60
caccatgacc ggcaagctgc gactggccat tgcttccacc gcttgaatgt agcgatcgaa    120
tttcgcaaaa tcagggtgga atgaaaatat cgaaccaaac tgcgagcctt gaatccgttc    180
tgcaaaatta tcgaaaaatt ttcttggccg actgccgttc gaaaacattc ttacgtttac    240
atgcggcccg cctgaaacaa gacagtctac cagctctggg aaatgggggt gaagggtcgg    300
```

METHODS FOR OBTAINING AND USING PLANTS AND PLANT PARTS WITH INCREASED NUTRIENT, OIL, AND/OR PROTEIN CONTENT

CROSS-REFERENCE TO RELATED APPLICATIONS

This patent application is a U.S. national phase application claiming priority to PCT/US2019/064033, filed Dec. 2, 2019, which claims the benefit of U.S. 62/774,640, filed Dec. 3, 2018, U.S. 62/802,038, filed Feb. 6, 2019, U.S. 62/846,247, filed May 10, 2019, U.S. 62/878,164, filed Jul. 24, 2019, and U.S. 62/900,766, filed Sep. 16, 2019, which are each incorporated herein by reference in their entireties.

SEQUENCE LISTING STATEMENT

A sequence listing containing the file named "53907_192969_ST25.txt" which is 23076 bytes (measured in MS-Windows®) and created on Dec. 2, 2019, contains 76 nucleotide sequences, is provided herewith via the USPTO's EFS system, and is incorporated herein by reference in its entirety.

BACKGROUND

Plant seeds are an important source of oil for use in food, feed, and other industrial applications. Such oil can be obtained from plant seeds by a variety of methods including expelling and/or solvent extraction. Provision of seeds with increased oil content is anticipated to provide for improved oil yield in oil production processes where plant seed are used as feedstock. Provision of seeds with increased oil content is also anticipated to provide seeds that can be used in either a whole or processed form to provide food ingredients, feed ingredients, food, or feed with increased oil content.

Plant seeds are also an important source of protein for use in food, feed, and other industrial applications. Such protein can be obtained from plant seeds by a variety of methods including extraction of defatted seed meal with water or other aqueous solvents. Provision of seeds with increased protein content is anticipated to provide for improved protein yield production processes where plant seeds are used as feedstock. Provision of seeds with increased protein content is also anticipated to provide seeds that can be used in either a whole or processed form to provide food ingredients, feed ingredients, food, or feed with increased protein content.

Plants require certain macronutrients and micronutrients for growth and metabolism. These elements are generally found in the soil as salts and can be consumed by plants as ions. In agriculture, soil can become depleted of one or more of these nutrients requiring the addition of fertilizers to provide sufficient quantities of the nutrients for crop growth. Plants with such macronutrients and micronutrients can also be a source of such nutrients in human and animal diets. Thus, methods of increasing levels of macronutrients and micronutrients in plants are desired for benefits to agricultural practices and to human and animal nutrition.

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum,* and *Methylocella* (Lidstrom, 2006). Methanotrophs possess the enzyme methane monooxygenase which incorporates an atom of oxygen from $O_2$ into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter,* and *Nocardia* (Lidstrom, 2006).

Some methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M chloromethanicum, M dichloromethanicum, M extorquens, M fujisawaense, M mesophilicum, M organophilum, M radiotolerans, M rhodesianum, M rhodinum, M thiocyanatum,* and *M. zatmanii*. However, *M. nodulans* is a nitrogen-fixing *Methylobacterium* that is not a PPFM (Sy et al., 2001). *Methylobacterium* are found in soil, dust, fresh water, sediments, and leaf surfaces, as well as in industrial and clinical environments (Green, 2006).

*Methylobacterium* strains that can be applied to a variety of crops including corn and soybean to improve seed yield have been reported in US Patent Application Publication Nos. 20160295868 and 20160302423, respectively.

SUMMARY

Methods for identifying a *Methylobacterium* strain that increases mineral nutrient, vitamin, crude fat, seed oil, and/or protein content comprising: (i) treating a seed and/or a plant with at least a first *Methylobacterium* strain to obtain a treated seed and/or a treated plant; (ii) harvesting progeny seed from a mature treated plant, wherein the mature treated plant is grown from the treated seed or treated plant of step (i); (ii) harvesting progeny seed from a mature control plant wherein the mature control plant was grown from an untreated control seed or untreated control plant; (iii) determining mineral nutrient, vitamin, oil and/or protein content in the progeny seed from the mature treated plant and from the mature control plant; and, (iv) selecting a *Methylobacterium* strain that increases the content of one or more mineral nutrients and/or vitamins, and/or the content of crude fat, seed oil, and/or protein of the progeny seed from the mature treated plant in comparison to the mineral nutrient, vitamin, crude fat, seed oil, and/or protein from the progeny seed from the mature control plant are provided.

Methods of identifying a *Methylobacterium* strain that increases mineral nutrient, vitamin, crude fat, seed oil, and/or protein content comprising: (i) treating a first seed or plant part with at least a first *Methylobacterium* strain and a second seed or plant part with a second *Methylobacterium* strain, (ii) planting a control seed or plant part, the first seed or plant part, and the second seed or plant part, wherein the control seed or plant part is not treated with the first *Methylobacterium* strain or the second *Methylobacterium* strain; (iii) harvesting one or more progeny seed from a plant grown from the first seed or plant part, from the plant grown from the second seed or plant part, and from the plant grown from the control seed or plant part; (iv) analyzing the progeny seed harvested from the plant grown from the first seed or plant part, from the plant grown from the second seed or plant part, and from the plant grown from the control seed or plant part for mineral nutrient, vitamin, oil and/or protein content; and (v) selecting the *Methylobacterium* strain that provides progeny seed with the greatest increases in mineral nutrient, vitamin, oil and/or protein content in comparison to progeny seed from the plant grown from the control seed, wherein the *Methylobacterium* strain is either the first *Methylobacterium* strain or the second *Methylobacterium* strain are provided.

Methods of producing a food or feed ingredient with increased mineral nutrient, vitamin, crude fat, oil and/or protein content comprising dehulling, delinting, crushing, macerating, grinding, and/or extracting a seed lot wherein at least 50%, 70%, 80%, 90%, or 95% of the seeds in the seed lot were harvested from mature plants grown from seeds and/or plants treated with an effective amount of a *Methylobacterium* strain, thereby obtaining a food or feed ingredient with increased oil and/or protein content are provided. In certain embodiments of such methods, the *Methylobacterium* is ISO10 (NRRL B-50938) or ISO20 (NRRL B-67743). In certain embodiments, the *Methylobacterium* has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

Methods of producing a food or feed with increased mineral nutrient, vitamin, crude fat, oil and/or protein content comprising incorporating into the food or feed a processed or unprocessed food ingredient obtained from a seed lot wherein at least 50%, 70%, 80%, 90%, or 95% of the seeds in the seed lot were harvested from mature plants grown from seeds and/or plants treated with an effective amount of a *Methylobacterium* strain, thereby obtaining a food or feed with increased mineral nutrient, vitamin, oil and/or protein content are provided. In certain embodiments of such methods, the *Methylobacterium* strain is ISO10 (NRRL B-50938) or ISO20 (NRRL B-67743). In certain embodiments, the *Methylobacterium* strain has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* strain has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

Methods of improving seed oil yield from a seed lot comprising separating an oil-enriched fraction from a seed lot wherein at least 50%, 70%, 80%, 90%, or 95% of the seeds in the seed lot were harvested from mature plants grown from seeds and/or plants treated with an effective amount of a *Methylobacterium* strain are provided. In certain embodiments of such methods, the *Methylobacterium* strain is ISO10 (NRRL B-50938) or ISO20 (NRRL B-67743). In certain embodiments, the *Methylobacterium* strain has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* strain has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

Methods of improving seed protein yield from a seed lot comprising: (i) obtaining a seed lot wherein at least 50%, 70%, 80%, 90%, or 95% of the seed in the seed lot were harvested from mature plants grown from seeds and/or plants treated with an effective amount of a *Methylobacterium* strain; and (ii) separating a protein-enriched fraction from the seed lot are provided. In certain embodiments of such methods, the *Methylobacterium* strain is ISO10 (NRRL B-50938) or ISO20 (NRRL B-67743). In certain embodiments, the *Methylobacterium* strain has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* strain has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

Methods of improving seed protein yield from a seed lot comprising separating a protein-enriched fraction from a seed lot wherein at least 50%, 70%, 80%, 90%, or 95% of the seed in the seed lot were harvested from mature plants grown from seeds and/or plants treated with an effective amount of a *Methylobacterium* strain are provided. In certain embodiments of such methods, the *Methylobacterium* strain is ISO10 (NRRL B-50938) or ISO20 (NRRL B-67743). In certain embodiments, the *Methylobacterium* strain has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* strain has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

Methods of providing a seed lot with increased crude fat, oil, and/or protein content comprising harvesting a seed lot from mature plants grown from seeds and/or plants treated with an effective amount of a *Methylobacterium* strain, wherein at least 95% of the seeds in the harvested seed lot are obtained from the mature plants, wherein the harvested seed lot is packaged, contained or otherwise segregated from seed obtained from untreated plants are provided. In certain embodiments of such methods, the *Methylobacterium* strain is ISO10 (NRRL B-50938) or ISO20 (NRRL B-67743). In certain embodiments, the *Methylobacterium* strain has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* strain has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

Methods for identifying a *Methylobacterium* strain that increases the content of at least one mineral nutrient and/or at least one vitamin in a plant or plant part comprising: (i) treating a seed and/or a plant with at least a first *Methylobacterium* strain to obtain a treated seed and/or a treated plant; (ii) harvesting a plant part from a cultivated plant wherein the cultivated plant is grown from the treated seed or treated plant of step (i); (ii) harvesting a plant part from a cultivated control plant wherein the cultivated control plant was grown from an untreated control seed or untreated control plant; (iii) determining the content of at least one mineral nutrient and/or vitamin in the plant part from the cultivated plant and from the cultivated control plant; and, (iv) selecting a *Methylobacterium* strain that increases the content of at least one mineral nutrient or vitamin in the cultivated plant or a plant part of the cultivated plant in comparison to the content of the at least one mineral nutrient or vitamin in the cultivated control plant or plant part are provided.

Methods of identifying a *Methylobacterium* strain that increases the content of at least one mineral nutrient or vitamin in a plant or plant part comprising: (i) treating a first seed or plant with at least a first *Methylobacterium* strain and a second seed or plant part with a second *Methylobacterium* strain, (ii) harvesting a plant part from a plant grown from the first seed or plant, from a plant grown from the second seed or plant, and from a plant grown from a control seed or from a control plant; (iii) analyzing a plant part harvested from the plant grown from the first seed or plant, from the plant grown from the second seed or plant, and from the plant grown from the control seed or plant to determine the content of at least one mineral nutrient and/or vitamin, and (iv) selecting the *Methylobacterium* strain that provides the greatest increases in the content of the at least one mineral nutrient and/or vitamin in comparison to a plant part from the plant grown from the control seed, wherein the selected *Methylobacterium* strain is either the first *Methylobacterium* strain or the second *Methylobacterium* strain are provided.

Methods of producing a food or feed with increased mineral nutrient, vitamin, crude fat, oil and/or protein content comprising incorporating into the food or feed a processed or unprocessed food ingredient obtained from a cultivated plant or plants grown from *Methylobacterium*-treated seeds, plants or plant parts, thereby obtaining a food or feed with increased mineral nutrient, vitamin, oil and/or protein content are provided. In certain embodiments of such methods, the *Methylobacterium* strain is ISO10 (NRRL B-50938) or ISO20 (NRRL B-67743). In certain embodiments, the *Methylobacterium* strain has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* strain has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

A plant, or plant part having increased mineral nutrient, crude fat, seed oil, and/or protein content, wherein said plant or plant part is harvested from a cultivated plant grown from a *Methylobacterium*-treated seed, plant or plant part, wherein said *Methylobacterium* provides for increased mineral nutrient, crude fat, seed oil, and/or protein content. In certain embodiments, the *Methylobacterium* is ISO10 (NRRL B-50938) or ISO20 (NRRL B-67743). In certain embodiments, the *Methylobacterium* has chromosomal genomic DNA having at least 99%, 99.9, 99.8, 99.7, 99.6%, or 99.5% sequence identity to chromosomal genomic DNA of ISO10 (NRRL B-50938) or ISO20 (NRRL B-67743). In certain embodiments, the *Methylobacterium* has genomic DNA comprising one or more polynucleotide marker fragments of at least 50, 60, 100, 120, 180, 200, 240, or 300 nucleotides of SEQ ID NOS: 25-27 or SEQ ID NOS: 71-73.

BRIEF DESCRIPTION OF THE DRAWINGS/FIGURES

FIG. 1 is a schematic diagram of canola or rapeseed processing methods (Image by Heuzé V., AFZ; from Heuzé V., Tran G., Sauvant D., Lessire M., Lebas F., 2018. *Rapeseed meal*. Feedipedia, a program by INRA, CIRAD, AFZ and FAO. Published on the world wide web site "feedipedia.org/node/52").

FIG. 2 is a schematic diagram of soybean seed processing methods (Image by Tran, H., and Heuzé V., AFZ; from Heuzé V., Tran G., Kaushik S., 2017. *Soybean meal*. Feedipedia, a program by INRA, CIRAD, AFZ and FAO. Published on the world wide web site "feedipedia.org/node/674").

DETAILED DESCRIPTION

Definitions

Figure 1:
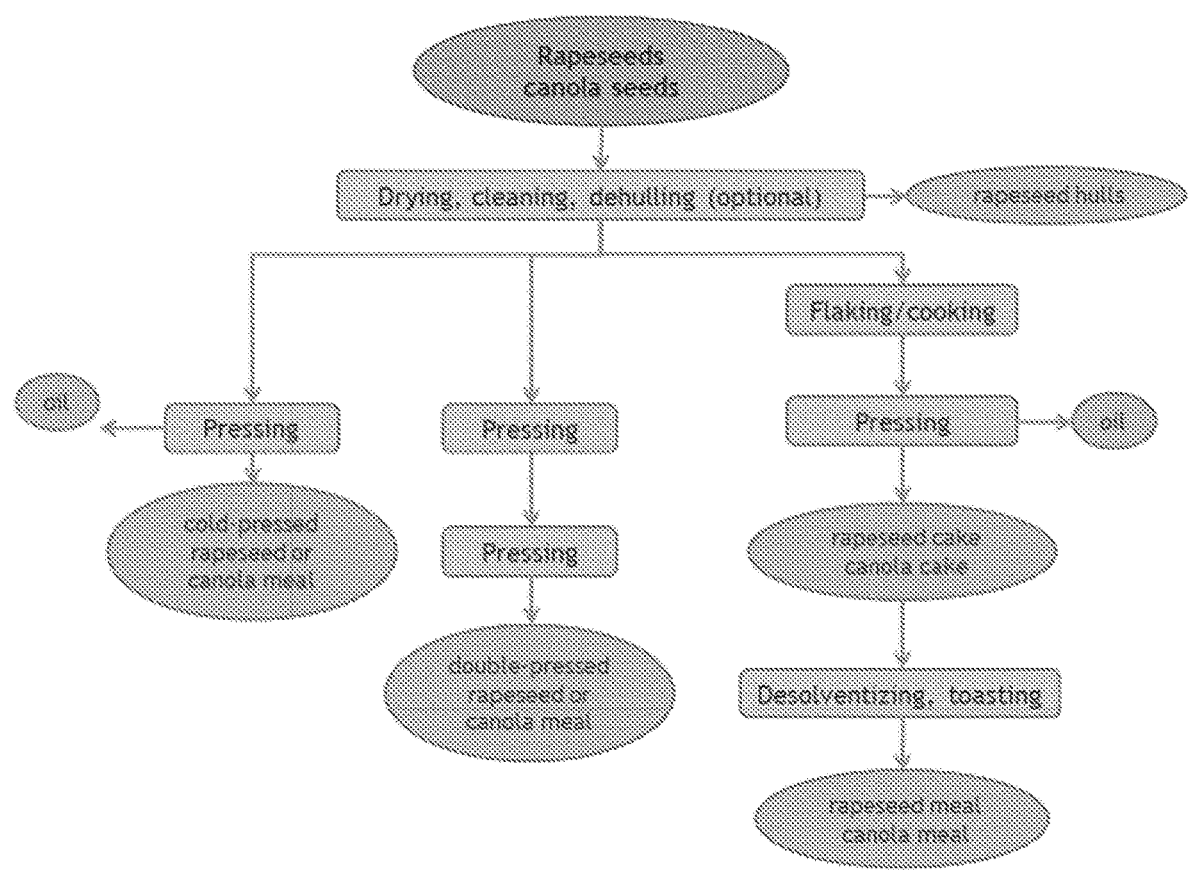
Figure 2:
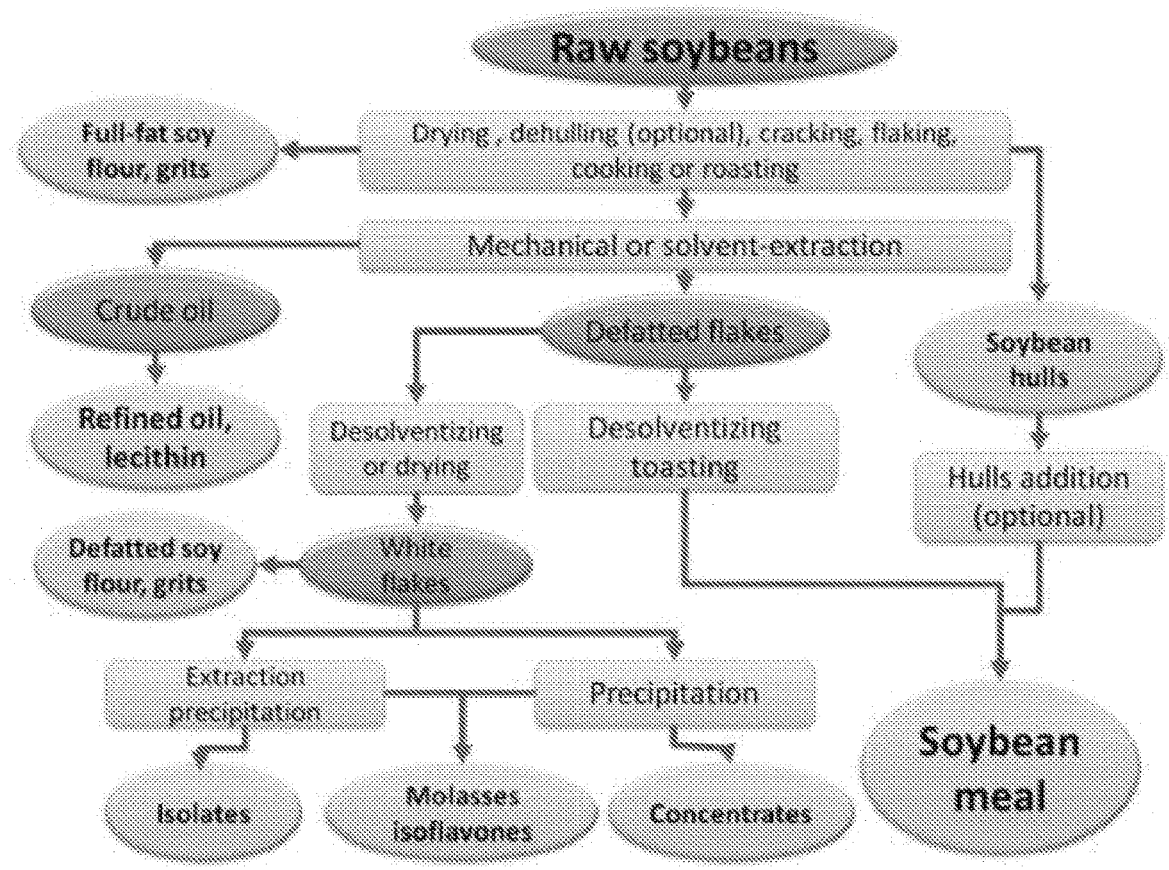

The term "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "include," "includes," and "including" are to be construed as at least having the features or encompassing the items to which they refer while not excluding any additional unspecified features or unspecified items.

As used herein, the term "biological" refers to a component of a composition for treatment of plants or plant parts comprised of or derived from a microorganism. Biologicals include biocontrol agents, other beneficial microorganisms, microbial extracts, natural products, plant growth activators or plant defense agents. Non-limiting examples of biocontrol agents include bacteria, fungi, beneficial nematodes, and viruses. In certain compositions, a biological can comprise a mono-culture or co-culture of *Methylobacterium*, or a combination of *Methylobacterium* strains or isolates that have been separately cultured.

As used herein, the term "*Methylobacterium*" refers to genera and species in the methylobacteriaceae family, including bacterial species in the *Methylobacterium* genus and proposed *Methylorubrum* genus (Green and Ardley (2018)). *Methylobacterium* includes pink-pigmented facultative methylotrophic bacteria (PPFM) and also encompasses the non-pink-pigmented *Methylobacterium nodulans*, as well as colorless mutants of *Methylobacterium* isolates. For example, and not by way of limitation, "*Methylobacterium*" refers to bacteria of the species listed below as well as any new *Methylobacterium* species that have not yet been reported or described that can be characterized as *Methylobacterium* or *Methylorubrum* based on phylogenetic analysis: *Methylobacterium* adhaesivum; *Methylobacterium* oryzae; *Methylobacterium* aerolatum; *Methylobacterium* oxalidis; *Methylobacterium* aquaticum; *Methylobacterium* persicinum; *Methylobacterium* brachiatum; *Methylobacterium* phyllosphaerae; *Methylobacterium* brachythecii; *Methylobacterium* phyllostachyos; *Methylobacterium* bullatum; *Methylobacterium* platani; *Methylobacterium* cerastii; *Methylobacterium* pseudosasicola; *Methylobacterium* currus; *Methylobacterium* radiotolerans; *Methylobacterium* dankookense; *Methylobacterium* soli; *Methylobacterium* frigidaeris; *Methylobacterium* specialis; *Methylobacterium* fujisawaense; *Methylobacterium* tardum; *Methylobacterium* gnaphalii; *Methylobacterium* tarhaniae; *Methylobacterium* goesingense; *Methylobacterium* thuringiense; *Methylobacterium* gossipiicola; *Methylobacterium* trifolii; *Methylobacterium* gregans; *Methylobacterium* variabile; *Methylobacterium* haplocladii; *Methylobacterium* aminovorans (*Methylorubrum aminovorans*); *Methylobacterium* hispanicum; *Methylobacterium* extorquens (*Methylorubrum extorquens*); *Methylobacterium* indicum; *Methylobacterium* podarium (*Methylorubrum podarium*); *Methylobacterium* iners; *Methylobacterium* populi (*Methylorubrum populi*); *Methylobacterium* isbiliense; *Methylobacterium* pseudosasae (*Methylorubrum pseudosasae*); *Methylobacterium* jeotgali; *Methylobacterium rhodesianum* (*Methylorubrum rhodesianum*); *Methylobacterium* komagatae; *Methylobacterium rhodinum* (*Methylorubrum rhodinum*); *Methylobacterium* longum; *Methylobacterium salsuginis* (*Methylorubrum salsuginis*); *Methylobacterium* marchantiae; *Methylobacterium suomiense* (*Methylorubrum suomiense; Methylobacterium* mesophilicum; *Methylobacterium thiocyanatum* (*Methylorubrum thiocyanatum*); *Methylobacterium nodulans*; *Methylobacterium zatmanii* (*Methylorubrum zatmanii*); or *Methylobacterium* organophilum.

As used herein, the phrase "crude fat" refers to a diethyl ether extractable components of a given material (e.g., seed, seed meal, food or feed). Crude fat may include, but not limited to, true fats and oils, fatty acid esters, compound lipids, fat-soluble vitamins and provitamins (e.g., carotenoids), waxes, resins, and essential oils.

As used herein, the phrase "oil content" as applied to a seed or any processed product or fraction thereof refers to the fraction or percentage of the total mass or weight of the seed, processed product, or fraction thereof that is oil. Oil content can be expressed as a percentage of the total dry or weight of the seed, processed product, or fraction thereof.

As used herein, the term "oil" or phrase "seed oil" refers to the combination of triglycerides comprising saturated and/or unsaturated fatty acids, free saturated fatty acids, and free unsaturated fatty acids. Such fatty acids can include alpha-linolenic acid (C-18:3), linoleic acid (C-18:2), oleic acid (C-18:1), stearic acid (C-18:0), heptadecanoic (C-17:0), and/or palmitic acid (C-16:0).

As used herein, the terms "include," "includes," and "including" are to be construed as at least having the features to which they refer while not excluding any additional unspecified features.

As used herein, the phrase "protein content" as applied to a seed or any processed product or fraction thereof refers to the fraction or percentage of the total mass or weight of the seed, processed product, or fraction thereof that is protein. Protein content can be expressed as a percentage of the total dry or wet weight of the seed, processed product, or fraction thereof. Protein content can also be expressed as mass units of protein per mass units seed, processed product, or fraction thereof (e.g., grams protein per kilogram dry or wet weight of the seed, processed product, or fraction thereof).

As used herein "mineral nutrients" are micronutrients or macronutrients required or useful for plants or plant parts including for example, but not limited to, nitrogen (N), potassium (K), calcium (Ca), magnesium (Mg), phosphorus (P), and sulfur (S), and the micronutrients chlorine (Cl), Iron (Fe), Boron (B), manganese (Mn), zinc (Z), copper (Cu), molybdenum (Mo) and nickel (Ni).

As used herein, "vitamins" are organic compounds required in small amounts for normal growth and metabolism. Vitamins are important for human and/or animal growth and some vitamins have been reported to be beneficial to plants. Vitamins include but are not limited to vitamin A (including but not limited to all-trans-retinol, all-trans-retinyl-esters, as well as all-trans-beta-carotene and other provitamin A carotenoids), vitamin B1(thiamine), vitamin B2 (riboflavin), vitamin B3 (niacin), vitamin B5(pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones).

As used herein, the phrase "seed lot" refers to a collection of two or more seeds from one or more plants. In certain embodiments, a seed lot includes a collection of more than 10, 50, 100, 500, 1000 or more seeds from one or more plants.

As used herein, the term "strain" shall include all isolates of such strain.

As used herein, "variant" when used in the context of a *Methylobacterium* isolate, refers to any isolate that has chromosomal genomic DNA with at least 99%, 99.9, 99.8, 99.7, 99.6%, or 99.5% sequence identity to chromosomal genomic DNA of a reference *Methylobacterium* isolate, such as, for example, a deposited *Methylobacterium* isolate provided herein. A variant of an isolate can be obtained from various sources including soil, plants or plant material, and water, particularly water associated with plants and/or agriculture. Variants include derivatives obtained from deposited isolates. *Methylobacterium* isolates or strains can be sequenced (for example as taught by Sanger et al. (1977), Bentley et al. (2008) or Caporaso et al. (2012)) and genome-scale comparison of the sequences conducted (Konstantinos et al. (2005)) using sequence analysis tools (for example, BLAST, as taught by Altschul et al. (1990)).

As used herein, "derivative" when used in the context of a *Methylobacterium* isolate, refers to any *Methylobacterium* that is obtained from a deposited *Methylobacterium* isolate provided herein. Derivatives of a *Methylobacterium* isolate include, but are not limited to, derivatives obtained by selection, derivatives selected by mutagenesis and selection, and genetically transformed *Methylobacterium* obtained from a *Methylobacterium* isolate. A "derivative" can be identified, for example based on genetic identity to the strain or isolate from which it was obtained and will generally exhibit chromosomal genomic DNA with at least 99%, 99.9, 99.8, 99.7, 99.6%, or 99.5% sequence identity to chromosomal genomic DNA of the strain or isolate from which it was derived.

As used herein, the term "cultivate" means to grow a plant. A cultivated plant can be one grown and raised on a large agricultural scale or on a smaller scale, including for example a single plant.

Where a term is provided in the singular, other embodiments described by the plural of that term are also provided.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

FURTHER DESCRIPTION

Various methods where *Methylobacterium* strains are used to increase the mineral nutrient, vitamin, oil and/or protein content in plants or plant parts harvested from plants grown from seed and/or plants comprising plant parts treated with the *Methylobacterium* are provided herein. In certain embodiments, *Methylobacterium* treatment of soil, a seed, a leaf, a fruit, a stem, a root, or a shoot can increase plant mineral nutrient, vitamin, crude fat, seed oil, and/or protein content in seeds or seed lots harvested from plants grown from the treated seed or plant comprising the treated plant part. In other embodiments, *Methylobacterium* treatment of soil, a seed, a leaf, a fruit, a stem, a root, or a shoot can increase the content of one or more mineral nutrients or vitamins in harvested plants or plant parts from plants grown from the *Methylobacterium*-treated plant parts or *Methylobacterium*-treated seeds provided herein. *Methylobacterium* soil treatments or applications can include, but are not limited to, in-furrow applications (e.g., before, during, and/or after seed deposition), soil drenches, distribution of granular or other dried formulations to the soil (e.g., before, during, and/or after seed deposition or plant growth). In certain embodiments, *Methylobacterium* treatment of a seed and/or plant can thus comprise any *Methylobacterium* soil treatment or application where the seed and/or plant is contacted and/or colonized by the *Methylobacterium*. Treatments or applications can include, but are not limited to, spraying, coating, partially coating, immersing, and/or imbibing the plant or plant parts with the *Methylobacterium* strains and compositions comprising the same provided herein. In certain embodiments, soil, a seed, a leaf, a fruit, a stem, a root, a tuber, or a shoot can be sprayed, immersed and/or imbibed with a liquid, semi-liquid, emulsion, or slurry of a composition provided herein. Such seed immersion or imbibition can be sufficient to provide for increased crude fat, seed oil, and/or protein content in a treated plant or plant grown from a treated seed in comparison to an untreated plant or plant grown from an untreated seed. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation. Seed treatments can be effected with both continuous and/or a batch seed treaters. In certain embodiments, the coated seeds can be prepared by slurrying seeds with a coating composition comprising a *Methylobacterium* strain that increases mineral nutrient, vitamin, crude fat, seed oil, and/or protein content and air-drying the resulting product. Air-drying can be accomplished at any temperature that is not deleterious to the seed or the *Methylobacterium*, but will typically not be greater than 30 degrees Centigrade. The proportion of coating that comprises the *Methylobacterium* strain includes, but is not limited to, a range of 0.1 to 25% by weight of the seed or other plant part, 0.5 to 5% by weight of the seed or other plant part, and 0.5 to 2.5% by weight of the seed or other plant part. In certain embodiments, a solid substance used in the seed coating or treatment will have a *Methylobacterium* strain that increases mineral nutrient, vitamin, crude fat, seed oil, and/or protein content adhered to a solid substance by being grown in biphasic media comprising the *Methylobacterium* strain, solid substance, and liquid media. Methods for growing *Methylobacterium* in biphasic media include those described in U.S. Pat. No. 9,181,541, which is specifically incorporated herein in its entirety. In certain embodiments, compositions suitable for treatment of a seed or plant part with a *Methylobacterium* strain that increases mineral nutrient, vitamin, crude fat, seed oil, and/or protein content can be obtained by the methods provided in US Patent Application No. US 20160120188, which is specifically incorporated herein in its entirety. Various seed treatment compositions and methods for seed treatment disclosed in U.S. Pat. Nos. 5,106,648, 5,512,069, and 8,181,388 are incorporated herein by reference in their entireties and can be adapted for treating seeds with compositions comprising a *Methylobacterium* strain.

In certain embodiments, the composition used to treat the seed or plant part can contain a *Methylobacterium* strain and an agriculturally acceptable excipient. Agriculturally acceptable excipients include, but are not limited to, woodflours, clays, activated carbon, diatomaceous earth, fine-grain inorganic solids, calcium carbonate and the like. Clays and inorganic solids that can be used with the include, but are not limited to, calcium bentonite, kaolin, china clay, talc, perlite, mica, vermiculite, silicas, quartz powder, montmorillonite and mixtures thereof.

Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with compositions comprising a suitable *Methylobacterium* strain. In certain embodiments, the seed and/or seedling is exposed to the composition by providing the *Methylobacterium* strain in soil in which the plant or a plant arising from the seed are grown, or other plant growth media in which the plant or a plant arising from the seed are grown. Examples of methods where the *Methylobacterium* strain is provided in the soil include in furrow applications, soil drenches, and the like.

In certain embodiments, a *Methylobacterium* strain that increases mineral nutrient, vitamin, crude fat, seed oil, and/or protein content used to treat a given species of seed or plant part can be a *Methylobacterium* strain that was isolated from a different plant species and is thus heterologous to the treated plant or plant part. Non-limiting examples of treatments of plant seed or other plant parts with a heterologous *Methylobacterium* include treatments of soybean, *Brassica* sp., sunflower, cotton, flax, or peanut seeds and parts with a *Methylobacterium* strain that was isolated from a plant other than a soybean, *Brassica* sp., sunflower, cotton, flax, or peanut plant, respectively.

Non-limiting examples of treatments of plant seed or other plant parts with a *Methylobacterium* providing for increased content of one or more mineral nutrients, vitamins, crude fat, seed oil, and/or protein in a harvested plant part include treatments of corn, soybean, *Brassica* sp. (e.g., *B. napus, B. rapa, B. juncea*), alfalfa, rice, rye, wheat, barley, oats, sorghum, millet (e.g. pearl millet (*Pennisetum glaucum*)), proso millet (*Panicum miliaceum*), foxtail millet (*Setaria italica*) finger millet (*Eleuisine corocana*), sunflower, safflower, tobacco, potato, peanuts, cotton, species in the genus *Cannabis* including, but not limited to, *Cannabis sativa* and industrial hemp varieties, sweet potato (*Ipomoea botatus*), cassava, coffee, coconut, pineapple, citrus trees, cocoa, tea, date palm, banana, apple, pear, grape, berry plants (including, but not limited to blackberry, raspberry, strawberry or blueberry plants), avocado, fig, guava, kiwi, mango, olive, *papaya*, cashew, macadamia, almond, sugar beets, sugarcane, tomatoes, peppers, carrots, celery, lettuce green beans, lima beans, peas, lentils, cucurbits (including, but not limited to cucumber, cantaloupe, melons, squash, pumpkin, and zucchini). In other embodiments, treated plants include ornamentals (including, but not limited to, azalea, *hydrangea*, hibiscus, roses, tulips, daffodils, petunias, canation, poinsettia, and chrysanthemum), conifers (including, but not limited to pines such as loblolly pine, slash pine. *ponderosa* pine lodge pole pine, and Monterey pine; Douglas-fir: Western hemlock: Sitka spruce: redwood true firs such as silver fir and balsam fir; and cedars such as Western red cedar and Alaska yellow-cedar) and turfgrass (including, but are not limited to, annual bluegrass, annual ryegrass, Canada bluegrass, fescue, bentgrass, wheatgrass. Kentucky bluegrass, orchard grass, ryegrass, redtop, Bermuda grass, St. Augustine grass, and *zoysia* grass). In certain embodiments, a *Methylobacterium* strain that increases mineral nutrient, vitamin, crude fat, seed oil, and/or protein content used to treat a given cultivar or variety of seed, plant or plant part can be a *Methylobacterium* strain that was isolated from a different plant species, or a different cultivar or variety of the plant species being treated, and is thus non-resident to the treated plant or plant part.

Plant parts that have increased levels of one or more mineral nutrients, vitamins, crude fat, seed oil, and/or protein as the result of treatment with *Methylobacterium* as provided herein include, but are not limited to, leaves, stems, flowers, roots, seeds, fruit, tubers, coleoptiles, and the like.

In some embodiments, a plant part having increased levels of one or more mineral nutrients, vitamins, crude fat, seed oil, and/or protein is a plant seed. Of particular interest for treatments of plant seed or other plant parts with *Methylobacterium* providing for increases in mineral nutrients, vitamins, crude fat, seed oil, and/or protein in harvested plant seeds are treatments of soybean, *Brassica* sp., sunflower, cotton, flax, or peanut seeds and parts. In some embodiments, such treatments are with a *Methylobacterium* strain that was isolated from a different species, cultivar or variety compared to the plant being treated.

In certain embodiments, a manufactured combination composition comprising two or more *Methylobacterium* strains can be used to treat a seed or plant part in any of the methods provided herein. Such manufactured combination compositions can be made by methods that include harvesting monocultures of each *Methylobacterium* strain and mixing the harvested monocultures to obtain the manufactured combination composition of *Methylobacterium*. In certain embodiments, the manufactured combination composition of *Methylobacterium* can comprise *Methylobacterium* isolated from different plant species or from different cultivars or varieties of a given plant.

In certain embodiments, an effective amount of the *Methylobacterium* strain or strains that increase mineral nutrient, vitamin, crude fat, seed oil, and/or protein content used in treatment of seeds or plant parts is a composition having a *Methylobacterium* titer of at least about $1 \times 10^6$ colony-forming units per milliliter, at least about $5 \times 10^6$ colony-forming units per milliliter, at least about $1 \times 10^7$ colony-forming units per milliliter, at least about $5 \times 10^8$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, an effective amount of the *Methylobacterium* strain or strains that increase mineral nutrient, vitamin, crude fat, seed oil, and/or protein content used in treatment of seeds or plant parts is a composition with the *Methylobacterium* at a titer of about least about $1 \times 10^6$ colony-forming units per milliliter, at least about $5 \times 10^6$ colony-forming units per milliliter, at least about $1 \times 10^7$ colony-forming units per milliliter, or at least about $5 \times 10^8$ colony-forming units per milliliter to at least about $6 \times 10^{10}$ colony-forming units per milliliter of a liquid or an emulsion. In certain embodiments, an effective amount of the *Methylobacterium* strain or strains that increase mineral nutrient, vitamin, crude fat, seed oil, and/or protein content used in treatment of seeds or plant parts is a composition with the *Methylobacterium* at least about $1 \times 10^6$ colony-forming units per gram, at least about $5 \times 10^6$ colony-forming units per gram, at least about $1 \times 10^7$ colony-forming units per gram, or at least about $5 \times 10^1$ colony-forming units per gram to at least about $6 \times 10^{10}$ colony-forming units of *Methylobacterium* per gram of the composition. In certain embodiments, an effective amount of a composition provided herein that is sufficient to provide for increased mineral nutrient, vitamin, crude fat, seed oil, and/or protein content can be a composition with a *Methylobacterium* titer of at least about $1\times10^6$ colony-forming units per gram, at least about $5\times10^6$ colony-forming units per gram, at least about $1\times10^7$ colony-forming units per gram, or at least about $5\times10^8$ colony-forming units per gram to at least about $6\times10^{10}$ colony-forming units of *Methylobacterium* per gram of particles in the composition containing the particles that comprise a solid substance wherein a mono-culture or co-culture of crude fat, seed oil, and/or protein content enhancing *Methylobacterium* strain or strains is adhered thereto. In certain embodiments, an effective amount of a composition provided herein that is sufficient to provide for increased mineral nutrient, vitamin, crude fat, seed oil, and/or protein content to a plant or plant part can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL in a composition comprising an emulsion wherein a mono-culture or co-culture of a *Methylobacterium* strain or strains that increase mineral nutrient, vitamin, crude fat, seed oil, and/or protein content adhered to a solid substance is provided therein or grown therein. In certain embodiments, an effective amount of a composition provided herein that is sufficient to provide for increased mineral nutrient, vitamin, crude fat, seed oil, and/or protein content to a plant or plant part can be a composition with a *Methylobacterium* titer of at least about $1\times10^6$ colony-forming units per mL, at least about $5\times10^6$ colony-forming units per mL, at least about $1\times10^7$ colony-forming units per mL, or at least about $5\times10^8$ colony-forming units per mL to at least about $6\times10^{10}$ colony-forming units of *Methylobacterium* per mL of in a composition comprising an emulsion wherein a mono-culture or co-culture of a *Methylobacterium* strain or strains that increase mineral nutrient, vitamin, crude fat, seed oil, and/or protein content is provided therein or grown therein. In certain embodiments, any of the aforementioned compositions comprising a mono-culture or co-culture of a *Methylobacterium* strain or strains that increase mineral nutrient, vitamin, crude fat, seed oil, and/or protein content can further comprise a mono- or co-culture of *Rhizobium* and/or *Bradyrhizobium*.

An effective amount of a *Methylobacterium* strain or strains that increase mineral nutrient, vitamin, crude fat, seed oil, and/or protein content provided in a treatment of a seed or plant part is an amount that results in an increase in the mineral nutrient, vitamin, crude fat, seed oil, and/or protein content of seed or other plant parts harvested from a plant grown from the treated seed or plant comprising the treated plant part. In certain embodiments, an effective amount of a *Methylobacterium* strain or strains that increase mineral nutrient, vitamin, crude fat, seed oil, and/or protein content provided in a treatment of a seed or plant part is at least about $10^3$, $10^4$, $10^5$, or $10^6$ CFU per seed or treated plant part. In certain embodiments, an effective amount of *Methylobacterium* provided in a treatment of a seed or plant part is at least about $10^3$, $10^4$, $10^5$, or $10^6$ CFU to about $10^7$, $10^8$, $10^9$, or $10^{10}$ CFU per seed or treated plant part. In certain embodiments, the effective amount of *Methylobacterium* provided in a treatment of a seed or plant part is an amount where the CFU per seed or treated plant part will exceed the number of CFU of any resident naturally occurring *Methylobacterium* strain by at least 5-, 10-, 100-, or 1000-fold. In certain embodiments, the effective amount of *Methylobacterium* provided in a treatment of a seed or plant part is an amount where the CFU per seed or treated plant part will exceed the number of CFU of any resident naturally occurring *Methylobacterium* by at least 2-, 3-, 5-, 8-, 10-, 20-, 50-, 100-, or 1000-fold.

*Methylobacterium* sp, strains are useful in certain methods provided herein. In one embodiment, the *Methylobacterium* strain includes certain *Methylobacterium* strains obtained from *Methylobacterium* species that include *M. gregans, M. komagatae*, and *M. radiotolerans*. Non-limiting examples of other *Methylobacterium* sp, strains of use in certain methods provided herein are disclosed in Table 1. Other *Methylobacterium* sp, strains useful in certain methods provided herein include variants of the *Methylobacterium* sp, strains disclosed in Table 1.

TABLE 1

*Methylobacterium* sp. strain

| Deposit Identifier | Isolate No. | NLS NO. | USDA ARS NRRL No.[1] | Strain Source: Obtained from: |
|---|---|---|---|---|
| *Methylobacterium* sp. #1 | ISO01 | NLS0046 | NRRL B-50929 | a soybean plant grown in Saint Louis County, Missouri, USA |
| *Methylobacterium* sp. #2 | ISO02 | NLS0020 | NRRL B-50930 | a weed grown in Saint Louis County, Missouri, USA |
| *Methylobacterium* sp. #3 | ISO03 | NLS0017 | NRRL B-50931 | a mint plant grown in Saint Louis County, Missouri, USA |
| *Methylobacterium* sp. #4 | ISO04 | NLS0042 | NRRL B-50932 | a soybean plant grown in Saint Louis County, Missouri, USA |
| *Methylobacterium* sp. #5 | ISO05 | NLS0089 | NRRL B-50933 | a broccoli plant grown in Saint Louis County, Missouri, USA |
| *Methylobacterium* sp. #6 | ISO06 | NLS0068 | NRRL B-50934 | a corn plant grown in Saint Louis County, Missouri, USA |
| *Methylobacterium* sp. #7 | ISO07 | NLS0065 | NRRL B-50935 | a corn plant grown in Saint Louis County, Missouri, USA |
| *Methylobacterium* sp. #8 | ISO08 | NLS0069 | NRRL B-50936 | a corn plant grown in Saint Louis County, Missouri, USA |
| *Methylobacterium* sp. #9 | ISO09 | NLS0062 | NRRL B-50937 | a corn plant grown in Saint Louis County, Missouri, USA |
| *Methylobacterium* sp. #10 | ISO10 | NLS0064 | NRRL B-50938 | a corn plant grown in Saint Louis County, Missouri, USA |
| *Methylobacterium* sp. #11 | ISO11 | NLS0021 | NRRL B-50939 | a lettuce plant grown in Saint Louis County, Missouri, USA |

TABLE 1-continued

Methylobacterium sp. strain

| Deposit Identifier | Isolate No. | NLS NO. | USDA ARS NRRL No.[1] | Strain Source: Obtained from: |
|---|---|---|---|---|
| Methylobacterium sp. #12 | ISO12 | NLS0066 | NRRL B-5 0940 | a corn plant grown in Saint Louis County, Missouri, USA |
| Methylobacterium sp. #13 | ISO13 | NLS0037 | NRRL B-50941 | a tomato plant grown in Saint Louis County, Missouri, USA |
| Methylobacterium sp. #14 | ISO14 | NLS0038 | NRRL B-50942 | a tomato plant grown in Saint Louis County, Missouri, USA |
| Methylobacterium #15 | ISO15 | NLS0044 | NRRL B-67339 | a soybean plant grown in Saint Louis County, Missouri, USA |
| Methylobacterium #16 | ISO16 | NLS0109 | NRRL B-67340 | a yucca plant grown in Saint Louis County, Missouri, USA |
| Methylobacterium sp (#18) | ISO18 | NLS0648 | NRRL B-67741 | a Dionaea muscipula plant (Venus fly trap) grown in St. Charles, MO. |
| Methylobacterium sp (#19) | ISO19 | NLS0662 | NRRL B-67742 | an Orchidaceae spp. plant (orchid) grown in Saint Louis County, Missouri, USA |
| Methylobacterium sp (#20) | ISO20 | NLS0807 | NRRL B-67743 | a tomato plant grown in Saint Louis County, Missouri. USA |
| Methylobacterium sp (#26) | ISO26 | NLS0610 | Deposited under Budapest Treaty with the NRRL, Peoria, IL, USA on Nov. 26, 2019; NRRL B-67892 | A Lagerstroemia indica (crape myrtle) plant grown in Saint Louis County, Missouri, USA |

[1]Deposit number for strain deposited with AGRIGULTURAL RESEARCH SERVICE CULTURE COLLECTION (NRRL) of the National Center Agricultural Utilization Research, Agricultural Research Service, U.S. Department of Agriculture, 1815 North University Street, Peoria, Illinois 61604 U.S.A. under the terms of the Budapest Treaty on the International Recoginition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Variants of a Methylobacterium isolate listed in Table 1 include isolates obtained therefrom by genetic transformation, mutagenesis and/or insertion of a heterologous sequence. In some embodiments, such variants are identified by the presence of chromosomal genomic DNA with at least 99%, 99.9, 99.8, 99.7, 99.6%, or 99.5% sequence identity to chromosomal genomic DNA of the strain from which it was derived. In certain embodiments, such variants are distinguished by the presence of one or more unique DNA sequences that include: (i) a unique sequence of SEQ ID NOs: 1 to 3, SEQ ID NOs: 13 to 15, SEQ ID NOs: 25 to 27, SEQ ID NOs: 37 to 39, SEQ ID NOs: 49 to 51, and SEQ ID NOs: 61 to 73; or (ii) sequences with at least 98% or 99% sequence identity across the full length of SEQ ID NOs: 1 to 3, SEQ ID NOs: 13 to 15, SEQ ID NOs: 25 to 27, SEQ ID NOs: 37 to 39, SEQ ID NOs: 49 to 51, SEQ ID NOs: 61 to 73, and SEQ ID Nos:74 to 76.

Co-assigned patent applications disclose additional specific uses of certain Methylobacterium strains of Table 1 such as: increasing corn yield (US20160295868); improving lettuce cultivation (U.S. Pat. No. 10,212,939); improving tomato growth (US20170086464); improving soy yield (US2016/0302423); improving fruit production (U.S. Pat. No. 10,111,438); controlling corn rootworm (US 20170238553); controlling root lesion nematodes (US20170164618); controlling root knot nematodes (U.S. Pat. No. 10,098,353); and controlling fungal disease (US20180295841 and WO2018106899) are each incorporated herein by reference in their entireties. In certain embodiments of the methods provided herein, the Methylobacterium strain or strains used to treat a seed and/or a plant part are selected from the group consisting of ISO01 (NRRL B-50929), ISO02 (NRRL B-50930), ISO03 (NRRL B-50931), ISO04 (NRRL B-50932), ISO05 (NRRL B-50933), ISO06 (NRRL B-50934), ISO07 (NRRL B-50935), ISO08 (NRRL B-50936), ISO09 (NRRL B-50937), ISO10 (NRRL B-50938), ISO11 (NRRL B-50939), ISO12 (NRRL B-50940), ISO13 (NRRL B-50941), ISO14 (NRRL B-50942), ISO16 (NRRL B-67340), ISO18 (NRRL B-67741), ISO19 (NRRL B-67742), ISO20 (NRRL B-67743), variants thereof, or any combination thereof. In certain embodiments, one or more of the Methylobacterium strains used in the methods can comprise total genomic DNA (chromosomal and plasmid DNA) or average nucleotide identity (ANI) with at least 99%, 99.9, 99.8, 99.7, 99.6%, or 99.5% sequence identity or ANI to total genomic DNA of ISO01 (NRRL B-50929), ISO02 (NRRL B-50930), ISO03 (NRRL B-50931), ISO04 (NRRL B-50932), ISO05 (NRRL B-50933), ISO06 (NRRL B-50934), ISO07 (NRRL B-50935), ISO08 (NRRL B-50936), ISO09 (NRRL B-50937), ISO10 (NRRL B-50938), ISO11 (NRRL B-50939), ISO12 (NRRL B-50940), ISO13 (NRRL B-50941), ISO14 (NRRL B-50942), ISO16 (NRRL B-67340), ISO18 (NRRL B-67741), ISO19 (NRRL B-67742), or ISO20 (NRRL B-67743). In certain embodiments, the percent ANI can be determined as disclosed by Konstantinidis et al., 2006. In certain embodiments of the methods provided herein, the Methylobacterium strain or strains used to treat a seed and/or a plant part is not the strain identified as either ISO10 or NLS0064 which was deposited under the NRRL accession No. NRRL B-50938. In certain embodiments of the methods provided herein, the strain identified as either ISO10 or NLS0064 which was deposited under the NRRL accession No. NRRL B-50938 is not used. In certain methods provided herein for identifying Methylobacterium that can improve crude fat, seed oil, and/or protein content, any of the aforementioned strains set forth in Table 1 can be used as a control or reference standard for comparison to one or more new test or candidate Methylobacterium isolates. In certain embodiments, the strain identified as either ISO10 or NLS0064 which was deposited under the NRRL accession No. NRRL B-50938 is used as a control or reference standard for comparison to one or more new test or candidate *Methylobacterium* isolates in a method of identifying a new *Methylobacterium* that can improve crude fat, seed oil, and/or protein content.

In certain embodiments of the methods provided herein, seeds and/or plant parts are treated with both a *Methylobacterium* strain and at least one additional component. In some embodiments an additional component can be an additional active ingredient, for example, a pesticide or a second biological. In certain embodiments, the pesticide can be an insecticide, a fungicide, an herbicide, a nematicide or other biocide. The second biological could be a strain that improves yield or controls an insect, pest, fungi, weed, or nematode.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In particular embodiments insecticides and nematicides include abamectin, aldicarb, aldoxycarb, bifenthrin, carbofuran, chlorantraniliporle, chlothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, tioxazafen, spinetoram, spinosad, spirodichlofen, spirotetramat, tefluthrin, thiacloprid, thiamethoxam, and thiodicarb.

Non-limiting examples of useful fungicides include aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides, and triazoles. Particular examples of fungicides include acibenzolar-S-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole. Non-limiting examples of other biocides, include isothiazolinones, for example 1,2 Benzothiazolin-3-one (BIT), 5-Chloro-2-methyl-4-isothiazolin-3-one (CIT), 2-Methyl-4-isothiazolin-3-one (MIT), octylisothiazolinone (OIT), dichlorooctylisothiazolinone (DCOIT), and butylbenzisothiazolinone (BBIT); 2-Bromo-2-nitro-propane-1,3-diol (Bronopol), 5-bromo-5-nitro-1,3-dioxane (Bronidox), Tris(hydroxymethyl)nitromethane, 2,2-Dibromo-3-nitrilopropionamide (DBNPA), and alkyl dimethyl benzyl ammonium chlorides.

Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins, Particular examples of herbicides include acetochlor, clethodim, dicamba, flumioxazin, fomesafen, glyphosate, glufosinate, mesotrione, quizalofop, saflufenacil, sulcotrione, and 2,4-D.

In some embodiments, the composition or method disclosed herein may comprise a *Methylobacterium* strain and an additional active ingredient selected from the group consisting of clothianidin, ipconazole, imidacloprid, metalaxyl, mefenoxam, tioxazafen, azoxystrobin, thiomethoxam, fluopyram, prothioconazole, pyraclostrobin, and sedaxane.

In some embodiments, the composition or method disclosed herein may comprise an additional active ingredient, which may be a second biological. The second biological could be a biological control agent, other beneficial microorganisms, microbial extracts, natural products, plant growth activators or plant defense agent. Non-limiting examples of the second biological could include bacteria, fungi, beneficial nematodes, and viruses. In certain embodiments, the second biological can be a *Methylobacterium*. In certain embodiments, the second biological is a *Methylobacterium* listed in Table 1. In certain embodiments, the second biological can be a *Methylobacterium* selected from *M. gregans, M radiotolerans, M extorquens, M. populi, M. salsuginis, M brachiatum*, and *M. komagatae*.

In certain embodiments, the second biological can be a bacterium of the genus *Actinomycetes, Agrobacterium, Arthrobacter, Alcaligenes, Aureobacterium, Azobacter, Azorhizobium, Azospirillum, Azotobacter, Beijerinckia, Bacillus, Brevibacillus, Burkholderia, Chromobacterium, Clostridium, Clavibacter, Comomonas, Corynebacterium, Curtobacterium, Enterobacter, Flavobacterium, Gluconacetobacter, Gluconobacter, Herbaspirillum, Hydrogenophage, Klebsiella, Luteibacter, Lysinibacillus, Mesorhizobium, Methylobacterium, Microbacterium, Ochrobactrum, Paenibacillus, Pantoea, Pasteuria, Phingobacterium, Photorhabdus, Phyllobacterium, Pseudomonas, Rhizobium, Rhodococcus, Bradyrhizobium, Serratia, Sinorhizobium, Sphingomonas, Streptomyces, Stenotrophomonas, Variovorax, Xanthomonas* and *Xenorhadbus*. In particular embodiments the bacteria is selected from the group consisting of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Chromobacterium suttsuga, Pasteuria penetrans, Pasteuria usage*, and *Pseudomona fluorescens*.

In certain embodiments, the second biological is a *Rhizobium* or *Bradyrhizobium*, which is beneficial to growth of plants grown from treated seed and/or a plant comprising a treated plant part. Treatments of leguminous plant seeds or other plant parts including soybean and peanut with both a *Methylobacterium* strain or strains and the *Rhizobium* or *Bradyrhizobium* can result in an improvement in crude fat, seed oil, and/or protein content of seed harvested from a plant grown from the treated seed and/or plant parts in comparison to a control plant grown from seed and/or plant parts treated with just the *Rhizobium* or *Bradyrhizobium* (i.e., not treated with the *Methylobacterium*) and/or to a control plant grown from seed and/or plant parts that were not treated with a *Methylobacterium* strain and that were not treated with the *Rhizobium* or *Bradyrhizobium*.

In certain embodiments the second biological can be a fungus of the genus *Acremonium, Alternaria, Ampelomyces, Aspergillus, Aureobasidium, Beauveria, Botryosphaeria, Cladosporium, Cochliobolus, Colletotrichum, Coniothyrium, Embellisia, Epicoccum, Fusarium, Gigaspora, Gliocladium, Glomus, Laccaria, Metarhisium, Muscodor, Nigrospora, Paecilonyces, Paraglomus, Penicillium, Phoma, Pisolithus, Podospora, Rhizopogon, Scleroderma, Trichoderma, Typhula, Ulocladium*, and *Verticilium*. In particular embodiments, the fungus is *Beauveria bassiana, Coniothyrium minitans, Gliocladium vixens, Muscodor albus, Paecilomyces lilacinus*, or *Trichoderma polysporum*.

In further embodiments the second biological can be plant growth activators or plant defense agents including, but not limited to harpin, *Reynoutria sachalinensis*, jasmonate, lipochitooligosaccharides, and isoflavones.

In further embodiments, the second biological can include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma virens*, and *Streptomyces lydicus* strains. Other microorganisms that are added can be genetically engineered or wild-type isolates that are available as pure cultures. In certain embodiments, it is anticipated that the second biological can be provided in the composition in the form of a spore.

Seed lots comprising at least about 50%, 70%, 80%, 90%, 95%, 98%, or 99% of seeds harvested from mature plants grown from seeds and/or plants treated with an effective amount of a *Methylobacterium* strain or strains are provided herein. Such seed lots can exhibit increased crude fat, seed oil, and/or protein content and are thus useful in a variety of processes. In certain embodiments, such seed lots can be used as feedstock in methods of extracting oil and/or protein from seed. It is thus anticipated that the yield of oil and/or protein will be increased by use of the seed lots provided herein as feedstock in comparison to methods where seed lots obtained from commodity seed are used as feedstock. Such commodity seed would in general comprise seed harvested from mature plants grown from seeds and/or plants that were not treated with an effective amount of a *Methylobacterium* strain or strains. In certain embodiments, such seed lots can be used in methods of manufacturing a food or feed ingredient to obtain a food or feed ingredient with increased oil and/or protein content. In certain embodiments, the seed lot will comprise at least about 10, 20, 50, 100, 500, or 1000 seed. In certain embodiments, the seed lot will comprise at least about 10, 20, 50, 100, 500, or 1000 pounds or kilograms of seed. In certain embodiments, the seed lot will comprise at least about 100, 200, 500, 1000, 5000, or 10,000 bushels of seed. Seed lots can be packaged or contained in a bag, box, or other packaging suitable for storing and/or shipping. In certain embodiments, the seed lot can be packaged, stored, and/or shipped in a silo bag. In certain embodiments, such silo bags can comprise a triple layer of thick laminated extruded plastic (polyethylene) about 230-235 microns thick, where the two outer layers are white with a UV protective coating while the inner layer in contact with the seed is black (Ileleji, K. Use of Silo Bags for Commodity Grain Storage in Indiana, 2014; on the https internet site "extension.purdue.edu/article/6963"). In certain embodiments, a silo bag filled with a seed lot will comprise a tube of about 8 to 12 ft in diameter and up to about 200 ft in length and can hold about 8,000 to 12,000 bushels of seed. In certain embodiments, any of the aforementioned packaged seed lots can comprise a tag or label useful of identifying and tracking the seed lot. Such tags or labels can comprise a barcode, an RFID tag, or other identifiers. In certain embodiments, the tag or label will identify the seed lot as comprising at least about 50%, 70%, 80%, 90%, 95%, 98%, or 99% of seeds harvested from mature plants grown from seeds and/or plants treated with an effective amount of a *Methylobacterium* strain or strains. In certain embodiments, the tag or label will identify the seed lot as comprising at least about 50%, 70%, 80%, 90%, 95%, 98%, or 99% of seeds having an increased crude fat, seed oil, and/or protein content in comparison to commodity seed.

In certain embodiments of the methods provided herein, the seed lots harvested from mature plants grown from seeds and/or plants treated with an effective amount of a *Methylobacterium* strain or strains are segregated from other seed lots comprising commodity seed that has not been uniformly subjected to such *Methylobacterium* treatments. Methods for achieving such segregation include: (1) planting and/or treating defined areas of a field with *Methylobacterium*-strain treated seed and/or with a *Methylobacterium* treatment (e.g., in furrow and/or foliar applications, soil drenches, and or any combination thereof); (2) separating the defined areas of a field from adjacent untreated areas with a unplanted or other border which permits separate harvest of seed from the mature plants; and/or (3) use of global position system (GPS) coordinates in the planting, treating, and or harvesting machinery to facilitate harvest of seed from mature plants grown from seeds and/or plants treated with an effective amount of a *Methylobacterium* strain or strains. Segregation and transfer of the seed lot to an oil and/or protein extraction plant, a food or feed ingredient manufacturing facility, or a food or feed manufacturing facility are also facilitated by use packaging, labelling, or tagging systems such as those described above.

Seed lots comprising at least 50%, 70%, 80%, 90%, or 95% of the seeds harvested from mature plants grown from seeds and/or plants treated with an effective amount of a *Methylobacterium* strain or strains can also be used to obtain seed oil and/or seed protein-enriched fractions, to increase yield of protein- or oil-containing fractions from seed lots, to manufacture food or feed ingredients, or to manufacture food or feed. Schematic diagrams of certain seed processing methods are depicted in FIG. 1 (for *Brassica* sp, seeds including rapeseed and canola seed) and FIG. 2 (for soybean). FIGS. 1 and 2 are solely illustrative, as any seed processing methods can be employed. Such processes depicted in FIGS. 1 and 2 are also illustrative of processes which can be adapted for use with other oil seeds such as sunflower, flax, cotton, peanut, linseed, and the like. For example, cotton seed would be delinted in most instances where cottonseed was used as a feedstock.

Food or feed ingredients obtained from the seed lots provided herein include crude or refined seed oil, pressed seed cake, pressed or double pressed seed meal, defatted or partially defatted seed meal or flakes, solvent extracted seed meal, desolventized seed meal, expandate resulting from passing processed seed materials through an expander, extrudate resulting from passage of processed seed materials through an extruder, and the like. In certain embodiments, the feed ingredients can comprise pressed seed cake or meal, defatted or partially defatted seed meal, solvent extracted seed meal, desolventized seed meal, expandate, or extrudate, which has been pelletized. An oil-enriched fraction obtained by the methods provided herein can thus comprise a crude oil (e.g., oil obtained from seed by a mechanical pressing or expelling of seed or a processed product thereof), a seed oil containing solvent fraction, or a desolventized oil obtained from a seed oil containing solvent fraction. Seed oil containing solvent fractions can be obtained by extraction of processed seed lot products with solvents such as hexane (e.g., mixed hexanes). Seed oil can also be prepared by supercritical fluid extraction (SFE; e.g., supercritical $CO_2$) of processed seed lot products. Supercritical fluid extraction (e.g., supercritical $CO_2$) of processed seed lot products methods described in the literature (e.g., Jokid et al., 2012) can be adapted for use with feedstock comprising seed lots provided herein. Processed seed lot products that can be subject to mechanical pressing or expelling and/or to solvent extraction include dehulled, delinted, crushed, macerated, and/or ground seed, expandate, and extrudate. Expandate is obtained by passage of seed materials through expanders, which subject processed seed material to high pressure, shear forces, and high temperatures for short time intervals of about a minute through steam injection. Commercial expanders include an Anderson oilseed expander (Anderson International, Stow, OH, USA), Andritz Expander (Andritz, Graz, Austria), Kahl expander (Amandus Kahl USA, Atlanta, GA), and the like. As used herein, an extrudate is defined as a material that is obtained by subjecting a seed material to pressure and/or shear forces without steam injection. A protein-enriched fraction produced by the methods provided herein can thus include pressed seed cake, pressed or double pressed seed meal, defatted or partially defatted seed meal or flakes, solvent extracted seed meal, desolventized seed meal, or expandate. A protein-enriched fraction can also include an aqueous fraction obtained by extracting dehulled, delinted, crushed, macerated, and/or ground seed, expandate, pressed seed cake, pressed or double pressed seed meal, defatted or partially defatted seed meal or flakes, solvent extracted seed meal, desolventized seed meal, and/or extrudate with water, a buffered aqueous solution, an acidic aqueous solution, a basic aqueous solution, or a salt-containing solution.

Processed or unprocessed food or feed ingredients obtained from seed lots comprising at least 50%, 70%, 80%, 90%, or 95% of the seeds harvested from mature plants grown from seeds and/or plants treated with an effective amount of a *Methylobacterium* strain or strains can be used as ingredients in methods of making a food or feed with improved mineral nutrient, vitamin, oil and/or protein content. In certain embodiments, such processed food or feed ingredients can comprise dehulled, delinted, crushed flaked, defatted or partially defatted seed meal or seed cake, non-defatted seed meal from the seed lot or an oil and/or a protein enriched fraction from the seed lot. In certain embodiments, such unprocessed food ingredients can comprise whole seed from the seed lot. In certain embodiments, whole seed can be combined with silage, seed meal, additional vitamins (e.g., vitamins A, D, and/or E), additional mineral nutrients (e.g., calcium, sodium, iron, magnesium, manganese, cobalt, selenium, dyes, and/or amino acids (e.g., methionine and/or lysine) to provide animal feed. Such food or feed ingredients obtained from the seed lot can be incorporated into a food or feed by steps comprising at least one of combining, mixing, heating, extruding, pelletizing, molding, and or forming that food or feed ingredient into a food or feed product. In certain embodiments, the food or feed ingredients obtained from the seed lot can be incorporated into a food or feed with another food or feed ingredient by steps comprising at least one of combining, mixing, heating, extruding, pelletizing, molding, and or forming the food or feed ingredients into a food or feed product. Additional food or feed ingredients that can be incorporated into the food of feed product in combination with food or feed ingredients obtained from the seed lot include starches, hydrolyzed starches, modified starches, sugars, fiber, emulsifiers, flavorants, additional vitamins (e.g., vitamins A, D, and/or E), additional mineral nutrients (e.g., calcium, sodium, iron, magnesium, manganese, cobalt, selenium, dyes, amino acids (e.g., methionine and/or lysine), antimicrobial agents, and the like. Methods and compositions for making food-, pet food- or feed compositions comprising pellets, emulsions, fat compositions, and the like disclosed in U.S. Patent Appl. Pub. Nos. US20180125101, US20180103654, and/or US20170112159, which are each incorporated herein in their entireties, can be adapted for use with the food and feed ingredients provided herein to make food or feed products.

Seed lots comprising at least 50%, 70%, 80%, 90%, or 95% of the seeds harvested from mature plants grown from seeds and/or plants treated with an effective amount of a *Methylobacterium* strain or strains can be used as feedstock to increase yield of oil in oil-enriched fractions in comparison to the yield obtained when control seed lots are used as feedstock. In this embodiment, oil yield is defined as the amount of oil in an oil-enriched fraction obtained per unit of seed lot feedstock used in an oil extraction process. In certain embodiments, oil yield can be expressed as the mass, or weight of oil in an oil-enriched fraction obtained from an oil extraction process per kilogram seed used in the process. In certain embodiments, oil yield can be expressed as the mass, or weight of oil in an oil-enriched fraction obtained from an oil extraction process per seed or per bushel of seed used in the process. In other embodiments, oil yield can be expressed as a volume of oil obtained or present in an oil-enriched fraction per kilogram seed used in the process. Separation steps that can be used in an oil extraction process to obtain an oil-enriched fraction can include mechanical pressing or expelling of seed or a processed seed product (e.g., non-defatted seed meal, flakes, expandate, or extrudate) to obtain a crude oil fraction. Separation steps that can be used to obtain an oil-enriched fraction can also include solvent or SFE extraction of a processed seed product (e.g., non-defatted seed meal, flakes, expandate, or extrudate) to obtain an oil-enriched fraction. In certain embodiments, seed oil yield can be improved relative to controls even with reduced energy inputs into an oil extraction process by using the aforementioned seed lots as feedstock. In certain embodiments, seed oil yield can be improved when temperatures of oil extraction processes (e.g., pressing, expansion, or extrudation) are reduced by at least 1%, 2%, 5%, 10%, or 20% in comparison to processes where a control seed lot (e.g., a seed lot obtained from plants or plants grown from seeds that were not treated with *Methylobacterium*) is processed under reduced temperatures. In certain embodiments, seed oil yield can be improved when temperatures of oil extraction processes (e.g., pressing, expansion, or extrudation) are reduced by about 1%, 2%, or 5%, to 10%, 20%, 30%, 40%, or 50% in comparison to processes where a control seed lot (e.g., a seed lot obtained from plants or plants grown from seeds that were not treated with *Methylobacterium*) is processed under the same reduced temperatures. In certain embodiments, seed oil yield can be improved when energy inputs into an oil extraction process are reduced by at least 1%, 2%, 5%, 10%, or 20% in comparison to processes where a control seed lot (e.g., a seed lot obtained from plants or plants grown from seeds that were not treated with *Methylobacterium*) is processed under the same reduced energy input conditions. In certain embodiments, seed oil yield can be improved when energy inputs into an oil extraction process are reduced by about 1%, 2%, or 5%, to about 10%, 20%, 30%, 40%, or 50% in comparison to processes where a control seed lot (e.g., a seed lot obtained from plants or plants grown from seeds that were not treated with *Methylobacterium*) is processed under the same reduced energy input conditions.

Seed lots comprising at least 50%, 70%, 80%, 90%, or 95% of the seeds harvested from mature plants grown from seeds and/or plants treated with an effective amount of a *Methylobacterium* strain or strains can be used as feedstock to increase yield of protein in protein-enriched fractions in comparison to the yield obtained when control seed lots are used as feedstock in a protein extraction process. In this embodiment, protein yield is defined as the amount of protein in a protein-enriched fraction obtained per unit of seed lot feedstock used in a protein extraction process. In certain embodiments, protein yield can be expressed as the mass or weight of protein in a protein-enriched fraction obtained in a protein extraction process per kilogram seed used in the process. Separation steps that can be used to obtain a protein-enriched fraction can include delinting and/or dehulling of seed to obtain a protein-enriched fraction comprising delinted and/or dehulled whole seed. Separation steps that can be used to obtain a protein-enriched fraction can also include grinding, macerating, flaking, and/or drying of whole, delinted, or dehulled seed to obtain a protein enriched product comprising seed meal, flakes, and the like which can be non-defatted, defatted, or partially defatted. Separation steps that can be used to obtain a protein-enriched fraction can include mechanical pressing or expelling of seed or a processed seed product (e.g., non-defatted seed meal, flakes, expandate, or extrudate) to obtain a protein-enriched fraction comprising pressed seed meal or a seed cake. Separation steps that can be used to obtain a protein-enriched fraction can also include solvent or SFE extraction of a processed seed product (e.g., non-defatted seed meal, flakes, expandate, or extrudate) to obtain a protein-enriched fraction comprising defatted or partially defatted seed meal, flakes, expandate, or extrudate. In certain embodiments, seed protein yield can be improved relative to controls even with reduced energy inputs into a protein-enrichment process by using the aforementioned seed lots as feedstock. In certain embodiments, seed protein yield can be improved when temperatures of protein enrichment processes (e.g., pressing, expansion, or extrusion) are reduced by at least 1%, 5%, 10%, or 20% in comparison to processes where a control seed lot is processed under reduced temperatures. In certain embodiments, seed protein yield can be improved when temperatures of protein enrichment processes (e.g., pressing, expansion, or extrusion) are reduced by about 1%, 2%, or 5% to about 10% 20%, 30%, 40%, or 50% in comparison to processes where a control seed lot is processed under the same reduced temperatures. In certain embodiments, seed protein yield can be improved when energy inputs into an oil extraction process are reduced by at least 1%, 5%, 10%, or 20% in comparison to processes where a control seed lot is processed under the same reduced temperatures. In certain embodiments, seed protein yield can be improved when energy inputs into an oil extraction process are reduced by about 1%, 2%, or 5% to about 10%, 20%, 30%, 40%, or 50% in comparison to processes where a control seed lot is processed under the same reduced energy input conditions.

Seed, seed lots, food ingredients, and feed ingredients with increased oil content are provided as are methods for obtaining and using such seed, seed lots, food ingredients, and feed ingredients. In certain embodiments, the oil content of the seed, seed lots, food ingredients, and feed ingredients is increased by at least about 0.5%, 1%, or 2% per gram dry or wet weight of the in comparison to oil content of a control seed, seed lot, food ingredient, or feed ingredient. In certain embodiments, oil content of the seed, seed lots, food ingredients, and feed ingredients is increased by about 0.5%, 1%, or 2% to about 3%, 4%, 5%, 6%, 7%, 8%, 9%, or 10% per gram dry or wet weight of seed, seed lots, food ingredients, and feed ingredients in comparison to oil content of a control seed, seed lot, food ingredient, or feed ingredient. Controls include seed or seed lots harvested from mature control plants grown from an untreated control seed or untreated control plant as well as food and feed ingredients obtained from these control seed or seed lots.

Seed, seed lots, food ingredients, and feed ingredients with increased protein content are provided as are methods for obtaining and using such seed, seed lots, food ingredients, and feed ingredients. In certain embodiments, protein content is increased by at least about 0.5%, 1%, or 2% per gram dry or wet weight of the seed, seed lots, food ingredients, and feed ingredients in comparison to protein content of a control seed, seed lot, food ingredient, or feed ingredient. In certain embodiments, protein content of the seed, seed lots, food ingredients, and feed ingredients is increased by about 0.5% to about 1%, 2%, 3%, 4%, 5%, 6%, 7%, 8%, 9%, or 10% per gram dry or wet weight of the seed, seed lots, food ingredients, and feed ingredients in comparison to protein content of a control seed, seed lot, food ingredient, or feed ingredient. Controls include seed or seed lots harvested from mature control plants grown from an untreated control seed or untreated control plant as well as food and feed ingredients obtained from these control seed or seed lots.

Seed, seed lots, food ingredients, and feed ingredients with both increased oil and protein content are also provided as are methods for obtaining and using such seed, seed lots, food ingredients, and feed ingredients. In certain embodiments, protein content is increased by at least about 0.5%, 1%, or 2% per gram dry or wet weight of the seed, seed lots, food ingredients, and feed ingredients in comparison to protein content of a control seed, seed lot, food ingredient, or feed ingredient and oil content is increased by at least about 0.5%, 1%, or 2% per gram dry or wet weight of the in comparison to oil content of a control seed, seed lot, food ingredient, or feed ingredient. In certain embodiments, protein content is increased by about 0.5% to about 1%, 2%, 3%, 4%, 5%, 6%, 7%, 8%, 9%, or 10% per gram dry or wet weight of the seed, seed lots, food ingredients, and feed ingredients in comparison to protein content of a control seed, seed lot, food ingredient, or feed ingredient and oil content is increased by about 0.5%, 1%, or 2% to about 3%, 4%, 5%, 6%, 7%, 8%, 9%, or 10% per gram dry or wet weight of the seed, seed lots, food ingredients, and feed ingredients in comparison to oil content of a control seed, seed lot, food ingredient, or feed ingredient. Controls include seed or seed lots harvested from mature control plants grown from an untreated control seed or untreated control plant as well as food and feed ingredients obtained from these control seed or seed lots.

Plants, plant parts, food ingredients, and feed ingredients having increased levels of at least one mineral nutrient and/or at least one vitamin in comparison to a control plant, plant part, or feed ingredient are provided, as are methods for obtaining and using such plants, plant parts, food ingredients, and feed ingredients. In certain embodiments, the content of at least one mineral nutrient and/or at least one vitamin in the plants, plant parts, food ingredients, and feed ingredients is increased by at least about 1%, or 2% to about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% per gram dry or wet weight in comparison to the content of the at least one mineral nutrient and/or at least one vitamin in a control plant, plant part, food ingredient, or feed ingredient. In other embodiments, the content of at least one mineral nutrient and/or at least one vitamin in the plants, plant parts, food ingredients, and feed ingredients is increased by more than 30%, including 35%, 40%, 45%, 50% or greater than 50% in comparison to the content of the at least one mineral nutrient and/or at least one vitamin in a control plant, plant part, food ingredient, or feed ingredient. In some embodiments, the content of more than one mineral nutrient and/or more than one vitamin is increased in a plant, plant part, food ingredient, and feed ingredient, and percent increases can vary for each of the mineral nutrients and/or vitamins, with each increased mineral nutrient and vitamin being increased by at least about 1%, or 2% to about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% or more per gram dry or wet weight. Controls include plants or plant parts harvested from control plants grown from an untreated control seed or untreated control plant as well as food and feed ingredients obtained from these control plants or plant parts.

The mineral nutrient, vitamin, crude fat, oil, and/or protein content of whole seed, protein-enriched fractions, oil-enriched fractions, food ingredients, feed ingredients, and the like obtained from seed lots comprising at least 50%, 70%, 80%, 90%, or 95% of the seeds harvested from mature plants grown from seeds and/or plants treated with an effective amount of a *Methylobacterium* strain or strains can be determined by a variety of different techniques or combinations of techniques. Crude fat can be determined by methods comprising diethyl ether extraction of a dried sample, evaporation of the diethyl ether, and weighing the dried material recovered from the diethyl ether extract (Theix et al., 2003). Examples of crude fat determination methods include AOAC (formerly Association of Official Analytical Chemists) 920.39 and AACC (formerly American Association of Cereal Chemists) 30-20. Oil content can be determined by methods comprising nuclear magnetic resonance (NMR), near infrared spectroscopy (NIRS), gas-chromatography-mass spectroscopy (GC-MS), gas-chromatography-flame ionization detection (GC-FID), thin layer chromatography-flame ionization detection, liquid chromatography (LC)-mass spectroscopy (MS), liquid chromatography (LC)-electrospray ionization (EI)-mass spectroscopy (MS), or liquid chromatography (LC)-electrospray ionization (EI)-tandem mass spectroscopy (MS). Methods of determining oil content of seeds in general and single seeds by NIRS disclosed in U.S. Patent Appl. Pub. US20190003931, incorporated herein by reference in its entirety, can be adapted for use in the methods disclosed herein. Protein content can be determined by methods comprising nuclear magnetic resonance (NMR), near infrared spectroscopy (NIRS), a colorimetric assay, liquid chromatography (LC)-mass spectroscopy (MS), or matrix-assisted laser desorption/ionization time-of-flight mass spectrometry (MALDI-TOF). Assays for protein content can include colorimetric assays such as Lowry (Hartree, E. F., 1972) and Bradford (Bradford, 1976) assays. Protein content can also be determined indirectly by amino acid analysis or nitrogen determination (Maehre, et al., 2018). Nitrogen-based protein content determination methods include Dumas (Dumas, 1831) and Kjeldahl (Kjeldahl, 1883) methods. Nitrate and nitrite nitrogen content determination methods include Cadmium Reduction and Colorimetric analysis by Flow Injection system (Lachat); AOAC 968.07. Mineral Digestion can be accomplished by Open Vessel Microwave SW846-3051A (AOAC 991-10D(e)). Mineral analysis can be conducted by Inductively Coupled Argon Plasma (ICAP); AOAC 985.01. Mineral nutrients, vitamins, crude fat, oil, and protein content of seeds and various foods, feeds, feed ingredients, and food ingredients can also be determined by standard methods set forth by the AACC, AOAC in Official Methods of Analysis of AOAC INTERNATIONAL, 21st Edition (2019) and in the Codex Alimentarius of International Food Standards set forth by the Food and Agriculture Organization of the United Nations (FAO) or WHO (CXS 234-19991, Adopted in 1999).

EXAMPLES

Figure 3:
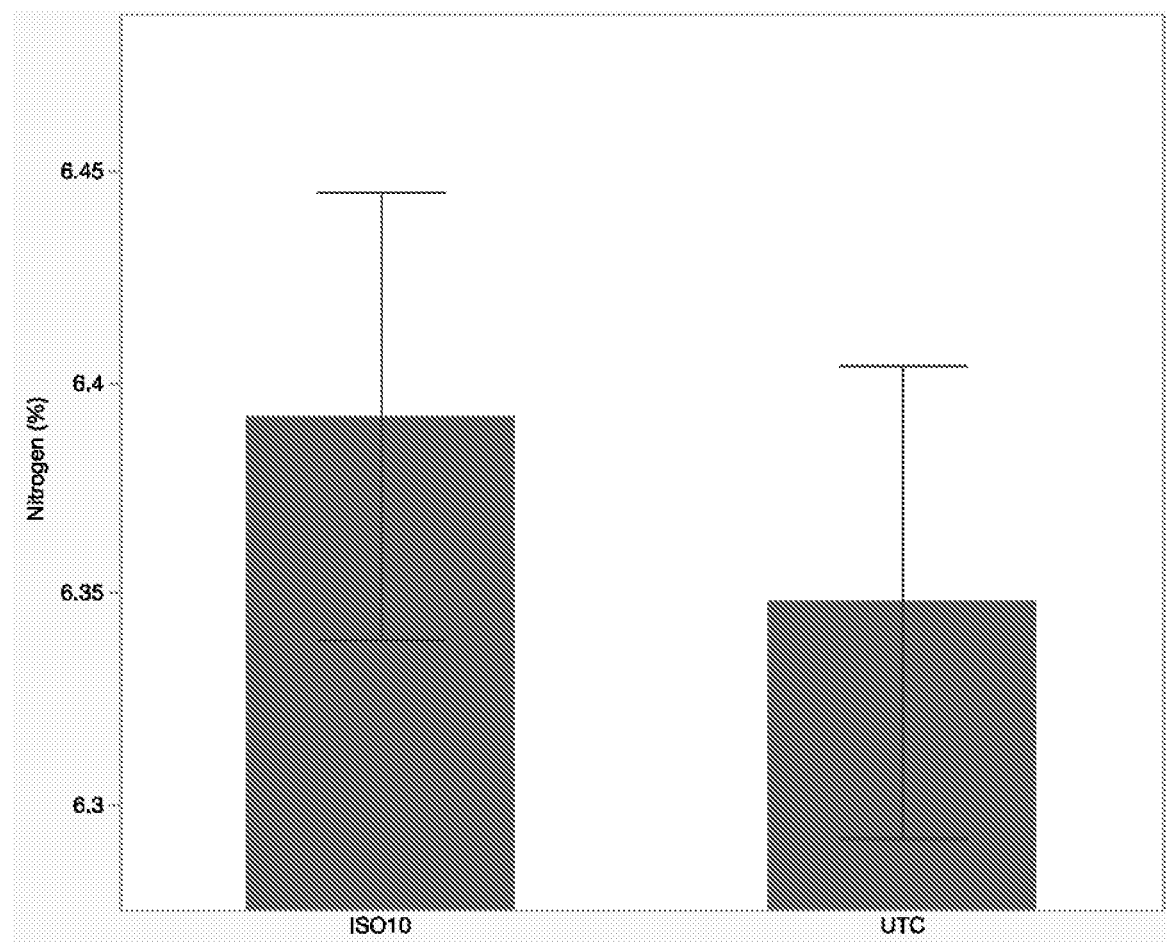
FIG. 3 shows a comparison of % nitrogen content of seed harvested from soybean plants treated with *Methylobacterium* ISO10 and untreated control seed (t=-2.4; p=0.042).
Figure 4:
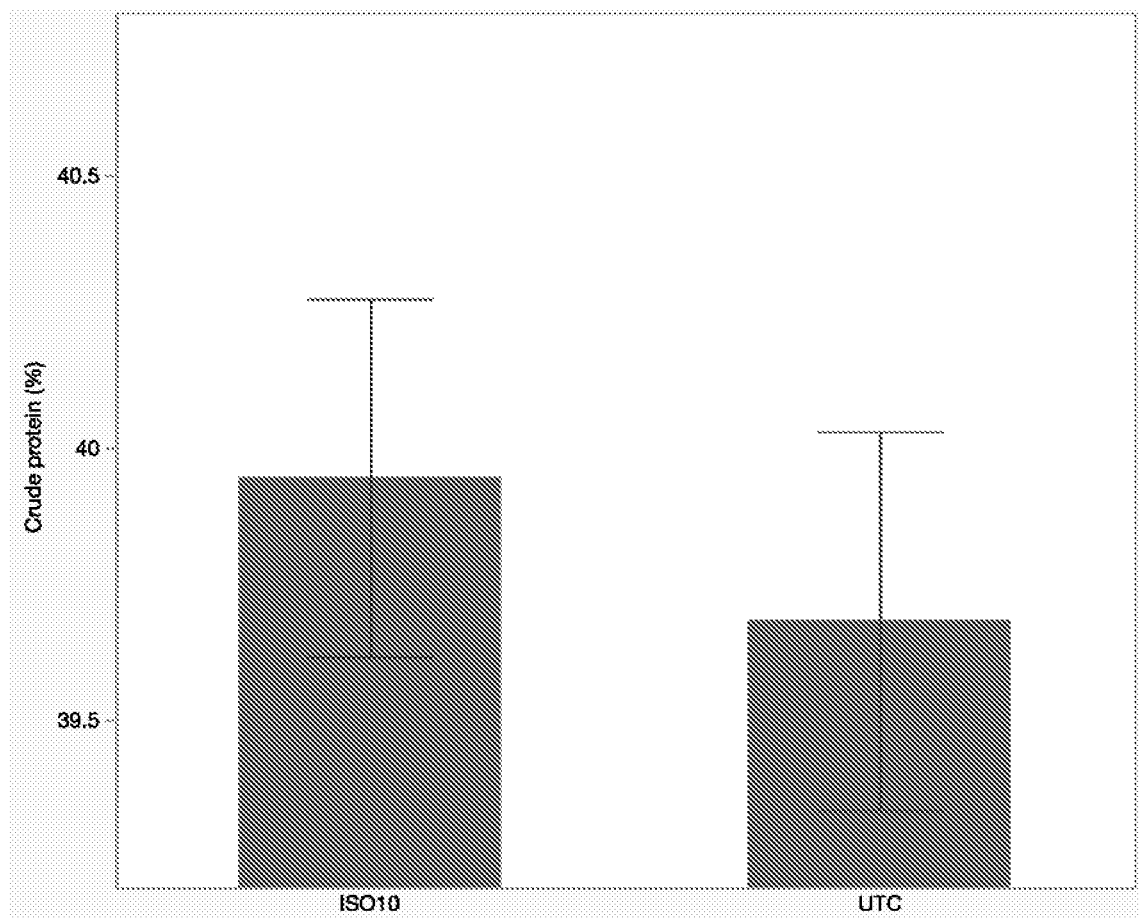
FIG. 4 shows a comparison of % crude protein of seed harvested from soybean plants treated with *Methylobacterium* ISO10 and untreated control seed (t=-2.24; p=0.055).
Figure 5:
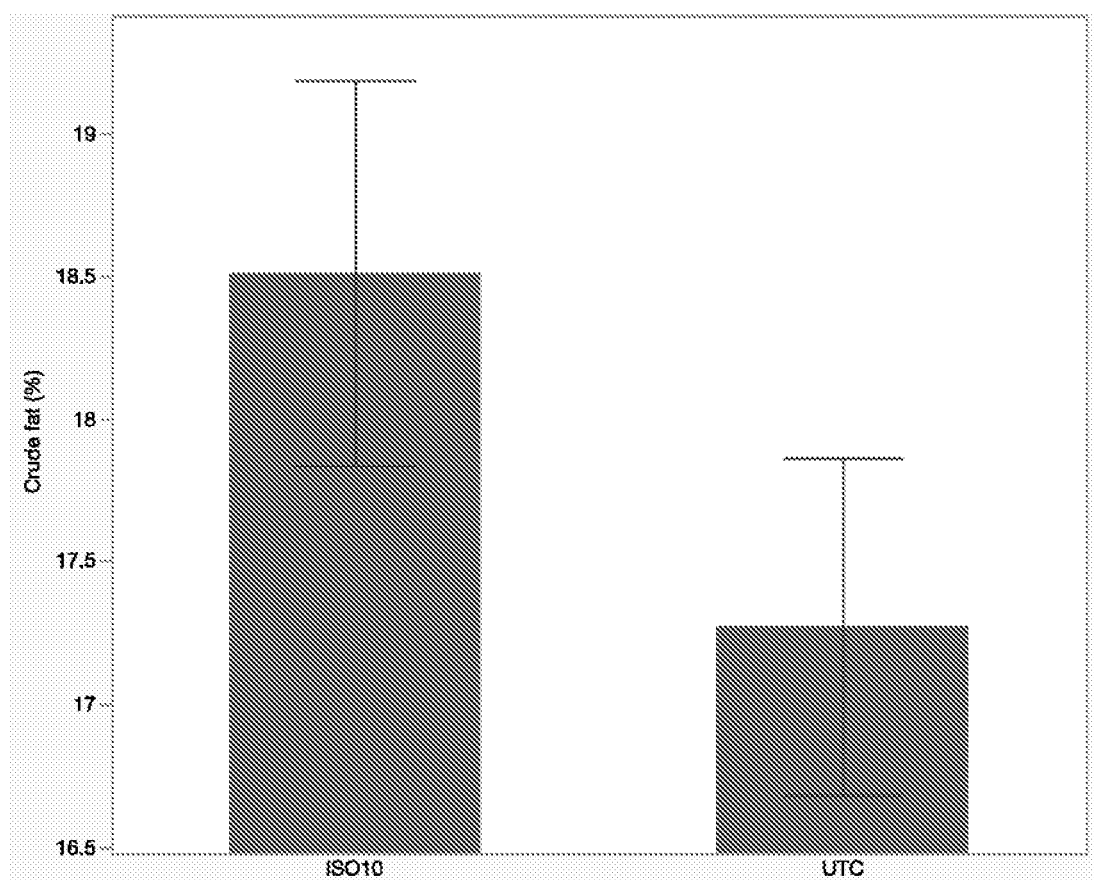
FIG. 5 shows a comparison of % crude fat content of seed harvested from soybean plants treated with *Methylobacterium* ISO10 and untreated control seed (t=-7.11; p<0.0001).
Figure 6:
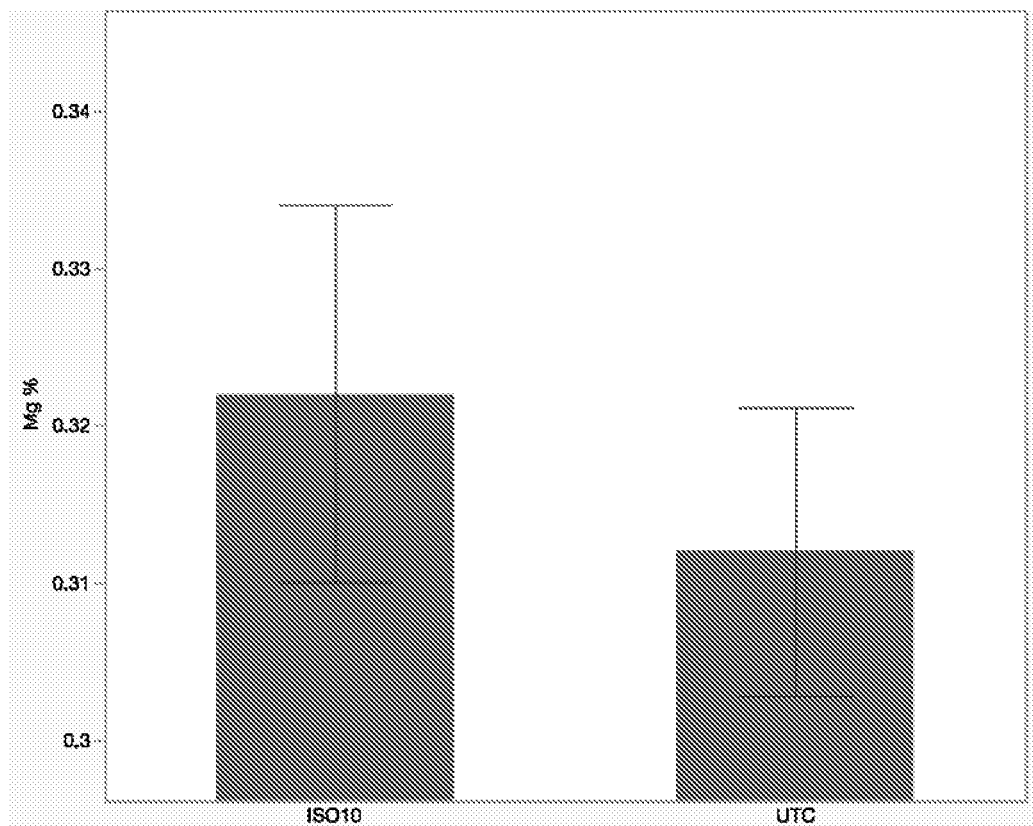
FIG. 6 shows a comparison of % magnesium content of seed harvested from soybean plants treated with *Methylobacterium* ISO10 and untreated control seed (t=-4.47; p=0.0021).
Figure 7:
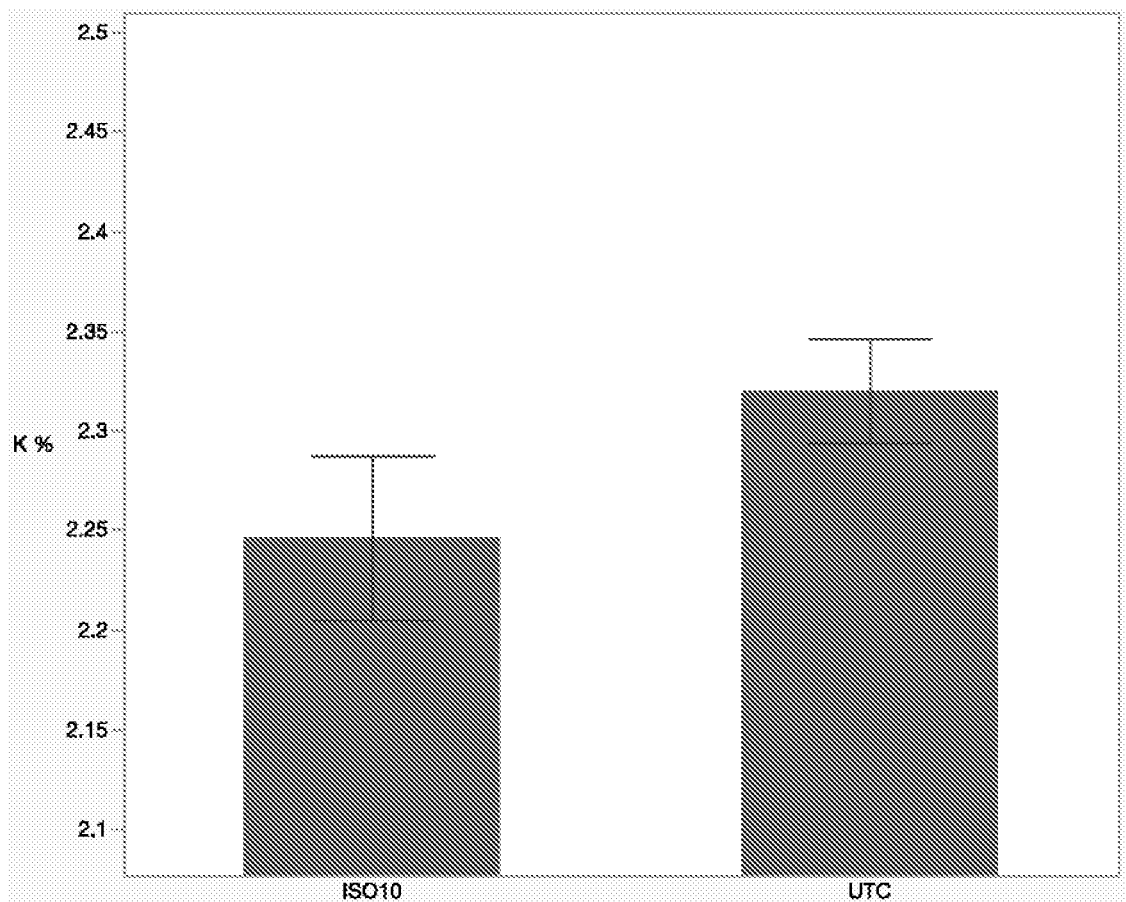
FIG. 7 shows a comparison of % potassium content of seed harvested from soybean plants treated with *Methylobacterium* ISO10 and untreated control seed (t=3.37; p=0.0098).
Figure 8:
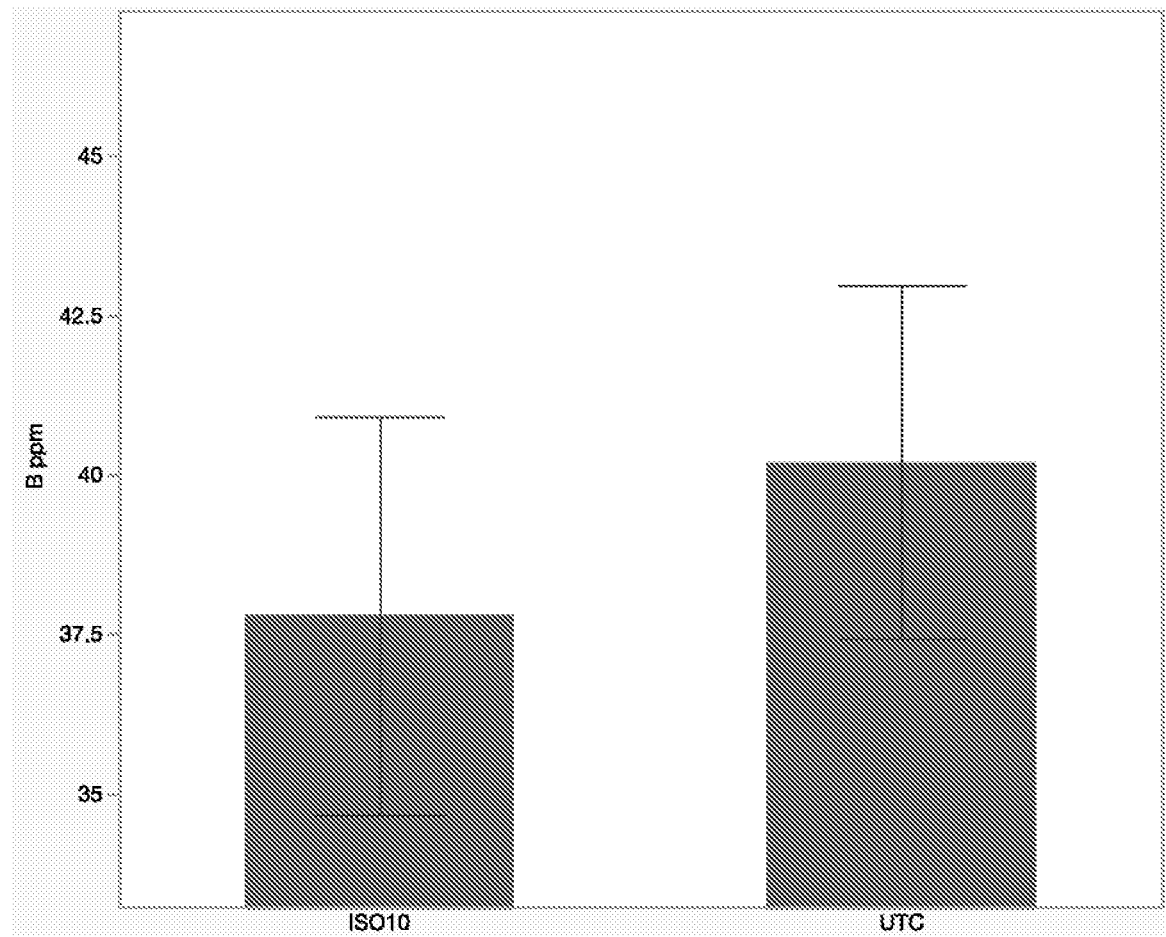
FIG. 8 shows a comparison of % boron content of seed harvested from soybean plants treated with *Methylobacterium* ISO10 and untreated control seed (t=2.08; p=0.071).

Example 1. Effects of *Methylobacterium* Strain ISO10 (NRRL B-50938) Treatment of Soybean on Harvested Soybean Quality Soybean seeds (treated with standard seed applied fungicides and insecticides) were over-treated with *Methylobacterium* strain ISO10 at a rate of $10^6$ CFU per seed (NRRL B-50938) and grown at five distinct field locations in the Midwestern United States in the summer of 2018 in parallel with untreated control soybean plants. Locations were Cedar Falls, IA, Miami, MO, Dana, IA, Whitewater, WI and Aurora, NE Seed was harvested from the treated and untreated control (UTC) soybean plants and assayed for micro- and macronutrient compositions. The results of the experiments are shown in FIG. 3 (percentage (%) nitrogen), FIG. 4 percentage (%) crude protein), FIG. 5 (percentage (%) crude fat), FIG. 6 (percentage (%) Magnesium), FIG. 7 percentage (%) Potassium), and FIG. 8 (percentage (%) Boron). Welch's two-tailed t-test with Location as a random effect was used for all statistical contrasts. Grain was combined for all ISO10 and UTC plots at each of five (5) locations, giving a sample size of 5 observations per treatment for every variable. Nutrient and crude fat/protein contents were measured as the percentage of dry weight of the sample.

Across the full panel of macro- and micronutrients tested and across crude protein & fat, ISO10 significantly altered the grain nutrient and quality profiles relative to the Untreated Control (UTC) (Table 2). Importantly, crude fat (determined by AACC\30-20) increased by 7.2% ($p<0.0001$) with ISO10 treatment. Crude protein and grain nitrogen contents (determined by AOAC (968.06) were higher with ISO10 treatment (0.7% increase for both, at significance levels of $p=0.055$ and 0.042, respectively). Grain magnesium content (determined by AOAC 975.03B (b)/AOAC 985.01) also increased significantly with ISO10 treatment (3.1% increase at $p=0.0021$). ISO10 treatment resulted in a significantly lower grain potassium content (3.3% decrease at $p=0.0098$) and marginally lower grain boron content (6.3% decrease at $p=0.07$) (as determined by AOAC 975.03B(b)/AOAC 985.01). Other macro- and micronutrients did not differ significantly between the ISO10 treatment and the UTC.

TABLE 2

Mean nutrient contents on a dry weight basis, percent difference of ISO10 from UTC, and contrast p-values.

| Nutrient type | Nutrient (units) | ISO10 value | UTC value | % difference from UTC | Contrast p-value |
|---|---|---|---|---|---|
| Macro-nutrient | Nitrogen (%) | 6.392 | 6.348 | +0.7% | *0.042* |
| | Phosphorus (%) | 0.624 | 0.644 | −3.2% | 0.17 |
| | Potassium (%) | 2.246 | 2.320 | −3.3% | *0.0098* |
| | Calcium (%) | 0.390 | 0.356 | +8.7% | 0.40 |
| | Magnesium (%) | 0.322 | 0.312 | +3.1% | *0.0021* |
| | Sulfur (%) | 0.342 | 0.338 | +1.2% | 0.43 |
| Micro-nutrient | Zinc (ppm) | 40 | 40 | 0 | 1.00 |
| | Manganese (ppm) | 36.4 | 36.4 | 0 | 1.00 |
| | Iron (ppm) | 79.6 | 78.0 | +2.0% | 0.57 |
| | Copper (ppm) | 13.6 | 13.2 | +2.9% | 0.43 |
| | Boron (ppm) | 37.8 | 40.2 | −6.3% | 0.071 |
| | Crude protein (%) | 39.944 | 39.680 | +0.7% | 0.055 |
| | Crude fat (%) | 18.512 | 17.272 | +7.2% | *<0.0001* |

Bold italics indicate p < 0.05.

Figure 9:
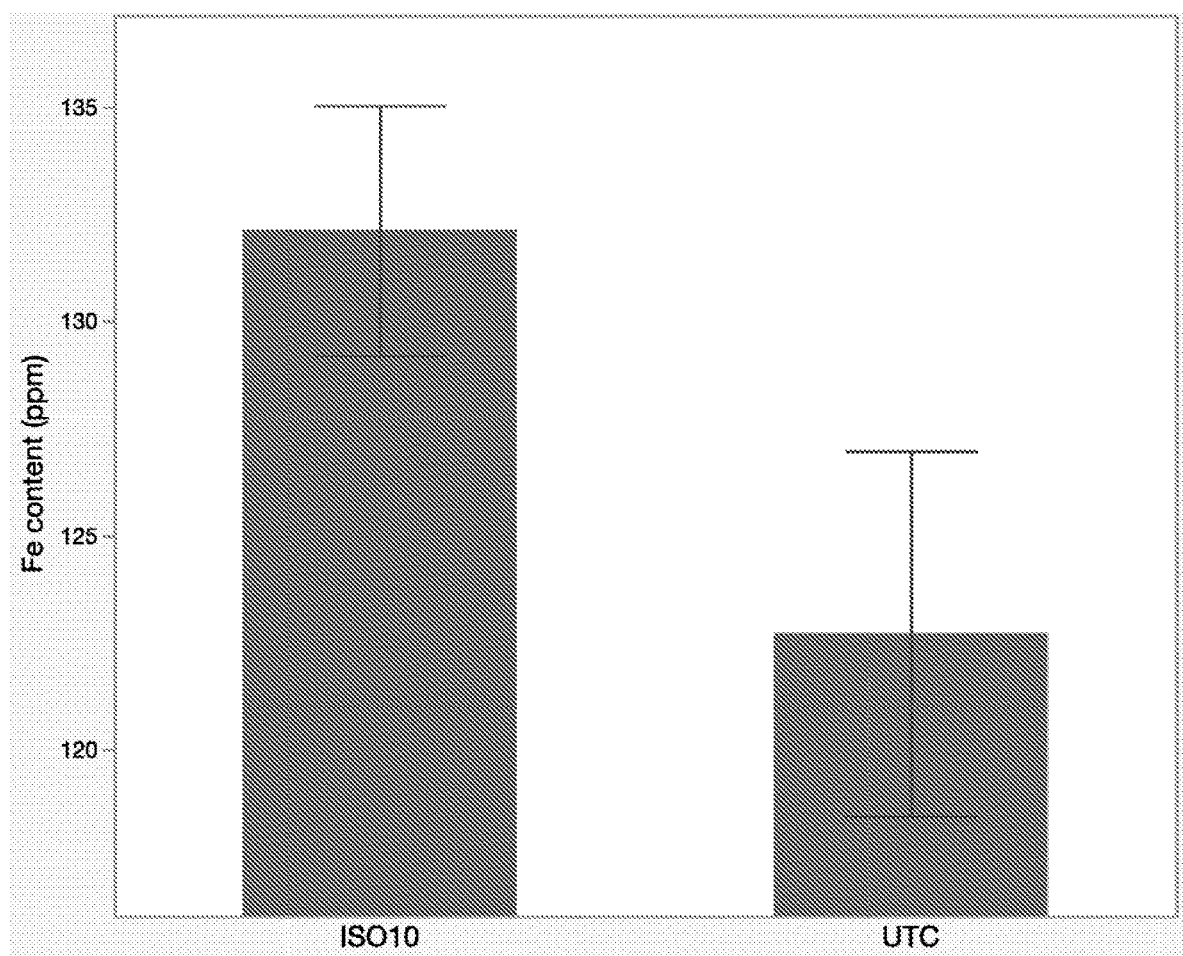
FIG. 9 shows a comparison of iron content of stage V1 leaf samples from soybean plants grown from seeds treated with *Methylobacterium* ISO10 and stage V1 leaf samples from soybean plants grown from untreated seeds.
Figure 10:
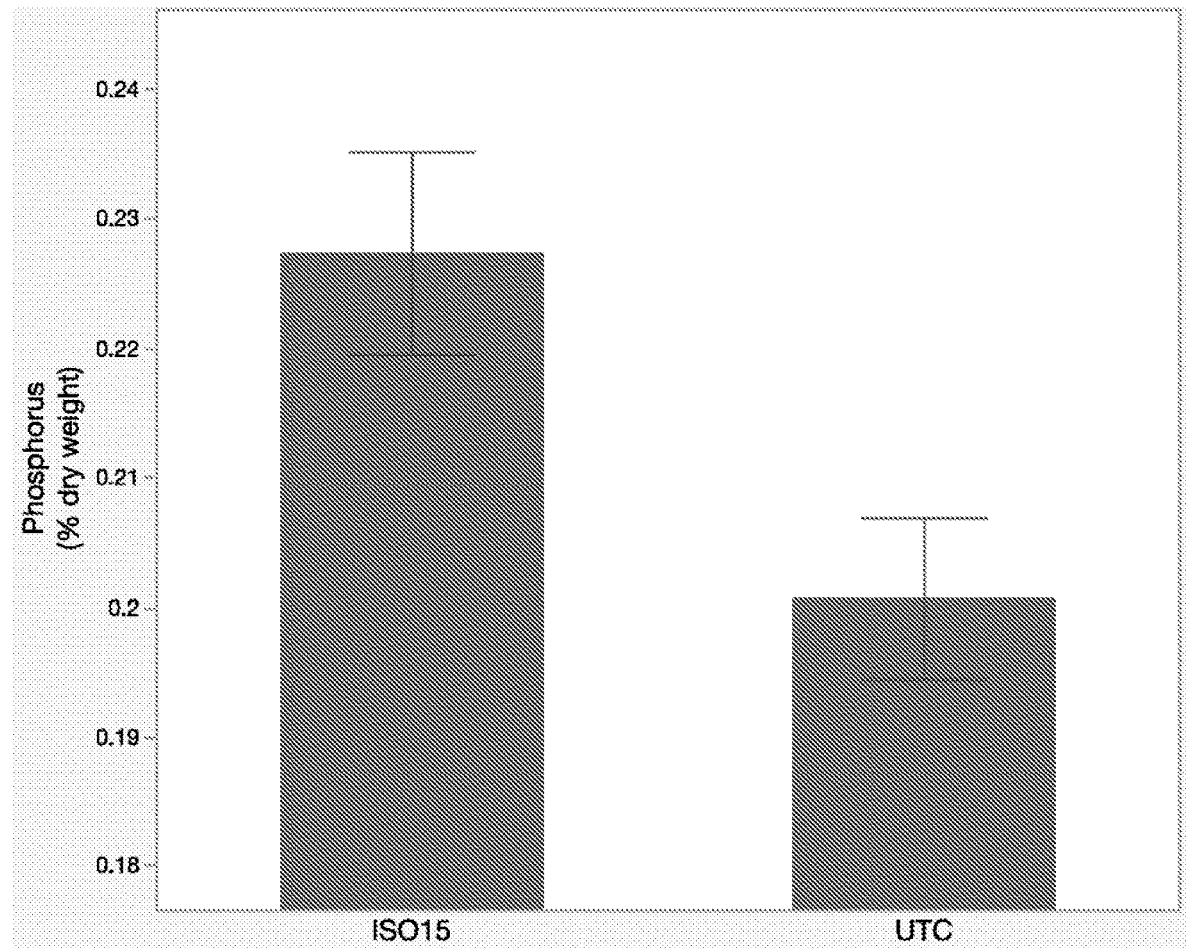
FIG. 10 shows a comparison of phosphorus content of stage V2 leaf samples from corn plants grown from seeds treated with *Methylobacterium* ISO15 and of stage V2 leaf samples from corn plants grown from untreated seeds.
Figure 11:
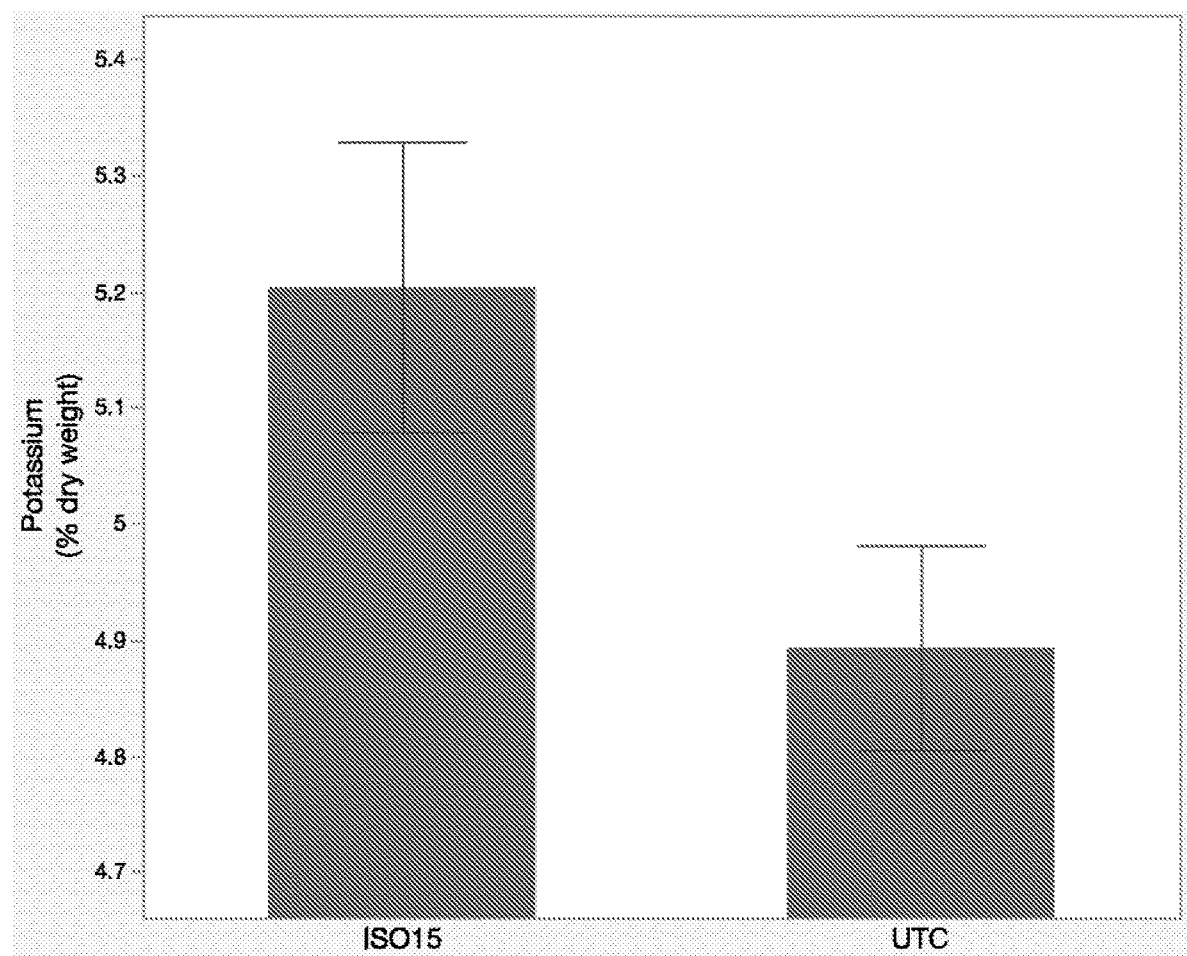
FIG. 11 shows a comparison of potassium content of stage V2 leaf samples from corn plants grown from seeds treated with *Methylobacterium* ISO15 and of stage V2 leaf samples from corn plants grown from untreated seeds.
Figure 12:
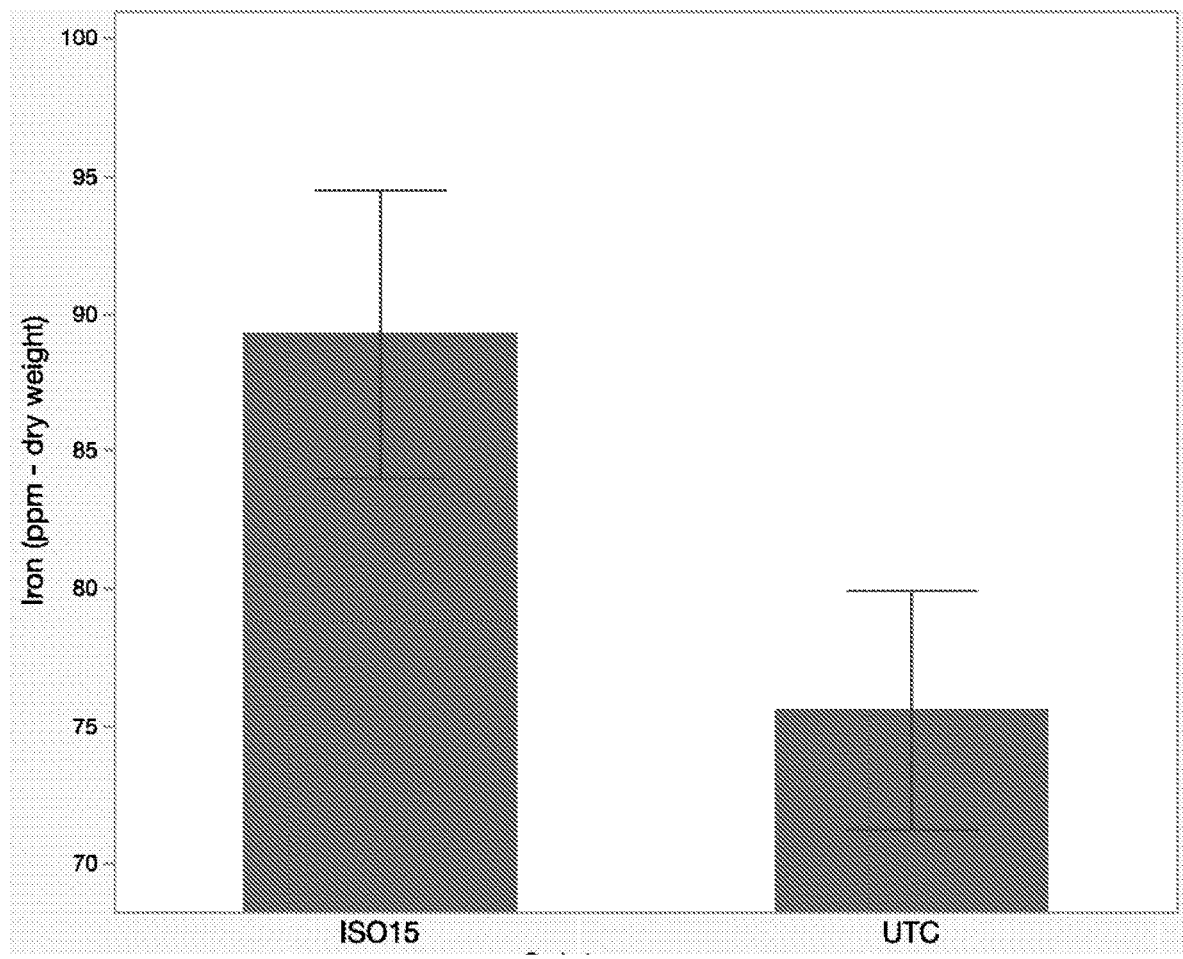
FIG. 12 shows a comparison of iron content of stage V2 leaf samples from corn plants grown from seeds treated with *Methylobacterium* ISO15 and of stage V2 leaf samples from corn plants grown from untreated seeds.
Figure 13:
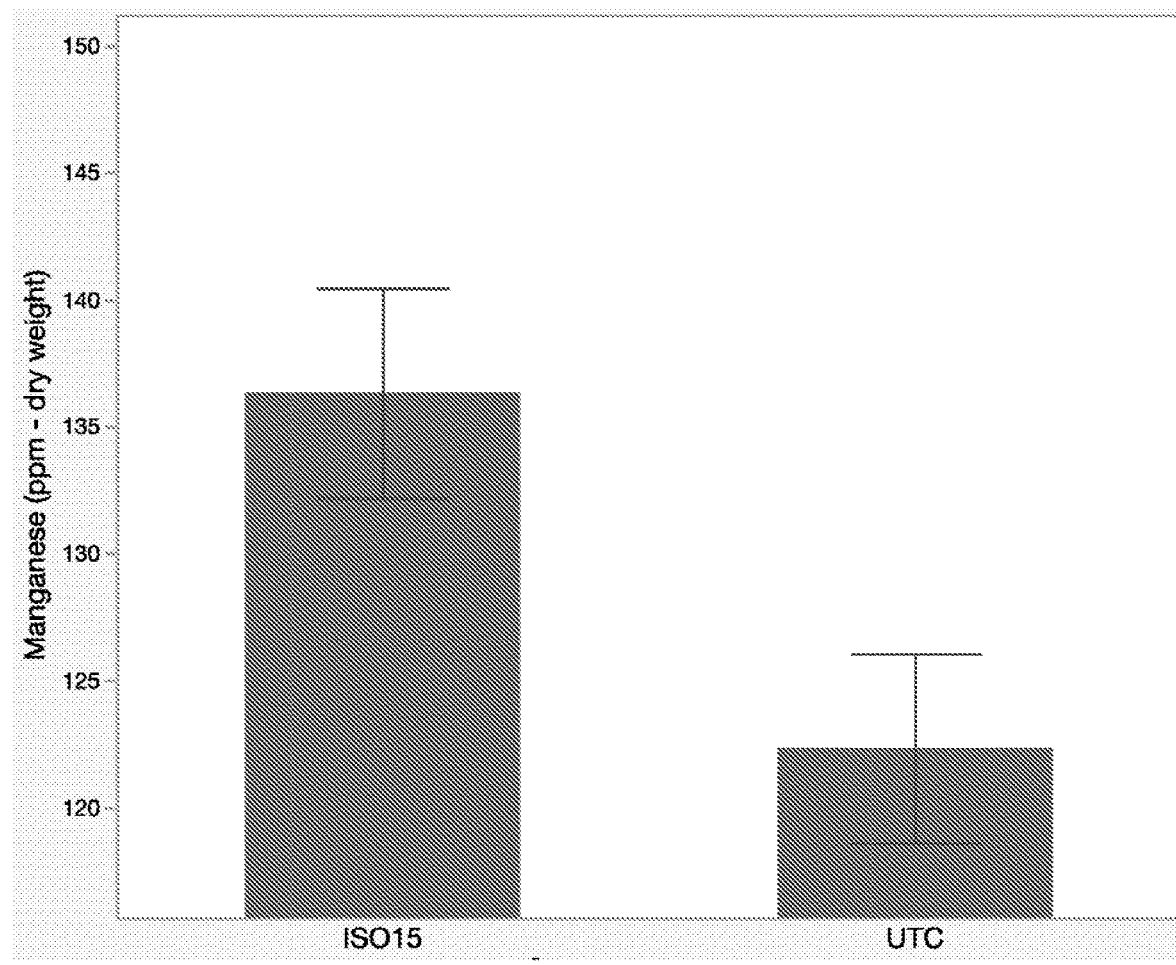
FIG. 13 shows a comparison of manganese content of stage V2 leaf samples from corn plants grown from seeds treated with *Methylobacterium* ISO15 and of stage V2 leaf samples from corn plants grown from untreated seeds.

Example 2. Effects of *Methylobacterium* Strain ISO10 (NRRL B-50938) Treatment of Soybean Seeds on Nutrient Content of Vegetative Tissue Soybean seeds were treated with *Methylobacterium* strain ISO10 at a rate of $10^6$ CFU per seed and grown in sterilized soil (30 seeds per flat) in a greenhouse in parallel with untreated soybean seeds. At 22 days after planting (V1 growth stage), 25 plants per flat were chosen randomly and the youngest fully expanded trifoliate leaf was cut off of each plant. The trifoliates were incubated in sample bags at 45° C. for 4 days to dry and analyzed (Table 3) for macronutrient and micronutrient content. A single-tailed unequal variances (Welch's) t-test was used to determine whether treatment with ISO10 resulted in a significant increase in nutrient content. Iron showed a significant enhancement relative to the UTC. Mean foliar iron content was 7.7% greater following treatment with ISO10, a statistically significant difference (p=0.0403). Results are shown in FIG. 9.

TABLE 3

Mean nutrient contents on a dry weight basis, percent difference of ISO10 from UTC, and contrast p-values.

| Nutrient type | Nutrient (units) | ISO10 value | UTC value | % difference from UTC | Contrast p-value |
|---|---|---|---|---|---|
| Macro-nutrient | Nitrogen (%) | 3.034 | 3.064 | −1.0% | 0.71 |
| | NO3—N (%) | 0.0038 | 0.0050 | −24.0% | 0.92 |
| | Phosphorus (%) | 0.151 | 0.154 | −1.9% | 0.74 |
| | Potassium (%) | 2.573 | 2.577 | −0.2% | 0.56 |
| | Calcium (%) | 1.615 | 1.606 | +0.6% | 0.41 |
| | Magnesium (%) | 0.522 | 0.517 | +1.0% | 0.39 |
| | Sulfur (%) | 0.182 | 0.180 | +1.1% | 0.31 |
| Micro-nutrient | Zinc (ppm) | 21.8 | 21.6 | +0.9% | 0.38 |
| | Manganese (ppm) | 98.6 | 95.7 | +3.0% | 0.17 |
| | Iron (ppm) | 132.1 | 122.7 | +7.7% | *0.040* |
| | Copper (ppm) | 5.4 | 5.5 | −1.8% | 0.63 |
| | Boron (ppm) | 42.7 | 43.5 | −1.8% | 0.76 |

Bold italics indicate p < 0.05.

Example 3. Effects of *Methylobacterium* Strain ISO20 (NRRL B-67743) Treatment of Corn on Nutrient Content of Vegetative Tissue Corn seeds were treated with *Methylobacterium* strain ISO20 at a rate of $10^6$ CFU per seed and grown in sterilized soil (30 seeds per flat) in a greenhouse in parallel with untreated corn seeds. At 22 days after planting (V2 growth stage), 15 or more plants per flat were chosen randomly and shoots were collected by cutting one inch above the soil line. The shoots were incubated in sample bags at 45° C. for 4 days to dry and analyzed for macronutrient and micronutrient content. A single-tailed unequal variances (Welch's) t-test was used to analyze the data to determine whether treatment with ISO15 resulted in a significant increase in nutrient content. *Methylobacterium* ISO15 significantly enhanced foliar nutrient content of four nutrients: phosphorus (P), potassium (K), iron (Fe) and manganese (Mn). Of the 12 nutrients tested, 9 were elevated over the UTC by treatment with ISO15. Results are shown in Table 4 and FIGS. 10-13.

TABLE 4

Mean nutrient contents on a dry weight basis, percent difference of ISO20 from UTC, and contrast p-values.

| Nutrient (units) | ISO20 value | UTC value | % difference from UTC | Contrast p-value |
|---|---|---|---|---|
| Nitrogen (%) | 1.466 | 1.465 | +0.1% | 0.49 |
| NO3—N (%) | 0.0024 | 0.0021 | +14.3% | 0.17 |
| Phosphorus (%) | 0.227 | 0.201 | +12.9% | *0.0062* |
| Potassium (%) | 5.20 | 4.90 | +6.1% | *0.027* |
| Calcium (%) | 0.839 | 0.815 | +2.9% | 0.28 |
| Magnesium (%) | 0.254 | 0.251 | +1.2% | 0.38 |
| Sulfur (%) | 0.216 | 0.226 | −4.4% | 0.80 |
| Zinc (ppm) | 22.8 | 21.6 | +5.6% | 0.15 |
| Manganese (ppm) | 136.3 | 122.3 | +11.4% | *0.0092* |
| Iron (ppm) | 89.3 | 75.6 | +18.1% | *0.028* |
| Copper (ppm) | 6.13 | 6.33 | −3.2% | 0.73 |
| Boron (ppm) | 5.47 | 5.53 | −1.1% | 0.57 |

Bold italics indicate p < 0.05.

Example 4 Detection or Identification of *Methylobacterium* Strains, Variants and Derivatives Assays are disclosed for detection or identification of specific *Methylobacterium* strains and closely related derivatives. Genomic DNA fragments unique to a *Methylobacterium* strain are identified and qPCR Locked Nucleic Acid (LNA) based assays are developed.

Genomic DNA sequences of *Methylobacterium* strains are compared by BLAST analysis of approximately 300 bp fragments using a sliding window of from 1-25 nucleotides to whole genome sequences of over 1000 public and proprietary *Methylobacterium* isolates. Genomic DNA fragments are identified that have weak BLAST alignments, indicative of approximately 60-95% identity over the entire fragment, to corresponding fragments of a *Methylobacterium* of interest. Fragments from the NLS0109 genome corresponding to the identified weak alignment regions were selected for assay development and are provided as SEQ ID NOS: 1-3.

TABLE 5

Target Fragment Sequences of NLS0109

| Fragment | SEQ ID NO | Sequence |
|---|---|---|
| ref1_135566 | 1 | ACGGTCACCCCACGGACTGGGCGAGTACCTCACCGGTGTTCTA TCATAACGCCGAGTTAGTTTTCGACCGTCCCTTATGCGATGTA CCACCGGTGTCGGCAGCCGATTTCGTCCCACCGGGAGCTGGCG TTCCGGTTCAGACCACCATCATCGGTCACGATGTCTGGATTGG ACACGGGGCCTTCATCTCCCCCGGCGTGACTATAGGAAACGGC GCGATCGTCGGGGCCCAGGCGGTCGTCACAAGAGATGTCCCA CCCTATGCGGGTAGTTGCTGGCGTCCCCGCGACCGTACGACGAT |
| ref1_135772 | 2 | CCAATAAAAGCGTTGGCCGCCTGGGCAACCCGATCCGAGCCT AAGACTCAAAGCGCAAGCGAACACTTGGTAGAGACAGCCCGC CGACTACGGCGTTCCAGCACTCTCCGGCTTTGATCGGATAGGC |

TABLE 5-continued

Target Fragment Sequences of NLS0109

| Fragment | SEQ ID NO | Sequence |
|---|---|---|
| | | ATTGGTCAAGGTGCCGGTGGTGATGACCTCGCCCGCCGCAAGC GGCGAATTACTCGGATCAGCGGCCAGCACCTCGACCAAGTGT CGGAGCGCGACCAAAGGGCCACGTTCGAGGACGTTTGAGGCG CGACCAGTCTCGATAGTCTCATCGTCGCGGCGAAGCTGCACCT CGA |
| ref1_169470 | 3 | CGATGGCACCGACCTGCCATGCCTCTGCCGTCCGCGCCAGAAT GGTAAAGAGGACGAAGGGGGTAAGGATCGTCGCTGCAGTGTT GAGCAGCGACCAGAGAAGGGGGCCGAACATCGGCATCAAACC TCGATTGCCACTCGGACGCGAAGCGCGTCTTGAAGGAGGGAT GGAAGCGAAACGGCCGCAGAGTAACCGCCGACGAAAGATTGC ACCCCTCATCGAGCAGGATCGGAGGTGAAGGCAAGCGTGGGT TATTGGTAAGTGCAAAAAATATAATGGTAGCGTCAGATCTAGC GTTC |

Regions in SEQ ID NOS: 1-3 where corresponding regions in other *Methylobacterium* strains were identified as having one or more nucleotide mismatches from the NLS0109 sequence were selected, and qPCR primers designed using Primer3 software (Untergasser et al. (2012), Koressaar et al. (2007)) to flank the mismatch regions, have a melting temperature (Tm) in the range of 55-60 degrees, and to generate a PCR DNA fragment of approximately 100 bp. The probe sequence was designed with a 5' FAM reporter dye, a 3' Iowa Black FQ quencher, and contains one to six LNA bases (Integrated DNA Technologies, Coralville, Iowa). At least 1 of the LNA bases is in the position of a mismatch, while the other LNA bases are used to raise the Tm. The Tm of the probe sequence is targeted to be 10 degrees above the Tm of the primers. Primer and probe sequences for specific detection of NLS0109 are provided as SEQ ID NOS: 4-12 in Table 6. Each of the probes contains a 5' FAM reporter dye and a 3' Iowa Black FQ quencher.

TABLE 6

Primer and Probe Sequences for Specific Detection of NLS0109

| Primer/Probe | SEQ ID NO | Sequence* |
|---|---|---|
| NLS0109_ref1_135566_forward | 4 | CCTCACCGGTGTTCTA TCATAAC |
| NLS0109_ref1_135566_reverse | 5 | CCGATGATGGTGGTCT GAAC |
| NLS0109_ref1_135566_probe | 6 | CGTCCCTTATGCGATG TACCA |
| NLS0109_ref1_135772_forward | 7 | GATCCGAGCCTAAGAC TCAAAG |
| NLS0109_ref1_135772_reverse | 8 | GACCAATGCCTATCCG ATCAA |
| NLS0109_ref1_135772_probe | 9 | AACACTTGGTAGAGAC AGCC |
| NLS0109_ref1_169470_forward | 10 | AAGGAGGGATGGAAGC GAAAC |
| NLS0109_ref1_169470_reverse | 11 | ATAACCCACGCTTGCC TTC |

TABLE 6-continued

Primer and Probe Sequences for Specific Detection of NLS0109

| Primer/Probe | SEQ ID NO | Sequence* |
|---|---|---|
| NLS0109_ref1_169470_probe | 12 | CGCAGAGTAACCGCCG ACGAA |

*Bold and underlined letters represent the position of an LNA base

Use of Primer/Probe Sets on Isolated DNA to Detect NLS0109 and Distinguish from Related *Methylobacterium* Isolates Each 10 ul qPCR reaction contains 5 ul of Quantabio PerfeCTa qPCR ToughMix 2× Mastermix, Low ROX from VWR, 0.5 ul of 10 uM forward primer, 0.5 ul of 10 uM reverse primer, 1 ul of 2.5 uM probe, 1 ul nuclease free water and 2 ul of DNA template. Approximately 1 ng of DNA template is used per reaction. The reaction is conducted in a ThermoFisher QuantStudio™ 6 Flex Real-Time PCR System with the following program: 95° C. for 3 min, then 40 cycles of 95° C. for 15 sec and 60° C. for 1 min. The analysis software on the PCR instrument calculates a threshold and Ct value for each sample. Each sample was run in triplicate on the same qPCR plate. A positive result is indicated where the delta Ct between positive and negative controls is at least 5.

Use of the three primer/probe sets to distinguish NLS0109 from closely related isolates by analysis of isolated DNA is shown in Table 7 below. The similarity score shown for the related isolates takes into account both the average nucleotide identity and the alignment fraction between the isolates and NLS0109. One of the tested strains, NLS0730, was used as an additional positive control. NLS0730 is a clonal isolate of NLS109 which was obtained from a culture of NLS0109, which was confirmed by full genome sequencing as identical to NLS0109, and which scored positive in all three reactions. The similarity score of greater than 1.000 for this strain is likely the result of a slightly different assembly of the genome for this isolate compared to NLS0109. The delta Ct of approximately 15 or more between the NLS0109 and NLS0730 isolates and the water only control is consistent with the sequence confirmation of the identity of these isolates. Analysis of other isolates that are less closely related to NLS0109 results in delta Ct values similar to those for the water only control.

TABLE 7

| NLS# | Similarity score to NLS0109 | Average Ct Value | | |
|---|---|---|---|---|
| | | Refl_135566 | Refl_135772 | Refl_169470 |
| NLS0730 | 1.005 | 21.08 | 21.31 | 20.35 |
| NLS0109 | 1 | 21.97 | 22.62 | 22.08 |
| NLS0731 | 0.181 | No Ct | 37.85 | >37.91 |
| NLS0644 | 0.87 | >36.8 | >38.31 | No Ct |
| NLS0700 | 0.88 | >38.36 | >38.36 | >38.44 |
| NLS0710 | 0.894 | No Ct | >37.47 | >38.13 |
| NLS0834 | 0.852 | 37.81 | No Ct | 37.97 |
| NLS0939 | 0.862 | 37.94 | 38.37 | >38.35 |
| NLS0947 | 0.807 | 38.44 | No Ct | No Ct |
| NLS1015 | 0.894 | 38.77 | No Ct | >37.91 |
| NLS1217 | 0.872 | 37.64 | 37.20 | 37.96 |
| H2O only | | >38.14 | >35.92 | >37.12 |

Use of Primer/Probes for Detection of NLS109 on Treated Plant Materials.

For detection of NLS0109 foliar spray treatment on corn: Untreated corn seeds were planted in field soil in the growth chamber and watered with non-fertilized R.O. water. After plants germinated and grew for approximately 3 weeks, they were transferred to the greenhouse. At V5 stage, plants were divided into 3 groups for treatment: foliar spray of NLS0109, mock foliar spray, and untreated. Plants receiving the foliar spray of NLS0109 were treated with 10× glycerol stock at the rate of 71.4 ul per plant using Solo sprayers. This converts to the rate of 10 L/acre in the field. Mock treated plants were sprayed with 71.4 ul water/plant. Untreated plants received no foliar spray treatment. Leaves were harvested two weeks after foliar spray treatment into sterile tubes and DNA from bacteria on the harvested leaves is isolated as described above. Each experiment was grown at least 2 times. As shown in Table 8, NLS0109 is detected on leaves harvested from corn plants treated by a foliar spray application of the *Methylobacterium* strains using all 3 primer probe sets, as demonstrated by delta Ct values of approximately 10 between the sample and the negative controls.

TABLE 8

| Treatment | Average Ct Value | | |
|---|---|---|---|
| | Refl_135566 | Refl_135772 | Refl_169470 |
| Control (no application) | 32.43 | 32.10 | 31.55 |
| Control (mock application) | 35.54 | 35.34 | 34.80 |
| NLS0109 (10 L/acre equivalent) | 23.36 | 22.88 | 22.66 |

The above results demonstrate the use of genome specific primers and probes to detect *Methylobacterium* strain NLS0109 on various plant tissues following treatment with the strains and provide methods to distinguish NLS0109 from closely related isolates. Similar methods are developed for additional *Methylobacterium* strains, NLS0017, NLS0807, NLS0662 and NLS0648 using target sequence fragments and primer/probe pairs as shown in the Tables below.

TABLE 9

Target Fragment Sequences of NLS0017

| Fragment | SEQ ID NO | Sequence |
|---|---|---|
| ref4_930 | 13 | GCAAAACGACCTAATAGTTCTACAGCGGCATGC GCCAAGTCAGCGCGGTGAACAGTATACCTGGGA GCAACTTGTCCTCCGAAACCCACATAAAACAAA TTACTCCTGGCAGTGCCCAGTCCATCAAAATCG AATACAATATTTCTCGAGGAGGCATCTGTAATA GCCTGCCAAAGCAACAAAGCTATGGCGCCGTTA TGACTTTCATTGCTTCTGGTAGACATAAAATAA TATGCCGATTTGTGATCCCAAATGTAGAATATT GCCGCATCAATTGCGCCAAGTTTATTTCGGATC GAT |
| ref1_142021 | 14 | GGCGCCAACGGTATGATCGCATGATTTTCCTGC GGCATAGCTTGCGGGAATGGCGTATTTGGCGCT CTCCTCAGGAATTTCTAAGGGCATACGCAGGAA CTCTACAGCACTTTTACTGGTATTTTGTAGTGA CAGCGGAGGAGGCTGGTGCTCAAGGTAATCGTG ATGAAGTGATCCGGGCCATTCGGGGCGCGTTTC TAGTCTTTTCCAATCCGCGCCCTGTACCACGTAT TACGCCGGACCGGTCTGCGCCGCGCCGCCCTCT |

TABLE 9-continued

Target Fragment Sequences of NLS0017

| Fragment | SEQ ID NO | Sequence |
|---|---|---|
| | | TGACCGCCCTAAATGTCTAAGAGCGTCTAACAA AGC |
| ref1_142636 | 15 | GACGATATCGCTCATCTTCACTGCATTGAAGCT GGTGCCGTACTGCATAGGGATGAAAAAGTGATG |

TABLE 9-continued

Target Fragment Sequences of NLS0017

| Fragment | SEQ ID NO | Sequence |
|---|---|---|
| | | CGGATAGACGGCTGACGGGAAAGCGCCTGGTCG<br>ATCGAAGACTTTGCTGACGAGGTTGTGGTAGCC<br>CCGGATATAGGCATCGAAGGCCGGGACGTTGAT<br>CCCATCCTTTGCCTTATCTTGACTGGCGTCGTC<br>GCGTGCCGTCAGAACGGGCACGTCGCAGGTCAT<br>CGAGGCCAGCACCTTGCGGAACACCTGCGTTCC<br>GCCGTTGGGATTATCGACGGCGAACGCGGTGGC<br>CGC |

TABLE 10

Primer and Probe Sequences for Specific Detection of NLS0017

| Primer/Probe | SEQ ID NO | Sequence* |
|---|---|---|
| NLS0017_ref4_930_forward | 16 | GTCCTCCGAAACCCACAT AAA |
| NLS0017_ref4_930_reverse | 17 | CTACCAGAAGCAATGAAA GTCAT |
| NLS0017_ref4_930_probe | 18 | TCTGTAATAGCCTGCCAA AGCA |
| NLS0017_ref1_142021_forward | 19 | GGCTGGTGCTCAAGGTAA T |
| NLS0017_ref1_142021_reverse | 20 | ACATTTAGGGCGGTCAAG AG |
| NLS0017_ref1_142021_probe | 21 | ATGAAGTGATCCGGGCCA T |
| NLS0017_ref1_142636_forward | 22 | CCGTACTGCATAGGGATG AAA |
| NLS0017_ref1_142636_reverse | 23 | TAAGGCAAAGGATGGGAT CAA |
| NLS0017_ref1_142636_probe | 24 | TTGCTGACGAGGTTGTGG TAG |

*Bold and underlined letters represent the position of an LNA base

TABLE 11

Target Fragment Sequences of NLS0807

| Fragment | SEQ ID NO | Sequence |
|---|---|---|
| ref1_458355 | 25 | CAACTATGTAGACCCGACGGTGCGATTTCACTTCGCAAAGCCG<br>CAGGGCAGCACCCTTGCGCTCAATGTTGACGCCAGCGTGATCT<br>ATACTATTACCGTCACGCACACGCAGGGCGGCGTACAGATTCA<br>TCGCGAGAGTAAGAACCACCATCAGACCATCACGCGCAGCGA<br>CCTGAGCAAGCAGTTCGGCGTTGGTGTGGCCGACCAGCTGAC<br>GCGCGATCAGGTCATGAAGGTGATCGAGTCGGCATTTCGCGA<br>CGCTACCCGCTAAGATCGGCGCCCACGAAACGCTACGAGACT<br>AGG |
| ref1_459688 | 26 | AGCCGGCATCTTGTTCAAGGCGCTCACCTCGACGCCGACGCTG<br>TAGGCGACTTGAGAGGGCGTCTCATATGAACGAAGCATCTTCG<br>CGTAGAGAACCTTCTTGTTCTCCTGCGTGATGTTCGCTTTGCAG<br>ACGTTGACTGCCGCCATGAACGCCGAAGCCTTGCGCGCTTCAT<br>CGTAATCGCCTGCGAAGGCGGGTAGTGAAAAGCTTAGTGCAA<br>TGGCAAACACAGCCGCCGAACGTCGCATGGTATCCGTCCCCG<br>ATTGACGGCAGTGCCGCCATATCTCGGCTTTAGCAGAGCTGAT |
| ref1_3158527 | 27 | AACCTGCGCCGGCCGAGGTTTCGCGAGCCGTCGCCACGGGCA<br>ACGCCTCGCCCGCGATGTGCAAAAAAGTCCCCGGCACTTCGCG<br>CCGTCGTCCGATCCACGACCGCGAATTTCTCAACGAGTACAAG<br>GTGCTTATGGGAGATCCGAGCGTCCGTCCCGGAGCCCGAGAC<br>CGCGCGGCCCGAGTAATAGGCGAAAAAGACTCCTACTCCTCG<br>GGCTTCTCGGGCCCCCTCAGCAACATCTACGCTTGCCGCCCAT<br>CACCCTGGCGGGAGATCAGCGACGAGACACAGGCCCACTTCG<br>CCC |

TABLE 12

Primer and Probe Sequences for Specific Detection of NLS0807

| Primer/Probe | SEQ ID NO | Sequence* |
|---|---|---|
| NLS0807_ref1_458355_forward | 28 | TTGACGCCAGCGTGATCTATAC |
| NLS0807_ref1_458355_reverse | 29 | GTGATGGTCTGATGGTGGTTCT |
| NLS0807_ref1_458355_probe | 30 | TATTACCGTCACGCACACG |
| NLS0807_ref1_459688_forward | 31 | CTTCGCGTAGAGAACCTTCTTGTT |
| NLS0807_ref1_459688_reverse | 32 | CTTCGCAGGCGATTACGATGAA |
| NLS0807_ref1_459688_probe | 33 | CGTGATGTTCGCTTTGCAGA |
| NLS0807_ref1_3158527_forward | 34 | CCGCGAATTTCTCAACGAGTACA |
| NLS0807_ref1_3158527_reverse | 35 | GCCCGAGGAGTAGGAGTCTTT |
| NLS0807_ref1_3158527_probe | 36 | AGGTGCTTATGGGAGATCCG |

*Bold and underlined letters represent the position of an LNA base

Use of the primer/probe sets to distinguish NLS0807 from closely related isolates by analysis of isolated DNA is shown in Table 13 below. The similarity score shown for the related isolates takes into account both the average nucleotide identity and the alignment fraction between the isolates and NLS0807. Two of the tested strains, NLS0821 and NLS0044, were used as additional positive controls since a similarity score of 1.00 indicates they are nearly identical to NLS0807. Consistently low Ct values from qPCR using NLS0807 as the DNA template and no detection in the water only control is consistent with the sequence confirmation of the identity of these isolates. Analysis of other isolates that are less closely related to NLS0807 results in no detection similar to those for the water only control.

TABLE 13

| NLS# | Similarity to NLS0807 | Average Ct Value ref1_459688 | Average Ct Value ref1_3158527 | Average Ct Value ref1_458355 |
|---|---|---|---|---|
| NLS0807 | 1.00 | 22.39 | 24.09 | 23.10 |
| NLS0821 | 1.00 | 22.49 | 24.04 | 22.96 |
| NLS0044 | 1.00 | 22.49 | 23.86 | 22.90 |
| Strain A | 0.95 | UDT | UDT | UDT |
| Strain B | 0.94 | UDT | UDT | UDT |
| Strain C | 0.93 | UDT | UDT | UDT |
| Strain D | 0.93 | UDT | UDT | UDT |
| water only (neg control) | — | UDT | UDT | UDT |

TABLE 14

Target Fragment Sequences of NLS0648

| Fragment | SEQ ID NO | Sequence |
|---|---|---|
| ref1_1185955 | 37 | AGTCATTGATCAAGCAACCCCTATTGAGTTGGATATCGAAGGATCAAGGTCGCGTCAATAGATGCATCTATCAGGCCAAATGTCGCTTTTCAAGAATGGCTCTTTCGAAGCTATCTTTATAATCGCTCGCCATTCTCTCATTACCAAAATCGACCTTAACTAGCTCGACATTGATGCGAGCAGCTCCGGCAAACGAGGAGAGATTGACCTTAAAGGAATTGAACGCCTCAAGCAATTCAGACACATTACCAGGAGTGCTATAGCAACAACCAGACCCATATCGGTCAATAACCTCTTTTA |
| ref1_3282585 | 38 | CGCAAAACGATTTATCACTGCCATCTTGTTGTTTGATAACCCTTTTTTACCAGACGTTATGCTGGGCGAGAAAGAGGACTAGCAGATCGGAGCGGTATCGCGATTTTTCGGTAGTTCGCGCCTACAACAGGATAAGATCCGATAGTGAAGCAACATGGCTGTTTTTTGATTTGTAAGTCAGCAACTTAAGCAGCCAGCCTATCTGCCGTCGCAGACGCTTGAGGCATCGGGCAGCATCTTAGAAAAGGTGGCAGTAATTGCCACAGCGGAACGTAGCGGCACGGATAAGCACGCAGGGTC |
| ref1_4194637 | 39 | CCCATCTGGACCCAATATCCCCTTCATCGACAATTCCCGAGTAAGTGTGGGTTCGAGGATTTCGCGAAACAGCCTTGTTCGTTCCT |

TABLE 14-continued

Target Fragment Sequences of NLS0648

| Fragment | SEQ ID NO | Sequence |
|---|---|---|
| | | CCGGCCTTAAAATTGGCGTGCCGTCGGGAGATCGATAGGCATC CCTTACCTGCCTTTCGACCGCCGGCACACGCGCGCCGGTCGTC GTGTTCACGGCCACGGAATGGACGAAGGTGCGCCGCTCATTTC GCTCGTTTGCCGTCTCCACCATCCAGGAGGCCAGCAGGACGGT TTCGTCTCGACCGCCGGTCACACACACCGCAAGGGACTCAGG |

TABLE 15 Primer and Probe Sequences for Specific Detection of NLS0648

| Primer/Probe | SEQ ID NO | Sequence* |
|---|---|---|
| NLS0648_ref1_1185955_forward | 40 | TCGCTCGCCATTCTC TCATTAC |
| NLS0648_ref1_1185955_reverse | 41 | AGGTCAATCTCTCCT CGTTTGC |
| NLS0648_ref1_1185955_probe | 42 | TCGACATTGATGCGA GCA |
| NLS0648_ref1_3282585_forward | 43 | TTCGCGCCTACAACA GGATAAG |
| NLS0648_ref1_3282585_reverse | 44 | CAGATAGGCTGGCTG CTTAAGTT |
| NLS0648_ref1_3282585_probe | 45 | TCCGATAGTGAAGCA ACA |
| NLS0648_ref1_4194637_forward | 46 | GAGTAAGTGTGGGTT CGAGGATTT |
| NLS0648_ref1_4194637_reverse | 47 | AGGTAAGGGATGCCT ATCGATCT |
| NLS0648_ref1_4194637_probe | 48 | CGGAGGAACGAACAA GGC |

*Bold and underlined letters represent the position of an LNA base

TABLE 16

Target Fragment Sequences of NLS0662

| Fragment | SEQ ID NO | Sequence |
|---|---|---|
| NLS0662_ref1_4871392 | 49 | ACCTGCTAAAATCACGTCCTCTCAGATTGAAAAAT CATTGAAGAAACGTGTCGAACGATTGCCGGGGATT ATGACGTTAGATCAATTGAAAAATACAAGCTTTGA AATTGAGTTACAGCCAAAAGATGCCCCGGATCCGG ACCCATCAGACTTCGGTGGCTAGTTCGAGCCAAAC TCGAACGTCGCCATGGCGCGCAAGTCGCAATACCA TTTCACAGCGCAGCGGTTATTTCGTTGTACACTGTA GCAATGCGTCGGCTTGCGCGCTTCCGCTGGCGATC AAAGGTCCGCCGATTTACG |
| NLS0662_ref1_1266930 | 50 | TCCCGAACATACAATGGAGGAAGCGTGTGGTAGGC CAATTTGTAACGAAATATGGCATCGGTCACGGCTC TCTCAATAAATTCGATCTCAAGTCTTCTGAACGAG CATGCCTCATCCTTATCCTGAGCGAACGCCTGCCA GTTTGCAGTCATTCCAACATACATAGCCAAAAAGG CGAGGTAGACCTTCATACGGGCACCTCAATCGTCC CCATTCGTTCAAGCTCCTTCAAGATAACAGCCGCA CCACATTGCTGAGATCGAAGATTCGGATCAAATAT TCCATCAAATTTATACTTTC |
| NLS0662_ref1_17614 | 51 | GCATCCTTTGCGCTCGCAGGCCTAAGGTCAAGCCC GGTTACTTCGTTTGGTAGAACGAGGTAGACGATGC CTAGTCTTAAGGTGGCCCATGTTAACCAACAGGGC CAGAACATGATTATAGTTCCGTTAGATGCCAACTT CGGTTACAAAACCGATGGTGAGCAGTCCGACATCA TGTTCGAAATACAGGACGCGGCGCGGTCCGCCGGT CTTGCGGGTGCCGTAGTAGCGTTCTGGCAGTCAGG TGGACAAACCCGTTTCCGGGGCCCGGCTCCGTGGC ACCCATTCCTTCGCAGCCTC |

TABLE 17

Primer and Probe Sequences for Specific Detection of NLS0662

| Primer/Probe | SEQ ID NO | Sequence* |
|---|---|---|
| NLS0662_ref1_4871392_forward | 52 | GCGCAAGTCGCAAT ACCATTTC |
| NLS0662_ref1_4871392_reverse | 53 | CGTAAATCGGCGGA CCTTTGA |
| NLS0662_ref1_4871392_probe | 54 | CGCAGCGGTTATTT CGTTG |
| NLS0662_ref1_1266930_forward | 55 | ACGAGCATGCCTCA TCCTTATC |
| NLS0662_ref1_1266930_reverse | 56 | CGATTGAGGTGCCC GTATGAA |
| NLS0662_ref1_1266930_probe | 57 | TGCCAGTTTGCAGT CATTCC |
| NLS0662_ref1_17614_forward | 58 | CCCGGTTACTTCGT TTGGTAGAA |
| NLS0662_ref1_17614_reverse | 59 | CGAAGTTGGCATCT AACGGAACTA |
| NLS0662_ref1_17614_probe | 60 | TGGCCCATGTTAAC CAACAG |

*Bold and underlined letters represent the position of an LNA base

Use of Primer/Probes for Detection of NLS0807 on Treated Plant Materials

Detection of NLS0807 from In-Furrow Treated Corn Roots

At planting, corn seeds in soil were drenched with NLS0807 and control strains from frozen glycerol stock to simulate in-furrow treatment. To obtain a final concentration of $10^7$ CFU/seed, 100 ul of each strain at $10^8$ CFU/ml is inoculated onto each seed placed in the dibble holes in soil. A 1/10 dilution series is made for lower concentration targets. For control treatment, 100 ul Milli-Q water is applied to each corn seed placed in the dibble holes in soil. Pots containing treated seeds are placed in a growth chamber for approximately two weeks and watered with unfertilized RO water every 1-2 days to keep soil moist. After 2 weeks of growth, roots of about 9 plants per replicate sample were harvested into sterile tubes. Each treatment had at least 2 replicate samples in each experiment, and each experiment was conducted at least 3 times.

DNA from bacteria on the harvested corn roots is isolated as follows. Individual roots are submerged in 20 mL of phosphate-buffered saline (PBS) (137 mM NaCl, 10 mM Phosphate, 2.7 mM KCl, and a pH of 7.4) in 50 mL conical tubes. Tubes are vortexed for 10 minutes, and then sonicated for 10 minutes. Root tissue is removed, and the remaining supernatant from multiple roots of the same sample are combined and centrifuged at 7500×g for 10 minutes. This process is repeated until there is one tube for each sample. The moist soil pellet is vortexed until it evenly coats the tube wall. Tubes are placed into a laminar flow hood with caps removed and open ends of the tubes facing the air blowers. Once dry, samples are stored at room temperature. 250 mg dried soil is used as input for DNA extraction using Qiagen DNeasy PowerSoil HTP 96 kit (Cat #12955-4) using manufacturer protocols.

Primers and probes for NLS0807 disclosed in Table 12 above are used in qPCR reactions to detect the presence of NLS0807 specific fragments provided in Table 11. Each 10 ul qPCR reaction contains 5 ul of Quantabio PerfeCTa qPCR ToughMix 2× Mastermix, Low ROX from VWR, 0.5 ul of 10 uM forward primer, 0.5 ul of 10 uM reverse primer, 1 ul of 2.5 uM probe, 1 ul nuclease free water and 2 ul of DNA template. Approximately 1 ng of DNA template is used per reaction. The reaction is conducted in a ThermoFisher QuantStudio™ 6 Flex Real-Time PCR System with the following program: 95° C. for 3 min, then 40 cycles of 95° C. for 15 sec and 60° C. for 1 min. The analysis software on the PCR instrument calculates a threshold and Ct value for each sample. Each sample is run in triplicate on the same qPCR plate. A positive result is indicated where the delta Ct between positive and negative controls is at least 5.

Use of Primer/Probes for Detection of Variants of Additional Table 1 *Methylobacterium* Isolates Variants of *Methylobacterium* isolates listed in Table 1 are identified by the presence of DNA fragments as described above. Unique fragments for use in such methods are provided in Table 18.

TABLE 18

| Strain | Fragment | SEQ ID NO | Sequence |
|---|---|---|---|
| NLS0020 | ref3_25009 | 61 | GCCCTTCTGTCAGGCGATATTGTATAATGGCGTTGCCC CAATAGAAGCAGCCATTCGTGCGAGGGCAGCAGCGA CGCTAGGTCGAAAGAGCATCCTAATCTCGATCAAGAT GCGACTGAGATTTCTGATGAAAATATCTAGACACAAG CAAAGCTGGTGAAATTACAACGATCATGGCGACAATT GCGGCCAATTCGGCCGGAACTTGAAGGAACATAAAA ATGAATATTACAAATATACCGCAAAGCATGTAGAGTT GCTACACCAAGGGTCGGGACGTCCAAAAAAACTCACT GAGGA |
| NLS0020 | ref3_25219 | 62 | GGAACATAAAAATGAATATTACAAATATACCGCAAA GCATGTAGAGTTGCTACACCAAGGGTCGGGACGTCCA AAAAAACTCACTGAGGAAGTCGACTGGAAGCACGAG GCGCCCCCCCAGGAGCGGGGCGACCGGCAAGGGGG CCCGCAATTGTCGCCATGATCGACCAGCTTAGGTAGG ATCCTCTTTCGACCTAACGAATGGCTGCTTCTATTGGG GCAACGCCATTATACAATATCGCCTGACCATCTGGAA CGCGGCCCGGTCCACCGGCAGGTTGGCGACGACAGC GTCGGAG |

TABLE 18-continued

| Strain | Fragment | SEQ ID NO | Sequence |
|---|---|---|---|
| NLS0020 | ref1_4361220 | 63 | CGGCGTCGACCAGCCGGGCGAACTGCTTGGGCATGCT<br>CTCCCGCGACGCCGGCCACAGCCGCGTCCCCGTCCCT<br>CCGCACAGGATCATCGGGTGGATTTGAAAGGCAAAA<br>CGGGACATCAGGATAGGCCGCTCAGGCGTTGGCGCTG<br>AGGCGCTTGATGTCGGCGTCGACCATCTCGGTGATCA<br>GCGCCTCGAGGCTGGTCTCGGCCTCCCAGCCGAAGGT<br>CGCCTTGGCCTTGGCGGGGTTGCCCAGCAGCACCTCG<br>ACCTCTGCCGGCCGGAACAGCGCCGGGTCGACGATCA<br>GGTGG |
| NLS0020 | ref1_4602420 | 64 | CTGGACATGCGCCCACCCCGGCCAAGTCCGACCGCAC<br>CGGCAACCGCTCCTGTAGTCGTCGTCATCGTTCTCACC<br>CCTGAGGCGGAGACCGTCCGCTAACGGGGTGTCTCAA<br>GCAACCGTGGGGCGGAGGAACACGCACGTAGTCGCG<br>TTTCAAGGTTCGCACGAACGCCTCGGCCATGCCGTTG<br>CTCTGCGGGCTCTCCAGCGGCGTCGTTTTTGGCACCA<br>AACCAAGGTCGCGGGCGAAGCGGCGCGTGTCGCGGG<br>GACTGTCAGGAATTTCGTGTGGGGGCGGCCATAGTGG<br>ATCCG |
| NLS0089 | ref1_194299 | 65 | GGAAATCGGCTTCAAGTACGACGTCACGCCGGCCATG<br>CAGGTCACGGGTGCACTGTTCAATCTCGAGCGCGACA<br>ACCAGCCGTTCCCCTCGAACGTGGAGTCCGGCCTCGT<br>CCTTGGCGCAGGTCAGACACGCACCCAGGGCGCGGA<br>AATCGGCCTGGCCGGCTATCTAACCGATTGGTGGCAG<br>GTCTTTGGCGGCTACGCTTATACCGAGGCACGCGTAC<br>TCTCGCCACTGGAAGACGATGGAGACGTGATCGCAGC<br>AGGTAATCTCGTCGGCAACGTTCCGCTAAATACTTTC<br>AGTCT |
| NLS0089 | ref1_194305 | 66 | CGGCCTGGCCGGCTATCTAACCGATTGGTGGCAGGTC<br>TTTGGCGGCTACGCTTATACCGAGGCACGCGTACTCT<br>CGCCACTGGAAGACGATGGAGACGTGATCGCAGCAG<br>GTAATCTCGTCGGCAACGTTCCGCTAAATACTTTCAGT<br>CTGTTCAACAAGTTCGATATCAACGAGAATTTCTCCG<br>TTGCTCTGGGCTATTACTATCAGGATGCCAGCTTTGCC<br>TCCTCAGACAATGCAGTGCGTTTGCCAAGTTATTCGC<br>GGTTCGATGGCGGGTTGTTCTATCGATTCGACGAGTT<br>GAC |
| NLS0089 | ref1_194310 | 67 | ACGTTCCGCTAAATACTTTCAGTCTGTTCAACAAGTTC<br>GATATCAACGAGAATTTCTCCGTTGCTCTGGGCTATTA<br>CTATCAGGATGCCAGCTTTGCCTCCTCAGACAATGCA<br>GTGCGTTTGCCAAGTTATTCGCGGTTCGATGGCGGGTT<br>GTTCTATCGATTCGACGAGTTGACACGCGTTCAGCTT<br>AGCGTCGAGAACATTTTCGACAGGCGTTACATCATCA<br>ACTCCAACAACAACAACAACCTCACGCCTGGCGCGCC<br>GAGAACAGTCCGCGTGCAATTGATCGCTCGGTTCTAA<br>A |
| NLS0042 | ref1_86157 | 68 | AGCCCACAAGCCTGATGCACTTAACTACATCCTCTAA<br>TGTCGCGCCAATTTGCTTGGCGGCAGGGGATGTTGTA<br>TCGTCATAGGCTTGTCTAACCGGAACTTGTTTGCCAAT<br>CTCTTTGGCGATCGCAACCGCCATCTCGTGTTCGTCAA<br>CCATGTGCGCGTTCCTCTAATTGCACTCATGGTGCCAC<br>GTGCACCTCCGATCGTCTCGTGTCTAGAATGAAGGTG<br>GGAACAACCTTACACAGGCTTTCGCGACGCGCGAATT<br>TCTGGTTTCTCCGCCTCGGATGTGGGTTTGAGCGCTTC |
| NLS0042 | ref1_142469 | 69 | CTTTTCATTTGTCATGATCTCGACCAAGGTATTCACGG<br>CAAGCTCGGTCTGTTGCTTAGCAAGTGCCTGAACTTC<br>GCGAACGATCGGCTCTCGACCCTTCGGGTTCGAGACC<br>TGTCCCTTTTGAAAACCACGTGCCCTACACTTTTCGGG<br>ATCAAGGTGCGGGTTGGCTTTGGTCAAAATTCTCTGG<br>CGTCCCATTACACGCCCTCCGCATCATCGTTCCCGCGA<br>ACGATCTGACCCCCGACTTCCGCGAGGAAGCGTGTGG<br>CGTGATCCTCGAAGCGGAATGCCACCTCGAACTGTTC<br>C |
| NLS0042 | ref1_142321 | 70 | CAGCAGCAAGCAGATCGTTGAAAACCGCTTGAACCGC<br>ATCTTGATCGGGACCGGAACCAATCAGGTCATCTAGG<br>TAAACCGAGACGTAAACTCGTTTGCGCTCGGCATCTT<br>TCAGAACGTCCGTGATGCCAGACCGCATTAGTACCAT<br>CGTCGCCAAGGCGGGCGACTGAACGAAGCCGATCGG<br>CAGAGAGTAACGGGGACCGCCCCTAATCGGGTTGCG |

TABLE 18-continued

| Strain | Fragment | SEQ ID NO | Sequence |
|---|---|---|---|
| | | | AACGCAAGACCACTTAGCAAAGGTTCGAGCACGGCC GAACTTCGCATGGTGGAGAGCCGCGGCAACACGGTTC CGTGATA |
| NLS0064 | ref1_153668 | 71 | TAGACATTCCAACAAACCGGCAAGAGGCTCGTCCTCA CTCGAGGATTTGTTGGGACTTGCATGATGTCGAAGCG GAGCCGTTATGACCTGGGTGCGATCATGCGCCGAGCA TGGGAGATGGCTCGGGAGGCGGCATTCGCGGTTGGCG AGCGGGCACGGACTCACCTTGCTGCCGCGATGCGCAG CGCGTGGGCCGAAGCCAAGTTGGCACTCGCGCCCACG AAGACGGAGCAGGATCGTCTCTCTCCGAGCGACATGA TCGGACATGAGGACGCCTACCAAGGCCGGGTTCTAAA ATAT |
| NLS0064 | ref1_3842117 | 72 | AAGATGGATACGACAAGCGCGATTACATTATTTGCGA AATAGATGGACAAATAAAAGACAAAGGACTGATGTA TTTCCTTAAATCTGGACAAGTTGACCTCTTTCACATAG AAGTCACCACTCCCTTTGGGACAATTTGGTGTCACGA AAACATAGAGGCCGAACTTCTTAGCTGAATTATCGCG CTCCGGGTTCTTATGCGGCTGAGTGAAGCGCGGGACA GCTTGCGAGCAGGGCCGCCAATGGCAGCCGGGATGA CACAATGCTCGGTCTCCCGACGCTTCTTCAATCGGGA GCGCT |
| NLS0064 | ref1_3842278 | 73 | AGCTGAATTATCGCGCTCCGGGTTCTTATGCGGCTGA GTGAAGCGCGGGACAGCTTGCGAGCAGGGCCGCCAA TGGCAGCCGGGATGACACAATGCTCGGTCTCCCGACG CTTCTTCAATCGGGAGCGCTTCGCAGCCCGGGGCGGC GCGCTCATGCGTCACGACCTGGGCCCTGCGCACCTTC GCGGCCCCGCCGTCCCGGCAGATCCCTGATGCCCCAA GTGGGCGGCCACTCCATCAAAGAACCCCGGCCTGTGG CAGATCTCGTAGGCATACCGAGGTTCCGCAGTGCCCC CACC |
| NLS0610 | ref1_2810264 | 74 | ACCGAAGGCGTCCCCGGACACGAAGGCCTGAAACAC CATATCTGTGGCGATCAGGCCGACGTGGTCGCGGACT TCAACTGGCAGAGAATGCCAGGCCGCTTCGATTTCAG ATGATACTGGTACGGACATAGGAGCGGCTTAGCTTTC TCAGTGCAAATGTGATTGATTCCGGCTCAAAAATGAT CTTGATCGGACGAGACGTTTTCAATCCATGTCGTGTTG CCATCGCCGATCGGTGCGTCAAGAGACAGATGGCGCC GACCGTAGATACGCGTTCGGGTTGCCCGCACCGCTTC TCCA |
| NLS0610 | ref1_322980 | 75 | GGAGGTGTGATCTGATGATGTGCTGGATGAAATT GGCGGTCGAGCACTTGTTCAGCTTGGCCAGCTCG ACGAGATCGGCGTGATGCTCGGCGTCGATCAGGA TGTTCAGCGAGACCGGACGTACGCAGGACTTGGT ATTAGCGCCGTTGCGCATCAGCTTGCAGCCTTGC TCTGCTTCTCAGCGTGCCGCGTCAGGATGACCCT GATGTAGCTGTTGAGGTTGATGCCGTAATAGCCT GCGGACTCTGTGAGATCCCGGCGAAGATCGTCGG CGAGGGTCAGGCGGATGGTGCTGGTCGG |
| NLS0610 | ref1_2785241 | 76 | AAGTAACCGCTCAACATGATCTTCAGCATGTTGT CCAACAGCAGGAGAATACATGTAATTCACCATGA CCGGCAAGCTGCGACTGGCCATTGCTTCCACCGC TTGAATGTAGCGATCGAATTTCGCAAAATCAGGG TGGAATGAAAATATCGAACCAAACTGCGAGCCTT GAATCCGTTCTGCAAAATTATCGAAAAATTTTCT TGGCCGACTGCCGTTCGAAAACATTCTTACGTTT ACATGCGGCCCGCCTGAAACAAGACAGTCTACCA GCTCTGGGAAATGGGGGTGAAGGGTCGG |

Example 5. Analysis of Effects of *Methylobacterium* Strains on Nutrient Content of Soybean Vegetative Tissues and on Oil, Protein and Nutrient Content of Seeds of Canola, Corn, Soybean and Wheat Soybean seeds treated as described in Example 1 were grown in multiple field locations in the Midwestern United States in the summer of 2019 in parallel with untreated control soybean plants. Seeds from Canola and wheat were similarly treated and tested. For analysis of field grown corn plants, *Methylobacterium* strains were applied in-furrow at planting. Strains and strain combinations evaluated are shown in Table 19 below.

TABLE 19

| Crop | *Methylobacterium* strain(s) |
| --- | --- |
| Canola | NLS0017 |
| Canola | NLS0020 |
| Canola | NLS0064 |
| Canola | NLS0610 |
| Canola | NLS0017 + NLS0064 |
| Canola | NLS0064 + NLS0066 |
| Canola | NLS0017 + NLS0109 |
| Corn | NLS0042 |
| Corn | NLS0807 |
| Corn | NLS0020 + NLS0042 |
| Corn | NLS0042 + NLS0807 |
| Corn | NLS0648 |
| Corn | NLS0662 |
| Corn | NLS0017 + NLS662 |
| Soybean (+Rhizobia treatment) | NLS0064 |
| Soybean (+Rhizobia treatment) | NLS0610 |
| Soybean (+Rhizobia treatment) | NLS0934 |
| Soybean (+Rhizobia treatment) | NLS0017 + NLS0109 |
| Soybean | NLS0017 |
| Soybean | NLS0064 |
| Soybean | NLS0089 |
| Soybean | NLS0109 |
| Soybean | NLS0020 |
| Soybean | NLS0648 |
| Soybean | NLS0017 + NLS0109 |
| Soybean | NLS0807 |
| Wheat | NLS0017 |
| Wheat | NLS0021 |
| Wheat | NLS0044 |
| Wheat | NLS0064 |
| Wheat | NLS0089 |
| Wheat | NLS0109 |

Preliminary analysis of soybean vegetative issue indicates increase micronutrients were obtained by treatment with *Methylobacterium* strains, including increased boron in RI stage vegetative tissue in soybean plants grown from ISO003 and ISO018-treated seeds, and increased iron in V6 stage vegetative tissue in soybean plants grown from ISO002-treated seeds.

REFERENCES

Bradford, M. M. A rapid and sensitive method for the quantitation of microgram quantities of protein utilizing the principle of protein-dye binding. Anal. Biochem. 1976, 72, 248-254.

Dumas, Ann. Chim. Phys. 1831, T47, 198-213.

Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.

Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.

Green, P. N. and Ardley, J. K. 2018. Review of the genus *Methylobacterium* and closely related organisms: a proposal that some *Methylobacterium* species be reclassified into a new genus, *Methylorubrum* gen. nov. Int J Syst Evol Microbiol. 2018 September; 68(9):2727-2748. doi: 10.1099/ijsem.0.002856.

Hartree, E. F. Determination of protein: a modification of the Lowry method that gives a linear photometric response. Anal. Biochem. 1972, 48, 422-427.

Jokić, S., Nagy, B, Zeković, Z., Vidović, S., Bilić, M., Velić, D., Simándi, B. 2012 Effects of supercritical $CO_2$ extraction parameters on soybean oil yield. Food and Bioproducts Processing 90(4): 4, 693-699.

Konstantinidis K. T., Ramette A., Tiedje J. M. (2006). The bacterial species definition in the genomic era. Philos Trans R Soc Lond B Biol Sci 361: 1929-1940.

Kjeldahl, J. Anal. Chem. 1883, 22, 366-382.

Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.

Maehre, H. K., Dalheim, L., Edvinsen, G. K., Elvevoll, E. O., and Jensen, I. J. (2018) Protein Determination-Method Matters. Foods 7(1), 5; doi:10.3390/foods7010005.

Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220.

Thiex, N. J., Anderson, S., and Gildemeister, B. 2003: Journal Of AOAC International VOL. 86, NO. 2, 2003.

The breadth and scope of the present disclosure should not be limited by any of the above-described embodiments, but should be defined only in accordance with the following claims and their equivalents.

What is claimed is:

1. A method of providing a seed lot with increased mineral nutrient, crude fat, oil, and/or protein content comprising harvesting a seed lot from mature plants grown from seeds and/or plants treated with an effective amount of a *Methylobacterium* strain, wherein the *Methylobacterium* strain is ISO20 (NRRL B-67743), ISO19 (NRRL B-67742), ISO18 (NRRL B-67741), ISO26 (NRRL B-67892), or variant thereof, wherein at least 95% of the seeds in the harvested seed lot are obtained from the mature plants, wherein the harvested seed lot is packaged, contained or otherwise segregated from seed obtained from untreated plants, and wherein at least 95% of the seed in the seed lot comprise the packaged, contained or otherwise segregated seed lot.

2. The method of claim 1, wherein said variant of ISO20 (NRRL B-67743) comprises a sequence selected from the group consisting of SEQ ID NO: 25, 26, and 27; wherein said variant of ISO18 (NRRL B-67741) comprises a sequence selected from the group consisting of SEQ ID NO: 37, 38, and 39; wherein said variant of ISO19 (NRRL B-67742) comprises a sequence selected from the group consisting of SEQ ID NO: 49, 50, and 51; or wherein said variant of ISO26 (NRRL B-67892) comprises a sequence selected from the group consisting of SEQ ID NO: 74, 75, and 76.

3. The method of claim 1, wherein said plants are soybean, *Brassica* sp., corn, sunflower, cotton, flax, alfalfa, rice, rye, wheat, barley, oat, sorghum, millet, safflower, or peanut plants.

4. The method of claim 1, wherein the seeds and/or plants treated with an effective amount of a *Methylobacterium* strain are obtained by a soil treatment or application where the seed and/or plant is contacted and/or colonized by the *Methylobacterium* strain.

5. The method of claim 1, wherein the seeds and/or plants treated with an effective amount of a *Methylobacterium* strain are obtained by spraying, coating, partially coating, immersing, and/or imbibing the plant or seeds with a composition comprising the *Methylobacterium* strain.

6. The method of claim 1, wherein the seeds and/or plants treated with an effective amount of a *Methylobacterium* strain are obtained by spraying, immersing, and/or imbibing soil, a seed, a leaf, a fruit, a stem, a root, a tuber, or a shoot with a liquid, semi-liquid, emulsion, or slurry of a composition comprising the *Methylobacterium* strain.

7. The method of claim 1, further comprising determining the mineral nutrient, crude fat, oil, and/or protein content of the seed lot.

\* \* \* \* \*